US011690841B2

(12) United States Patent
Marelli-Berg

(10) Patent No.: US 11,690,841 B2
(45) Date of Patent: Jul. 4, 2023

(54) GLYCOLYSIS-ACTIVATING AGENTS FOR TREATMENT OR PREVENTION OF DISEASE

(71) Applicant: Queen Mary University of London, London (GB)

(72) Inventor: Federica Maria Marelli-Berg, London (GB)

(73) Assignee: Queen Mary University of London, London (GB)

( * ) Notice: Subject to any disclaimer, the term of this patent is extended or adjusted under 35 U.S.C. 154(b) by 491 days.

(21) Appl. No.: 16/647,440

(22) PCT Filed: Sep. 13, 2018

(86) PCT No.: PCT/GB2018/052603
§ 371 (c)(1),
(2) Date: Mar. 13, 2020

(87) PCT Pub. No.: WO2019/053435
PCT Pub. Date: Mar. 21, 2019

(65) Prior Publication Data
US 2020/0268750 A1  Aug. 27, 2020

(30) Foreign Application Priority Data

Sep. 14, 2017  (GB) ..................................... 1714777

(51) Int. Cl.
| | | |
|---|---|---|
| A61K 31/497 | (2006.01) | |
| A61K 31/44 | (2006.01) | |
| A61K 31/366 | (2006.01) | |
| A61P 37/06 | (2006.01) | |
| A61K 9/00 | (2006.01) | |
| A61K 45/06 | (2006.01) | |

(52) U.S. Cl.
CPC .......... *A61K 31/497* (2013.01); *A61K 9/0053* (2013.01); *A61K 31/44* (2013.01); *A61K 45/06* (2013.01); *A61P 37/06* (2018.01)

(58) Field of Classification Search
CPC ..... A61K 31/497; A61K 31/44; A61K 31/366
USPC ........................................ 514/210.18, 255.06
See application file for complete search history.

(56) References Cited

U.S. PATENT DOCUMENTS

| | | |
|---|---|---|
| 2007/0078168 A1 | 4/2007 | Caulkett |
| 2009/0311228 A1 | 12/2009 | Winqvist et al. |
| 2011/0117069 A1 | 5/2011 | Ansorge et al. |
| 2012/0088760 A1 | 4/2012 | Kim et al. |
| 2012/0142636 A1 | 6/2012 | Ryono et al. |
| 2012/0149704 A1 | 6/2012 | Kharul |
| 2012/0165375 A1 | 6/2012 | Murray et al. |
| 2012/0178765 A1 | 7/2012 | Yi et al. |
| 2012/0184544 A1 | 7/2012 | Kharul et al. |
| 2012/0214735 A1 | 8/2012 | Bhuniya et al. |
| 2012/0225887 A1 | 9/2012 | Cheruvallath et al. |
| 2012/0252814 A1 | 10/2012 | Cheruvallath et al. |
| 2012/0277242 A1 | 11/2012 | Aicher et al. |
| 2013/0029939 A1 | 1/2013 | Meng et al. |
| 2013/0131113 A1 | 5/2013 | Haynes et al. |
| 2013/0165452 A1 | 6/2013 | Benbow et al. |
| 2013/0252973 A1 | 9/2013 | Pfefferkorn et al. |
| 2014/0288168 A1 | 9/2014 | Choi et al. |

FOREIGN PATENT DOCUMENTS

| | | |
|---|---|---|
| EP | 2406230 A1 | 1/2012 |
| EP | 2444397 A1 | 4/2012 |
| EP | 2513103 A1 | 10/2012 |
| EP | 2543667 A1 | 1/2013 |
| EP | 2582706 A1 | 4/2013 |
| JP | 2007-509917 A | 4/2007 |
| JP | 2009-506109 A | 2/2009 |
| KR | 10-0414453 B1 | 4/2004 |
| KR | 10-2006-0121998 A | 11/2006 |
| KR | 10-2009-0047851 A | 5/2009 |
| KR | 10-2009-0079608 A | 7/2009 |
| KR | 101095401 B1 | 12/2011 |
| WO | 2000/058293 A2 | 10/2000 |
| WO | 2001/044216 A1 | 6/2001 |
| WO | 2003/000267 A1 | 1/2003 |
| WO | 2003/015774 A1 | 2/2003 |
| WO | 2003/055482 A1 | 7/2003 |
| WO | 2003/080585 A1 | 10/2003 |
| WO | 2003/095438 A1 | 11/2003 |
| WO | 2004/002481 A1 | 1/2004 |
| WO | 2004/076420 A1 | 9/2004 |
| WO | 2005/044801 A1 | 5/2005 |
| WO | 20070027132 A1 | 3/2007 |
| WO | 2008/050101 A2 | 5/2008 |

(Continued)

OTHER PUBLICATIONS

Ammirati, E, et al, "Effector Memory T Cells are Associated With Atherosclerosis in Humans and Animal Models", Journal of the American Heart Association, vol. 1, Feb. 2012, pp. 27-41.
Bain, S.C., et al, "Lack of association between type 1 diabetes and the glucokinase gene", Lancet, vol. 340, Jul. 1992, pp. 54-55.
Baragetti, et al, "Telomere shortening over 6 years is associated with increased subclinical carotid vascular damage and worse cardiovascular prognosis in the general population", Journal of internal medicine, vol. 277, Apr. 2015, pp. 478-487.
Beer, et al, "The P446L variant in GCKR associated with fasting plasma glucose and triglyceride levels exerts its effecl through increased glucokinase activity in liver". Human Molecular Genetics, vol. 18, Issue 21, Nov. 2009, pp. 4081-4088.
Bernstein, et al, "Actin-ATP hydrolysis is a major energy drain for neurons", The Journal of neuroscience: the official journal of the Society for Neuroscience, vol. 23, Jan. 2003, pp. 1-6.

(Continued)

*Primary Examiner* — Raymond J Henley, III
(74) *Attorney, Agent, or Firm* — Holland & Hart LLP

(57) ABSTRACT

The present invention relates to glycolysis-activating agents. The present invention also relates to the treatment or prevention of diseases or medical conditions, in particular immune-related diseases or medical conditions. In particular, the present invention also relates to agents for use in the treatment or prevention of a disease or medical condition, which treatment or prevention is mediated via the trafficking of endogenous regulatory T cells (Tregs).

15 Claims, 29 Drawing Sheets

(56) References Cited

FOREIGN PATENT DOCUMENTS

| WO | 2008/050117 | A1 | 5/2008 |
|---|---|---|---|
| WO | 2008/075073 | A1 | 6/2008 |
| WO | 2010/103438 | A1 | 9/2010 |
| WO | 2011/073117 | A1 | 6/2011 |
| WO | 2011/157682 | A1 | 12/2011 |
| WO | 2012/007758 | A2 | 1/2012 |
| WO | 2012/088157 | A2 | 6/2012 |
| WO | 20120112626 | A2 | 8/2012 |
| WO | 2012/150202 | A1 | 11/2012 |
| WO | 2013/086397 | A1 | 6/2013 |

OTHER PUBLICATIONS

Bonn, et al, "The discovery of a novel series of glucokinase activators based on a pyrazolopyrimidine scaffold", Bioorganic & medicinal chemistry letters, vol. 22, 2012, pp. 7302-7305.

Bosca, et al, "Phorbol 12,13-dibutyrate and mitogens increase fructose 2,6-bisphosphate in lymphocytes. Comparison of lymphocyte and rat-liver 6-phosphofructo-2-kinase", Eur J Biochem vol. 175, 1988, pp. 317-323.

Boulbes, et al, "Rictor phosphorylation on the Thr-1135 site does not require mammalian target of rapamycin complex 2", Mol Cancer Res vol. 8, 2010, pp. 896-906.

Chang, T.T., et al, "Studies in B7-deficient mice reveal a critical role for B7 costimulation in both induction and effector phases of experimental autoimmune encephalomyelitis", J Exp Med vol. 190, 1999, pp. 733-740.

Chen, Z., et al, "Where CD4+CD25+T reg cells impinge on autoimmune diabetes", J Exp Med vol. 202, 2005, pp. 1387-1397.

Chi, H., "Regulation and function of mTOR signalling in T cell fate decisions", Nature reviews Immunology 12, 2012, pp. 325-338.

Clarke, F.M., et al, "On the association of glycolytic enzymes with structural proteins of skeletal muscle", Biochim Biophys Acta 381, 1975, pp. 37-46.

Cooles, et al, "Treg Cells in Rheumatoid Arthritis: An Update", CurrRheumatol Reports vol. 15, 2013, pp. 352.

Cybulski, N., et al, "TOR complex 2: a signaling pathway of its own", Trends Biochem Sci vol. 34, 2009, pp. 620-627.

Dang, E.V., et al, "Control of T(H) 17 /T(reg) balance by hypoxia-inducible factor 1", Cell vol. 146, 2011, pp. 772-784.

Deng, Y., et al, "The Inflammatory Response m Psoriasis: a Comprehensive Review", Clin Rev Allergy Immunol vol. 50, 2016, pp. 377-389.

Denning, T.L., et al, Cutting edge: CD4+CD25+ regulatory T cells impaired for intestinal homing can prevent colitis. J Immunol vol. 174, 2005, pp. 7487-7491.

Ding, Y., et al, "T regulatory cell migration during an immune response", Trends Immunol vol. 33, 2012, pp. 174-180.

Farrelly, D., et al, "Mice mutant for glucokinase regulatory protein exhibit decreased liver glucokinase: a sequestration mechanism in metabolic regulation". Proc Natl Acad Sci US A vol. 96, 1999, pp. 14511-14516.

Frauwirth, et al, "The CD28 signaling pathway regulates glucose metabolism", Immunity vol. 16, 2002, pp. 769-777.

Fu, H., et al., "Mechanisms of T cell organotropism", Cell Mol Life Sci vol. 73, 2016, pp. 3009-3033.

Fu, H., et al, "Self-recognition of the endothelium enables regulatory T-cell trafficking and defines the kinetics of immune regulation", Nat Commun vol. 5, 2014, pp. 3436.

Gan, X., et al, "Evidence for direct activation of mTORC2 kinase activity by phosphatidylinositol 3,4,5-trisphosphate", J Biol Chem vol. 286, 2011, pp. 10998-11002.

Gerriets, V.A., et al., "Foxp3 and Toll-like receptor signaling balance Treg cell anabolic metabolism for suppression", Nat Immunol vol. 17, 2016, pp. 1459-1466.

Grewal, AS., et al, "Recent Updates on Glucokinase Activators for the Treatment of Type 2 Diabetes Mellitus", Mini Rev Med Chem vol. 14, 2014, pp. 585-602.

Haas, R., et al, "Lactate Regulates Metabolic and Pro-inflammatory Circuits in Control of T Cell Migration and Effector Functions", PLoS biology vol. 13, 2015, e 1002202.

Hagiwara, A., et al, "Hepatic mTORC2 activates glycolysis and lipogenesis through Akt, glucokinase, and SREBPIc", Cell Metab vol. 15, 2012, pp. 725-738.

Humrich, J.Y et al, "Restoring regulation—IL-2 therapy in systemic lupus erythematosus", Exp Rev Clin Immunol vol. 12, 2016, pp. 1153-1160.

International Preliminary Report on Patentability received for PCT Patent Application No. PCT/GB2018/052603, dated Mar. 26, 2020, 7 pages.

International Search Report and Written Opinion received for PCT Patent Application No. PCT/GB2018/052603, dated Dec. 7, 2018, 9 pages.

Jacobs, S.R., et al., "Glucose uptake is limiting in T cell activation and requires CD28-mediated Akt-dependent and independent pathways", J Immunol vol. 180, 2008, pp. 4476-4486.

Jain, N., et al, "CD28 and ITK signals regulate autoreactive T cell trafficking", Nat Med vol. 19, 2013, pp. 1632-1637.

Jarmin, S.J., et al, "Targeting T cell receptor-induced phosphoinositide-3-kinase pl I0delta activity prevents T cell localization to antigenic tissue", J Clin Invest vol. 118, 2008, pp. 1154-1164.

Jung, J., et al, "Interaction of cofilin with triose-phosphate isomerase contributes glycolytic fuel for Na,K-ATPase via Rho-mediated signaling pathway", J Biol Chem vol. 277, 2002, pp. 48931-48937.

Lenzen, S. "A fresh view of glycolysis and glucokinase regulation: history and current status", The Journal of biological chemistry vol. 289, 2014, pp. 12189-12194.

Livak, K.J., et al, "Analysis of relative gene expression data using real-time quantitative PCR and the 2(-Delta Delta C(T)) Method", Methods vol. 25, 2001, pp. 402-408.

Lorenz, M.W., et al, "Carotid intima-media thickness progression to predict cardiovascular events in the general population (the PROGIMT collaborative project): a meta-analysis of individual participant data", Lancet vol. 379, 2012, pp. 2053-2062.

Marelli-Berg, et al, "Isolation of endothelial cells from murine tissue", J Immunol Methods vol. 244, 2000, pp. 205-215.

Marjanovic, S., et al, "Expression of a new set of glycolytic isozymes in activated human peripheral lymphocytes", Biochim Biophys Acta vol. 1087, 1990, pp. 1-6.

Michalek, R.D., et al, "Cutting edge: distinct glycolytic and lipid oxidative metabolic programs are essential for effector and regulatory CD4+ T cell subsets", J Immunol vol. 186, 2011, pp. 3299-3303.

Mirenda, V., et al, "Physiological and aberrant regulation of memory T cell trafficking by the costimulatory molecule CD28", Blood vol. 109, 2007, pp. 2968-2977.

Muller, N., et al, "A CD28 superagonistic antibody elicits 2 functionally distinct waves of T cell activation in rats", J Clin Invest vol. 118, 2008, pp. 1405-1416.

Murata, T., et al, "Go-localization of glucokinase with actin filaments", FEBS Lett vol. 406, 1997, pp. 109-113.

Newson, J., et al, "Resolution of acute inflammation bridges the gap between innate and adaptive immunity", Blood vol. 124, 2014, pp. 1748-1764.

Nlasui, K., et al, "mTORC2 in the center of cancer metabolic reprogramming", Trends Endocrinol Metab vol. 25, 2014, pp. 364-373.

Norata, G.D., et al, "Girculating soluble receptor for advanced glycation end products is inversely associated with body mass index and waist/hip ratio in the general population", Nutrition, metabolism, and cardiovascular diseases: NMCD vol. 19, 2009, pp. 129-134.

Norata, G.D., et al, "Effect of the −420C/G variant of the resistin gene promoter on metabolic syndrome, obesity, myocardial infarction and kidney dysfunction", Journal of internal medicine vol. 262, 2007, pp. 104-112.

Norata, G.D., et al, "Effects of fractalkine receptor variants on common carotid artery intima-media thickness", Stroke vol. 37, 2006, pp. 1558-1561.

(56) References Cited

OTHER PUBLICATIONS

O'Sullivan, D., et al, "Memory CD8(+) T cells use cellintrinsic lipolysis to support the metabolic programming necessary for development", Immunity vol. 41,2014, pp. 75-88.
Okkenhaug, K., et al, "A point mutation in CD28 distinguishes proliferative signals from survival signals", Nat Immunol vol. 2, 2001, pp. 325-332.
Kishore, Madhav et al. "Regularary T Cell Migration is Dependent on Glucokinase-Mediated Glycolysis," Immunity, Cell Press, U.S., vol. 47:5 2017, pp. 875-889, 26 pages.
Anaya-Eugenio et al., Hypoglycemic properties of some preparations and compounds from Artemisia ludoviciana Nutt, Journal of Ethnopharmacology , 2014, http://dx.doi.org/10.1016/jjep.2014.05.051.
Berge et al, "Pharmaceutical Salts", J. Pharmaceutical Sciences, vol. 66, pp. 1-19 (1977).
Bettancourt et al, "Targeting Metabolism as a Novel Therapeutic Approach to Autoimmunity, Inflammation, and Transplantation", Journal of Immunology, vol. 198, 2017, pp. 999-1005.
Cheong et al, "Eupatilin inhibits gastric cancer cell growth by blocking STAT3-mediated VEGT expression", J Gastric Cancer, vol. 11, No. 1, 2011, pp. 16-22.
Escandón-Rivera et al., "Molecules Isolated from Mexican Hypoglycemic Plants: A Review", Molecules, vol. 25, 2020, pp. 4145.
Hansch, Corwin (Chairman of Editorial Board) Chapter 25.2 in vol. 5 of Comprehensive Medicinal Chemistry, Pergamon Press 1990.
Hansch, Corwin (Chairman of Editorial Board), Routes of Administration and Dosage Regimes, Chapter 25.3 in vol. 5 of Comprehensive Medicinal Chemistry, Pergamon Press 1990.
Nadkarni et al., "Regulation of Glucose Homeostasis by GLP-1", Prog. Mol. Biol. Transl. Sci., vol. 121, 2014, pp. 23-65.
Niaaj et al., "Isolation and Inhibitory Effects of Eupatilin, a Flavone Isolated from Artemisia monosperma Del., on Rat Isolated Smooth Muscle", International Journal of Pharmacognosy, vol. 34, Issue 2, 1996, pp. 134-140.
Procaccini et al.,"An oscillatory switch in mTOR kinase activity sets regulatory T cell responsiveness", Immunity, vol. 33, 2010, pp. 929-941.
Qi et al.,"Anti-Diabetic Agents from Natural Products—An Update from 2004-2009", Current Topics in Medicinal Chemistry, 2010, vol. 10, pp. 434-457.
Reese et al., "Functional Status, Time to Transplantation, and Survival Benefit of Kidney Transplantation Among Wait-Listed Candidates", American journal of kidney disease, vol. 66, No. 5, Nov. 2015, pp. 837-845.
De Rossa et al., "Glycolysis controls the induction of human regulatory T cells by modulating the espressino of FOXP3 exon 2 splicing variants", Glycolysis and FAO in the generation and function of iTreg cells, Nature immunology, vol. 16, No. 1, pp. 1174-1184.
Parry, RV., et al, "CTLA-4 and PD-1 receptors inhibit T-cell activation by distinct mechanisms", Molecular and cellular biology vol. 25, 2005, pp. 9543-9553.
Powell, J.D., et al, "The mammalian target of rapamycin: linking T cell differentiation, function, and metabolism", Immunity vol. 33, 2010, pp. 301-311.
Schneider, H., et al, "CTLA-4 upregulation of lymphocyte function-associated antigen 1 adhesion and clustering as an alternate basis for coreceptor function". Proc Natl Acad Sci US A vol. 102, 2005, pp. 12861-12866.
Shi, L.Z., et al, "HIFIalpha-dependent glycolytic pathway orchestrates a metabolic checkpoint for the differentiation of THI 7 and Treg cells", The Journal of experimental medicine vol. 208, 2011, pp. 1367-1376.
Stephenson, E., et al, "T-cell immunity in myocardial inflammation: pathogenic role and therapeutic manipulation", Br J Pharmacol, 2016, DOI: 10.1111/bph.13613.
Tai, X., et al., CD28 costimulation of developing thymocytes induces Foxp3 expression and regulatory T cell differentiation independently of interleukin 2, Nature immunology vol. 6, 2005, pp. 152-162.
Tang, Q., et al, "CD4(+)Foxp3(+) regulatory T cell therapy in transplantation", J Mol Cell Biol vol. 4, 2012, pp. 11-21.
Tang, Q., et al, "Distinct roles of CTLA-4 and TGF-beta in CD4+CD25+ regulatory T cell function", European journal of immunology vol. 34, 2004, pp. 2996-3005.
Van der Windt, G.J., et al, "CDS memory T cells have a bioenergetics advantage that undedies their rapid recall ability". Proc Natl Acad Sci U S A vol. 110, 2013, pp. 14336-14341.
Wang, R., et al, "The transcription factor Myc controls metabolic reprogramming upon T lymphocyte activation", Immunity vol. 35, 2011, pp. 871-882.
Weirather, J., et al, Foxp3+ CD4+ T Cells Improve Healing After Myocardial Infarction by Modulating Monocyte/Macrophage Differentiation. Circ Res vol. 115, 2014, pp. 55-67.
Wells, A.D., et al, "Signaling through CD28 45 and CTLA-4 controls two distinct forms of T cell energy", J Clin Invest vol. 108, 2001, pp. 895-903.
Wieman, H.L., et al, "Cytokine stimulation promotes glucose uptake via phosphatidylinositol-3 kinase/ Akt regulation of Glut 1 activity and trafficking", Molecular biology of the cell vol. 18, 2007, pp. 1437-1446.
Wing, K., et al, "CTLA-4 control over Foxp3+ regulatory T cell function", Science vol. 322, 2008, pp. 271-275.
Zheng, Y., et al, "Anergic T cells are metabolically anergic", J Immunol vol. 183, 2009, pp. 6095-6101.
Zom, E., et al, "Reduced frequency of FOXP3+ CD4+CD25+ regulatory T cells in patients with chronic graft-versus-host disease", Blood vol. 106, 2005, pp. 2903-2911.
Japan Patent Office, "Notice of Reasons for Refusal", issued in connection with Japan Patent Application No. 2020-514560 dated Sep. 21, 2022 (15 pages).
Kim, J., et al., "Eupatilin Ameliorates Collagen Induced Arthritis", J. Korean Med Sci., Mar. 2015, vol. 30, No. 3, pp. 233-239.
Beres, A. et al., "The Role of Regulatory T Cells in the Biology of Graft Versus Host Disease", Front Immunol., vol. 4, Article 163, Jun. 2013, pp. 1-9.
Campbell, D. J. "Control of Regulatory T Cell Migration, Function, and Homeostasis", Journal of Immunology, vol. 195, No. 6, 2015, pp. 2507-2513.
Glick, A. B. et al., "Impairment of Regulatory T-Cell Function in Autoimmune Thyroid Disease", Thyroid, vol. 23, No. 7, Jul. 2103, pp. 871-878.
Li, M. O. et al., "T cell receptor signalling in the control of regulatory T cell differentiation and function", Nature Reviews Immunology, vol. 16, 2016, pp. 220-233.
Mas, A. et al., "Reversal of Type 1 Diabetes by Engineering a Glucose Sensor in Skeletal Muscle", Diabetes, vol. 55, Jun. 2006, pp. 1546-1553.
Montane, J. et al., Recovery from Type 1 Diabetes by Insulin and Glucokinase Expression in Skeletal Muscle, Molecular Therapy, vol. 11, Supplement 1, May 2005, S349.
O'Brien, "Gene therapy for Type 1 Diabetes moves a step closer to reality", Diabetes, May 2013, vol. 62, pp. 1396-1397.
Okuko, Y et al., "Treg activation defect in type 1 diabetes: correction with TNFR2 agonism", Clin Transl Immunology. Jan. 2016; 5(1): e56.
Palomares, O. et al., "Role of Treg in immune regulation of allergic diseases", European Journal of Immunology, vol. 40, issue 5, 2010, pp. 1232-1240.
Tang, Q et al., "Central role of a defective interleukin-2 production in triggering islet autoimmune destruction", Immunity, vol. 28, No. 5, May 2008, pp. 687-697 (Supplemental Data).
Tang, Q et al., "Central role of a defective interleukin-2 production in triggering islet autoimmune destruction", Immunity, vol. 28, No. 5, May 2008, pp. 687-697.

GLYCOLYSIS-ACTIVATING AGENTS FOR TREATMENT OR PREVENTION OF DISEASE

CROSS REFERENCE TO RELATED APPLICATIONS

This application is a U.S. National Entry and claims priority to PCT International Patent Application No. PCT/GB2018/052603, filed Sep. 13, 2018, and entitled "AGENT", which claims priority to United Kingdom Patent Application No. 1714777.8 filed Sep. 14, 2017, the entire disclosures of which are incorporated herein by this reference.

FIELD OF THE INVENTION

The present invention relates generally to the field of medicine. Further, various embodiments relate to pharmaceutical medicine. In particular, the invention relates to agents and compositions useful in the trafficking of endogenous regulatory T cells (Tregs) in a subject suffering from or at risk of suffering from a disease or medical condition, in particular immune-related diseases and medical conditions.

BACKGROUND

Thymic regulatory T cells (Treg), defined as $CD4^+CD25^+$ $Foxp3^+$ T cells, are instrumental for the maintenance of tolerance to self-antigens. Tregs exert their immunomodulatory role by localizing to both lymphoid and non-lymphoid tissue.

Migration of Treg cells to inflamed tissue is key to their immune modulatory function. A rapid accumulation of Treg relative to T effector (Teff) cells—in which over 30% of the infiltrating lymphocytes are Tregs—occurs in inflamed tissue during immune regulation (Tang et al., 2012). By contrast, the small proportion of Tregs in the peripheral blood (2-5%) further emphasizes the remarkable migratory ability of Tregs.

The bioenergetics of Teff and Treg function, expansion and survival has been extensively studied. Teff and Treg cells require distinct metabolic programmes to support their survival and differentiation: T helper (Th)1, Th2, and Th17 cells express high surface amounts of glucose transporter Glut1 and are highly glycolytic, whereas Treg cells express low amounts of Glut1 and have high lipid oxidation rates in vitro (Michalek et al., 2011). The mammalian target of rapamycin (mTOR) plays a key role in cell fate decision by regulating T cell metabolic responses. T cell activation stimulates mTOR to increase glycolysis and diminish lipid oxidation (Wieman et al., 2007). In contrast, blockade of glycolysis promotes generation of Treg cells, and this occurs via inhibition of mTOR-mediated induction of the transcription factor hypoxia-inducible factor (HIF1α) (Dang et al., 2011; Shi et al., 2011). However, while Tregs mainly rely upon an oxidative metabolism, some specific functions can be dependent on a selective switch to glycolysis. Treg metabolism appears to oscillate from mTOR-dependent and -independent pathways in response to environmental cues (Procaccini et al., 2010). Toll-like receptor (TLR) signals have been shown to promote Treg cell proliferation via mTORC1 signaling, glycolysis and Glut1 upregulation. In contrast TLR-induced mTORC1 signals also reduced Treg suppressive ability (Gerriets et al., 2016).

Despite motility being likely the most energy-consuming cellular activity (Bernstein and Bamburg, 2003), the metabolic demands for T cell migration have only been partly investigated. We have previously shown that Teff migration relies upon the glycolytic pathway (Haas et al., 2015). However, the metabolic programme(s) that fuel Treg migration remain unknown.

Molecular interactions mediated by integrins such as LFA-1 are the canonical regulator of T cell trafficking. In addition, signals generated by the co-stimulatory and co-inhibitory receptors CD28 and CTLA-4, respectively, actively participate in the regulation of T cell trafficking. In the lymph nodes, CD28 activation promotes memory T cell egression and migration to target tissue (Jain et al., 2013; Mirenda et al., 2007), while CTLA-4 antagonizes CD28 pro-migratory signals (Mirenda et al., 2007). Effector Treg cell migration is also regulated by CD28 signals (Muller et al., 2008). Importantly, costimulatory receptors also regulate T cell metabolic reprogramming to enhanced glycolysis (Frauwirth et al., 2002; Parry et al., 2005), however a link between glycolysis and migration of Treg cells has not previously been suggested.

The process of glycolysis is controlled in part by the enzyme glucokinase (GCK or GLK). The rate of glucose uptake is limited by the rate of phosphorylation of glucose to glucose-6-phosphate (G6P), a process which is catalysed by GCK.

WO2008050101 describes a group of benzoyl amino heterocyclyl compounds that are GCK activators with advantageous physical and/or pharmacokinetic properties and/or a favourable toxicity profile.

WO2008050117 describes benzoyl amino heterocyclyl compounds as GCK activators with higher aqueous solubility, higher permeability and/or lower plasma protein binding.

WO2008075073 describes a crystalline form that is a GCK activator and useful for decreasing the glucose threshold for insulin secretion.

In WO0058293 and WO0144216, a series of benzyl carbamoyl compounds are described as glucokinase activators. The mechanism by which such compounds activate GCK is assessed by measuring the direct effect of such compounds in an assay in which GCK activity is linked to NADH production, which in turn is measured optically.

Further GCK activators have been described in WO03095438 (substituted phenylacetamides), WO03055482 (carboxamide and sulphonamide derivatives), WO2004002481 (arylcarbonyl derivatives), and in WO03080585 (amino-substituted benzoylaminoheterocycles).

WO03000267 describes a group of benzoyl amino pyridyl carboxylic acids which are activators of GCK. WO03015774 describes compounds of the Formula (A):

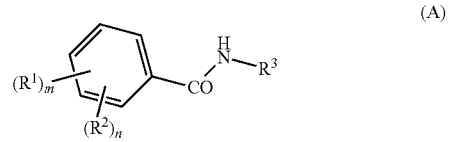

(A)

wherein R3 is a phenyl or a substituted heterocycle other than a carboxylic acid substituted pyridyl.

WO2004076420 describes compounds which are generally a subset of those described in WO03015774, wherein for example R1 is an (substituted) alkyl ether and R2 is (substituted) phenoxy.

Grewal et al., 2014 lists a number of GCK activators (GKAs) for the treatment of Type 2 diabetes mellitus. It has been noted previously that there is a lack of association between Type 1 diabetes mellitus and the glucokinase gene (Bain et al., 1992).

Tregs have been found at target sites or have been shown to migrate to target sites in a number of disease states. Tregs also play a crucial role in resolving a number of disease states. Such disease states include multiple sclerosis (Denning et al., 2005), myocarditis (Stephenson et al., 2016), myocardial infarction (MI) (Weirather et al., 2014), Type I diabetes (Chen et al., 2005), rheumatoid arthritis (RA) (Cooles et al., 2013), systemic lupus erythematosus (SLE) (Humrich & Riemekasten, 2016), psoriasis (Deng et al., 2016), graft versus host disease (GVHD) (Zorn et al., 2005), colitis (Ding et al., 2012) and allergic diseases (Denning et al., 2005).

Figure 11:
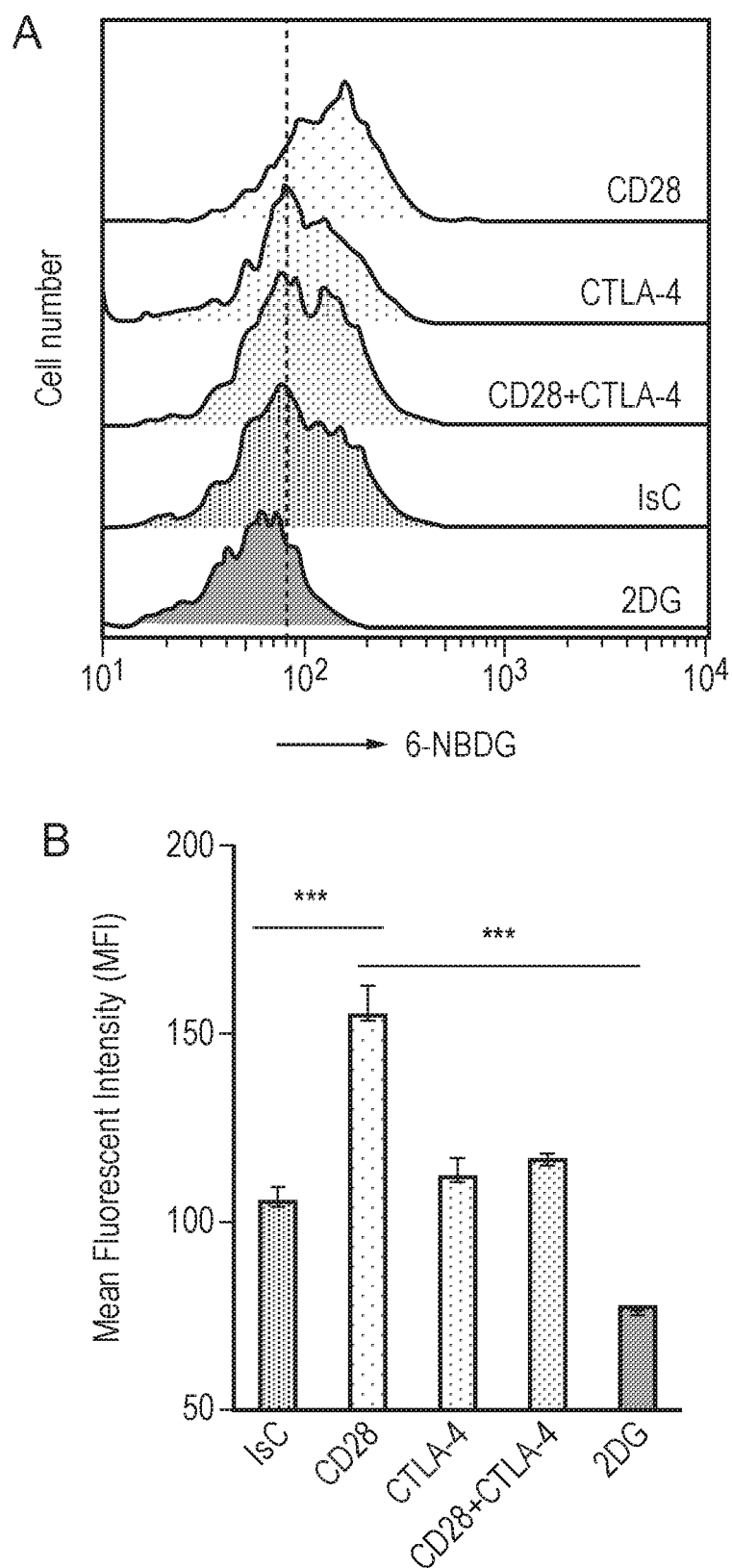

FIG. 11. Treg migration is regulated by co-stimulatory receptors via induction of glycolysis. A-B: Representative histograms of antibody-stimulated Tregs incubated with 6-NBDG for 10 minutes prior to analysis. The non-fluorescent glucose analog 2-DG was used as a negative control. The mean MFI from 3 independent experiments±SD is shown in panel B.

Figure 12:
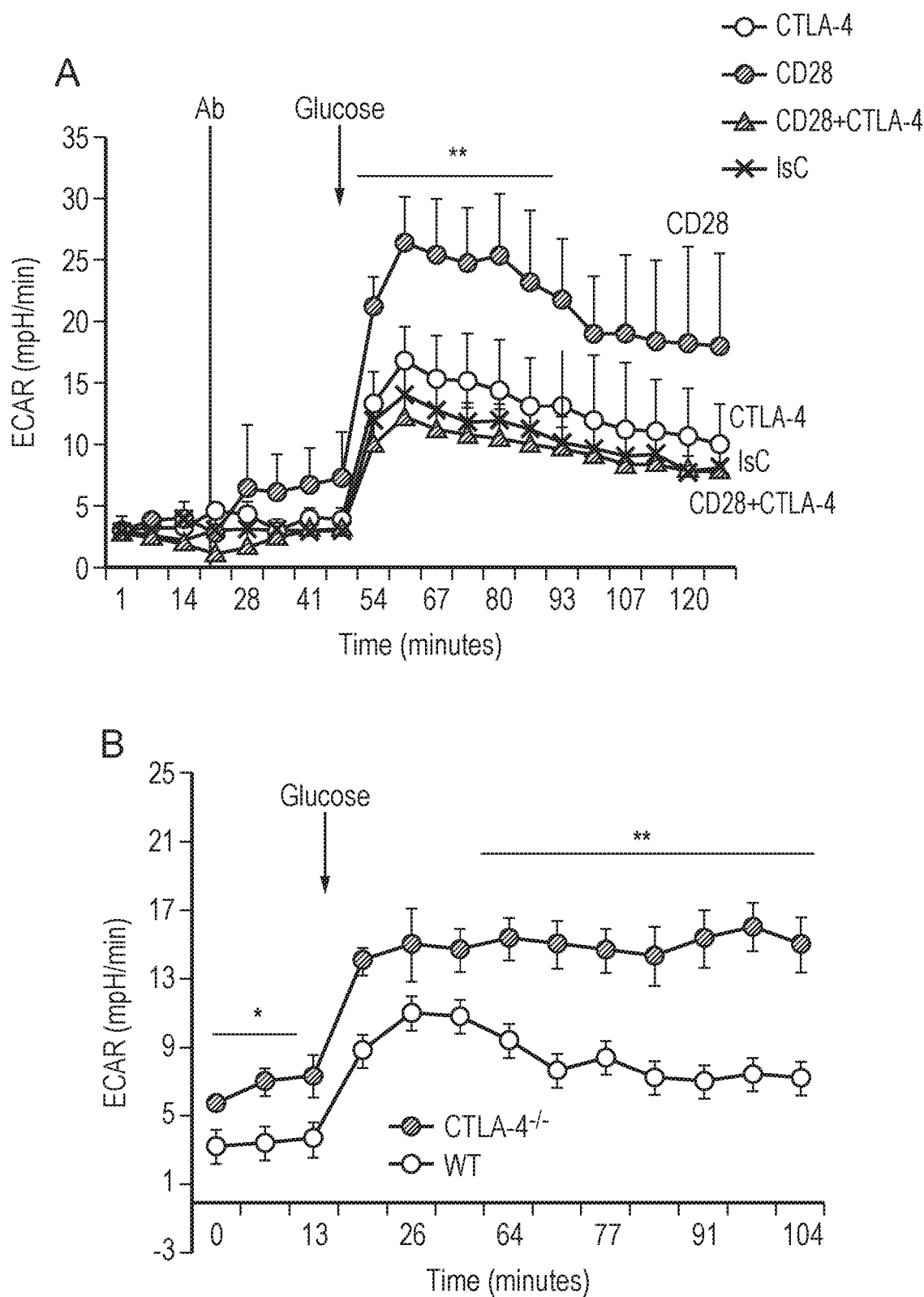

FIG. 12. ECAR of antibody-stimulated Tregs was measured by fluxometry. Antibodies (Ab) and D-glucose were injected at the indicated time points±SD (A). ECAR (±SD) was measured in WT or CTLA-4KO Tregs which were unstimulated (B). D-glucose was injected as indicated by the arrow.

Figure 13:
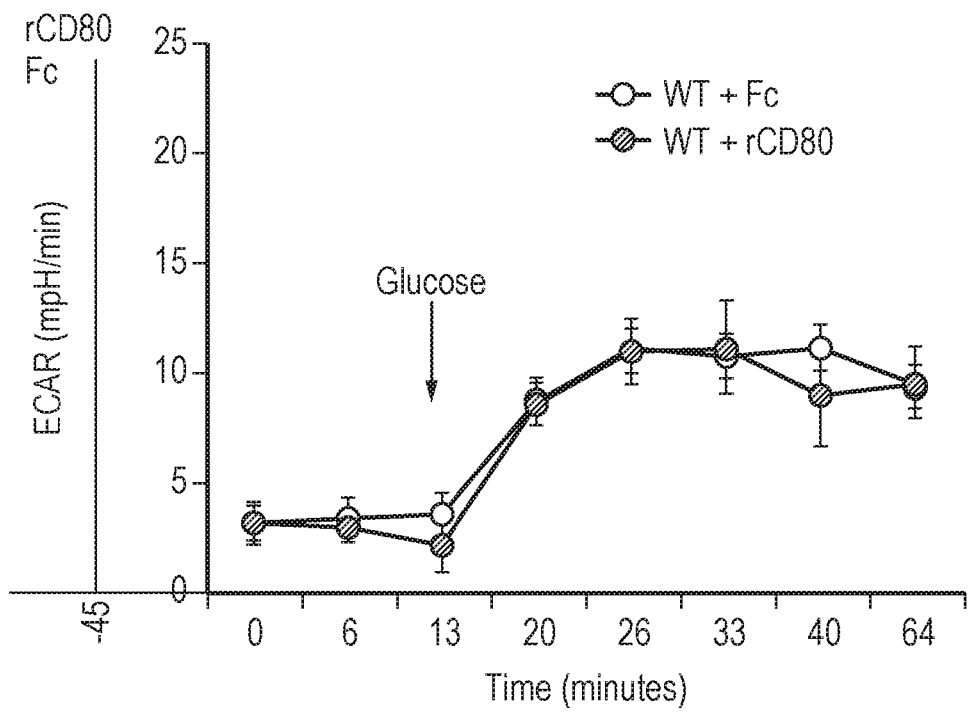
Figure 13:
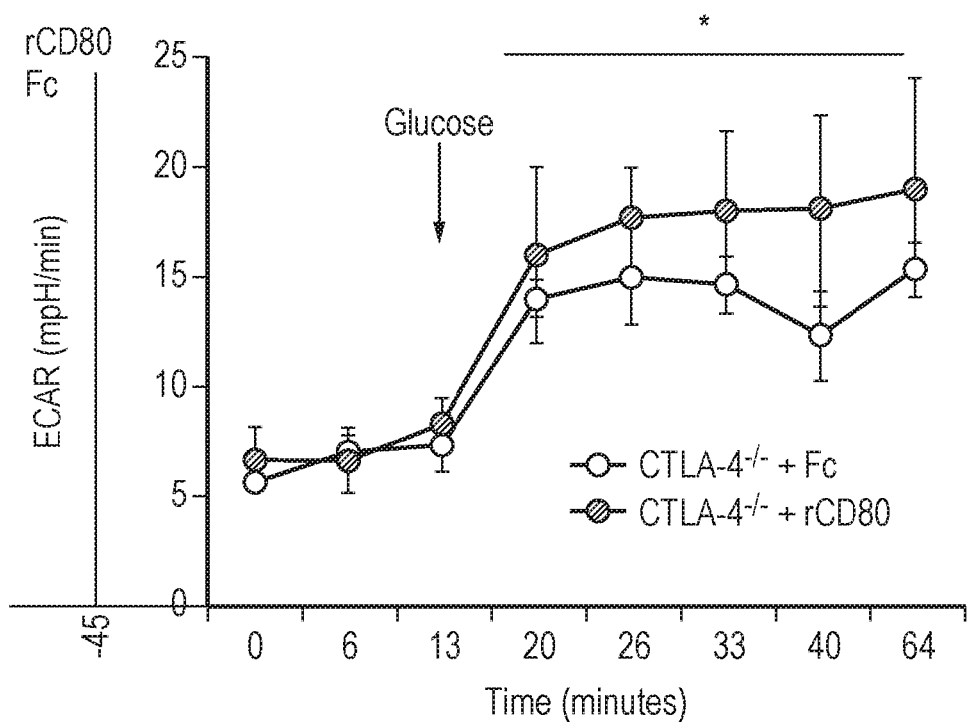

FIG. 13. ECAR (±SD) was measured in WT (A) or CTLA-4KO (B) Tregs which were previously stimulated with recombinant CD80 or Fc fragments for 30 minutes. D-glucose was injected as indicated by the arrow.

Figure 14:
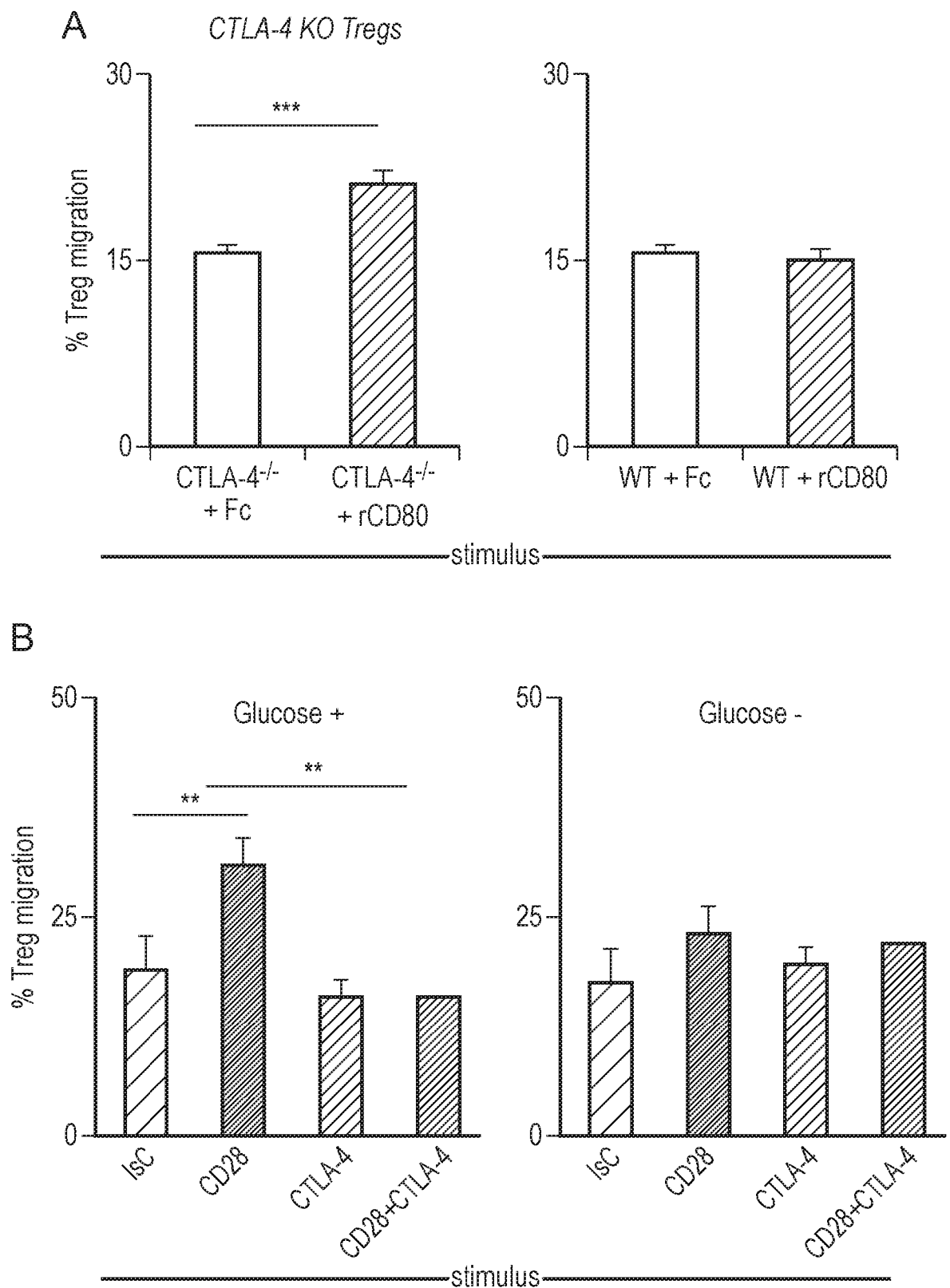

FIG. 14. A: Migration of rCD80- or Fc-stimulated CTLA-4KO and WT Tregs through syngeneic IFN-γ-treated EC monolayers. Results are expressed as mean percentage of migrated cells at 24 hours±SD. n=3, N=4 B: Migration of antibody-stimulated Tregs re-suspended in either glucose-free or glucose-reconstituted medium through IFN-γ-treated syngeneic EC monolayers, expressed as percentage of migrated cells after 24 hours±SD. (n=3, N=4).

Figure 15:
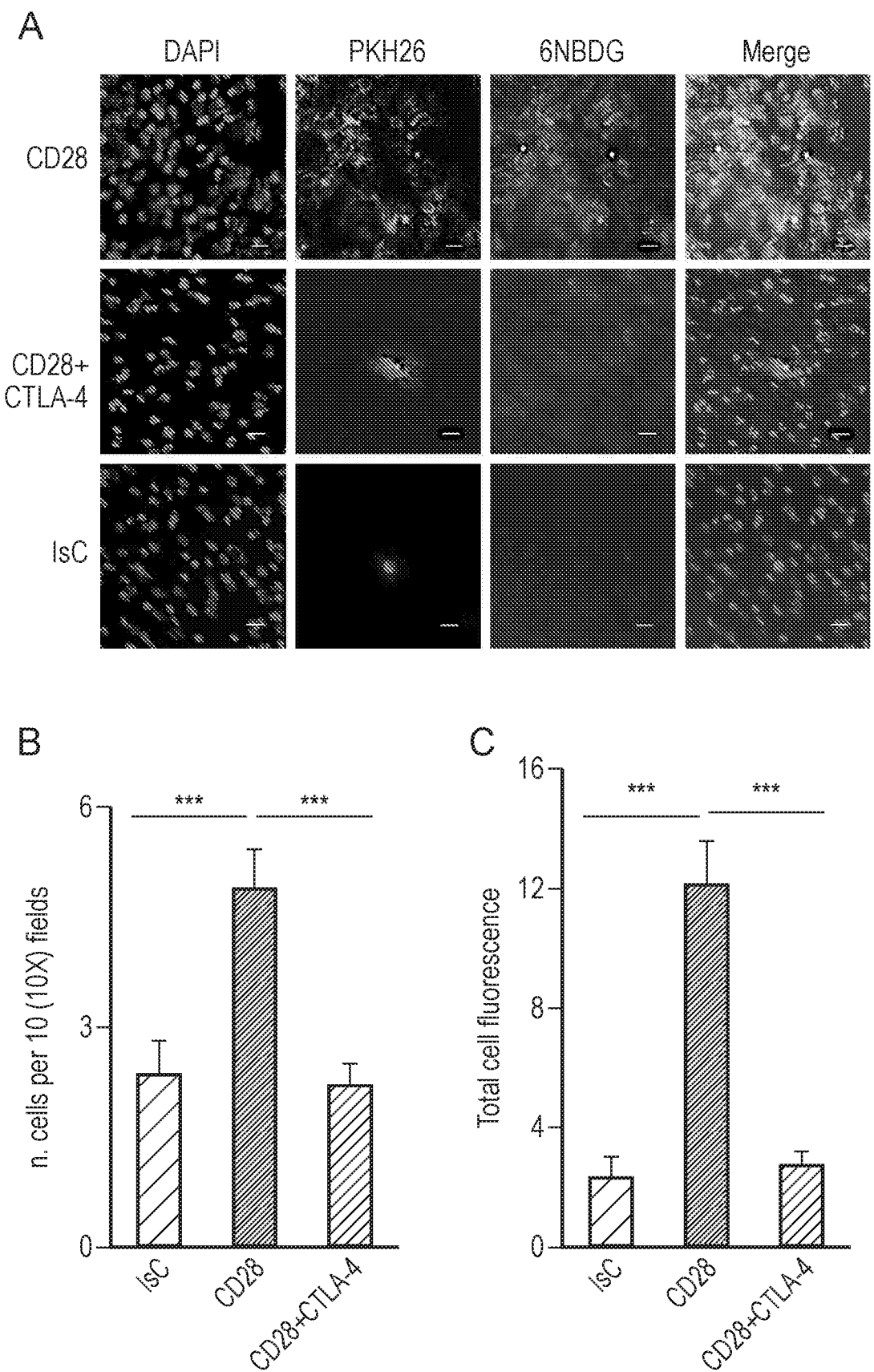

FIG. 15. Antibody-stimulated Tregs labelled with PKH26 (second column) were injected i.p. in C57BL/6 mice given IFN-γ i.p. 48 hours earlier. 6-NBDG (third column) was injected i.p. immediately after. Peritoneal membranes were removed 1 hour later, counterstained with DAPI and imaged by wide-field fluorescence microscopy to determine the number of infiltrating cells and 6-NBDG uptake by the infiltrating cells. Representative images are shown in panel A. The mean number of cells counted in 10 10× fields from 4 recipients±SD and the mean total cell fluorescence of 6-NBDG from 10-12 cells from 3 10× fields±SD are shown in panels B and C, respectively. (n=4, N=2), * p<0.05;  p<0.01; * p<0.005.

Figure 16:
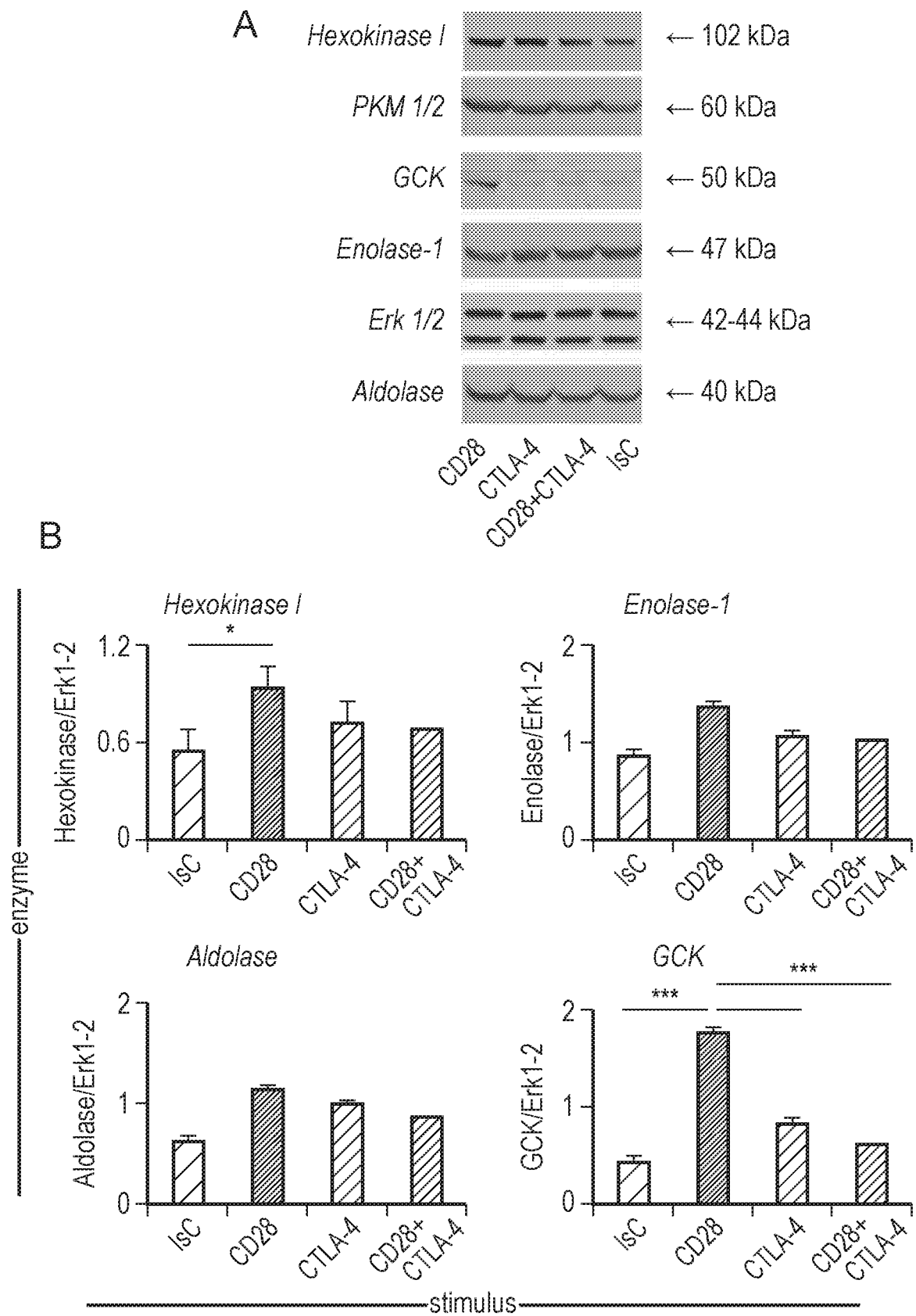

FIG. 16. Pro-migratory stimuli induce metabolic reprogramming of Tregs. A-B: Expression of the indicated enzymes in Tregs was measured 4 hours after antibody stimulation by western blotting. In panel B the mean relative expression measured by densitometric analysis in 3 independent experiments±SD is shown.

Figure 17:
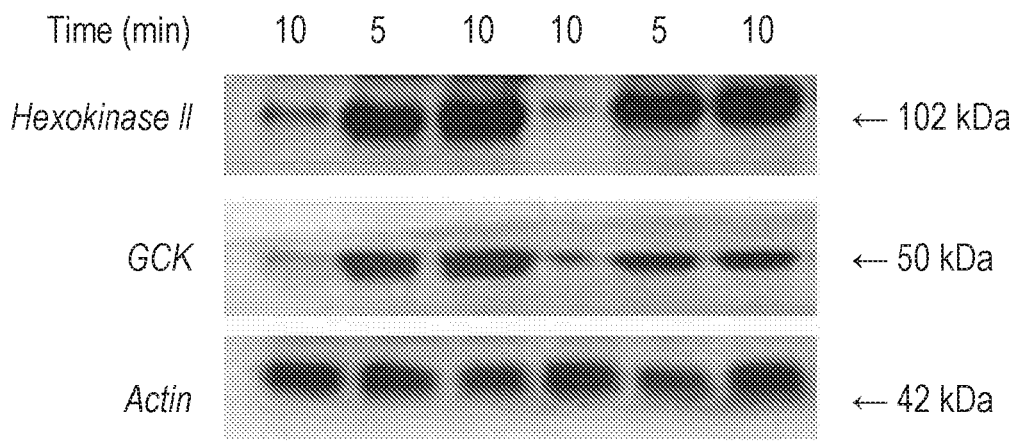
Figure 17:
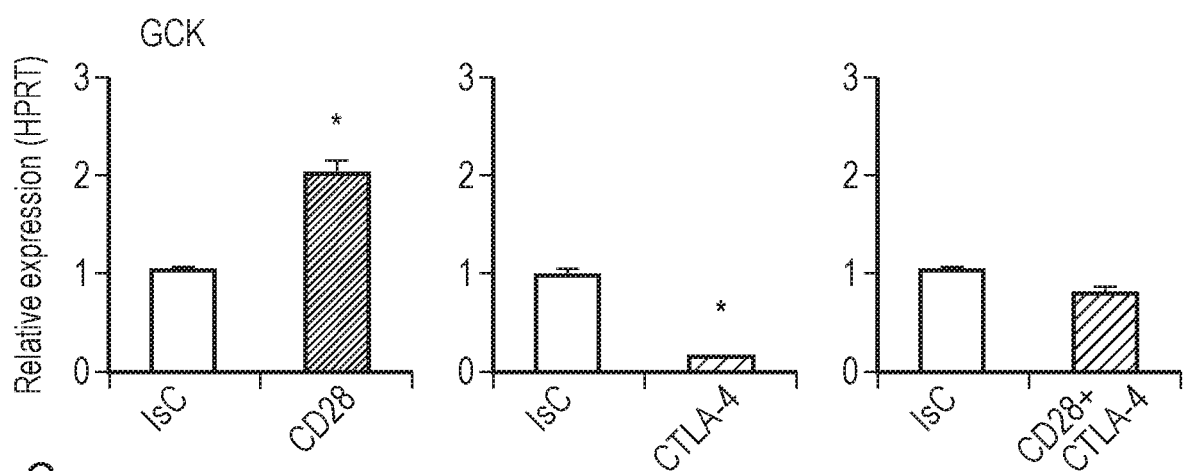
Figure 17:
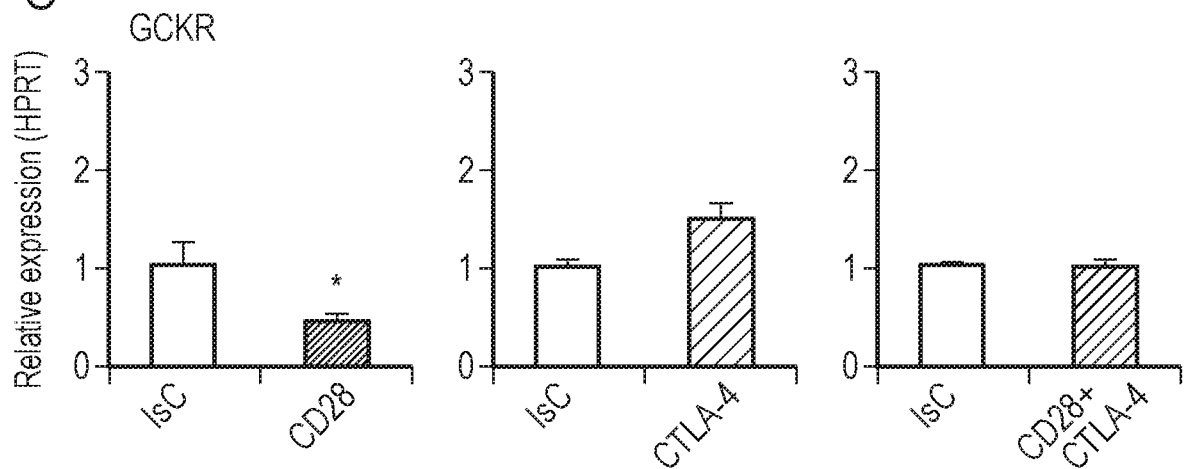

FIG. 17. A: Expression of the indicated enzymes by CD28- or LFA-1-stimulated Tregs measured by western blotting at the indicated time points. B-C: Relative mRNA expression levels of GCK (B) and GCKR (C) by antibody-stimulated Tregs was measured by RT-PCR. GCKR=Glucokinase regulatory protein; binds GCK and blocks enzymatic activity.

Figure 18:
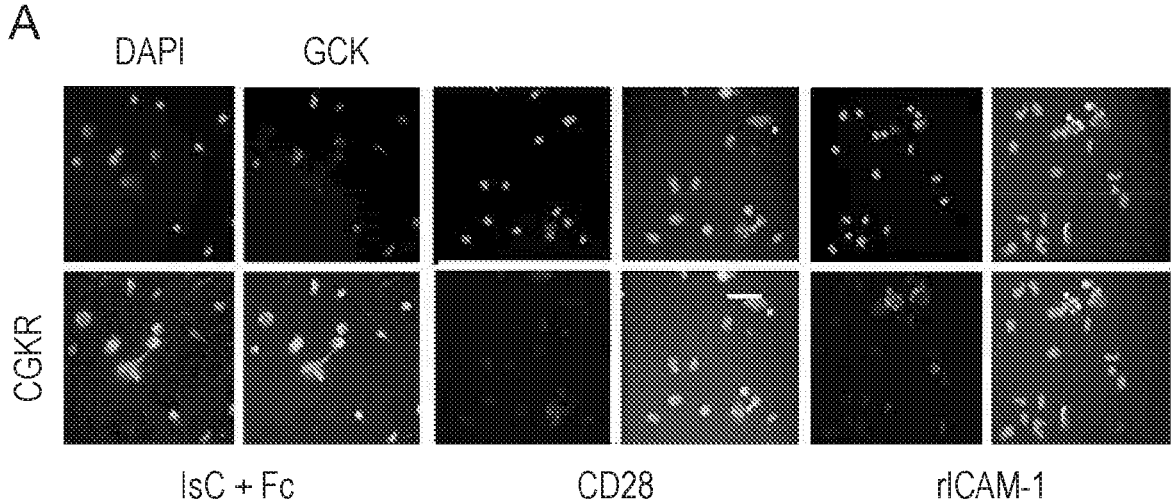
Figure 18:
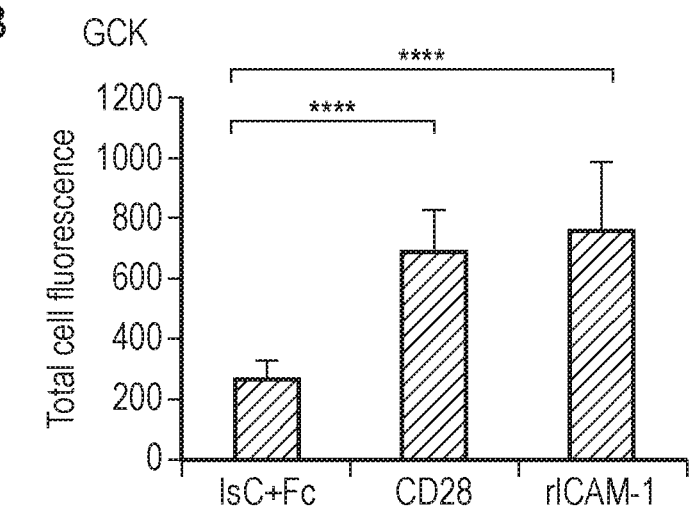
Figure 18:
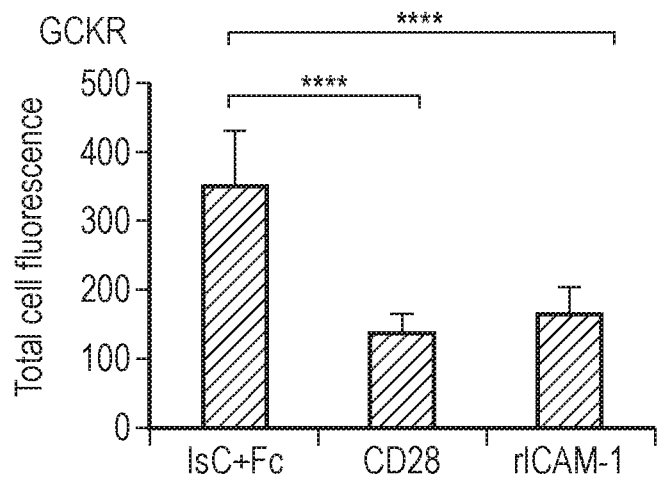

FIG. 18. A-B: Expression of the indicated enzymes by CD28- or LFA-1-stimulated Tregs measured by confocal microscopy at the indicated time points. Cellular protein expression by antibody-stimulated Tregs was measured by confocal microscopy. In panel B the mean MFI±SEM measured using Image J software is shown. N=3. Scale bar 20 μm.

Figure 19:
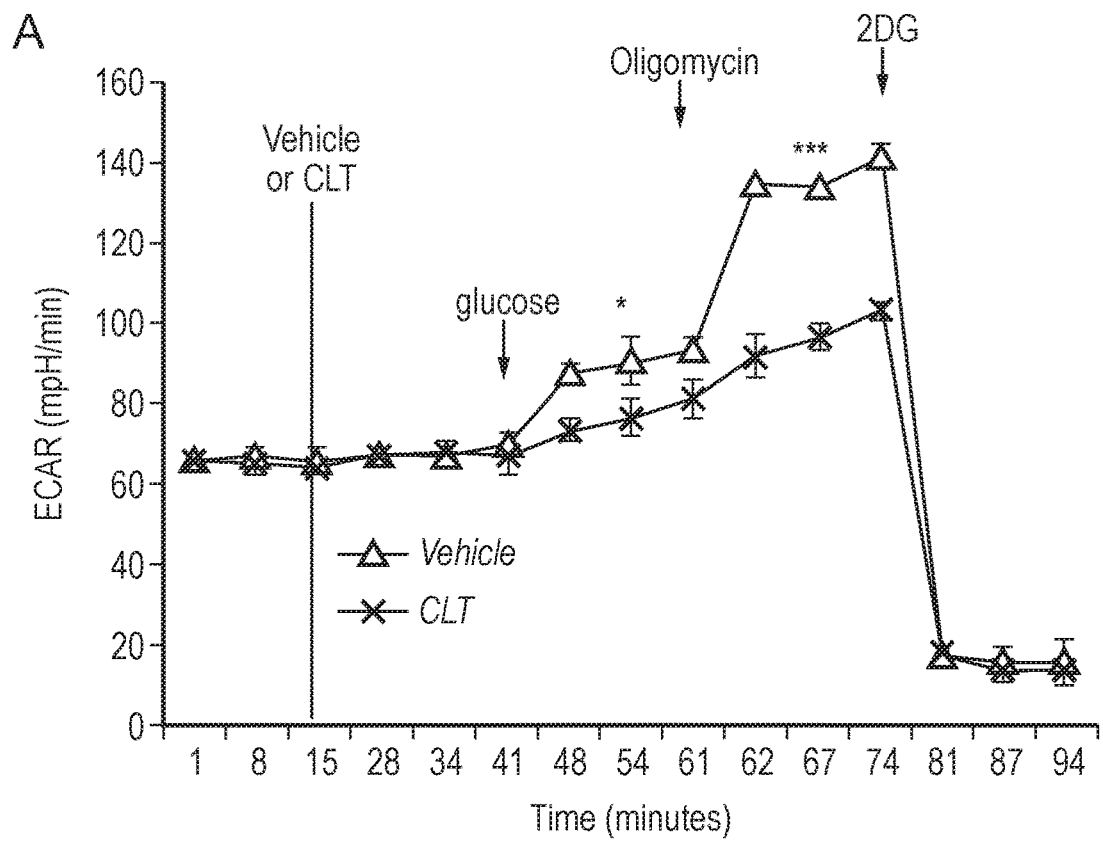
Figure 19:
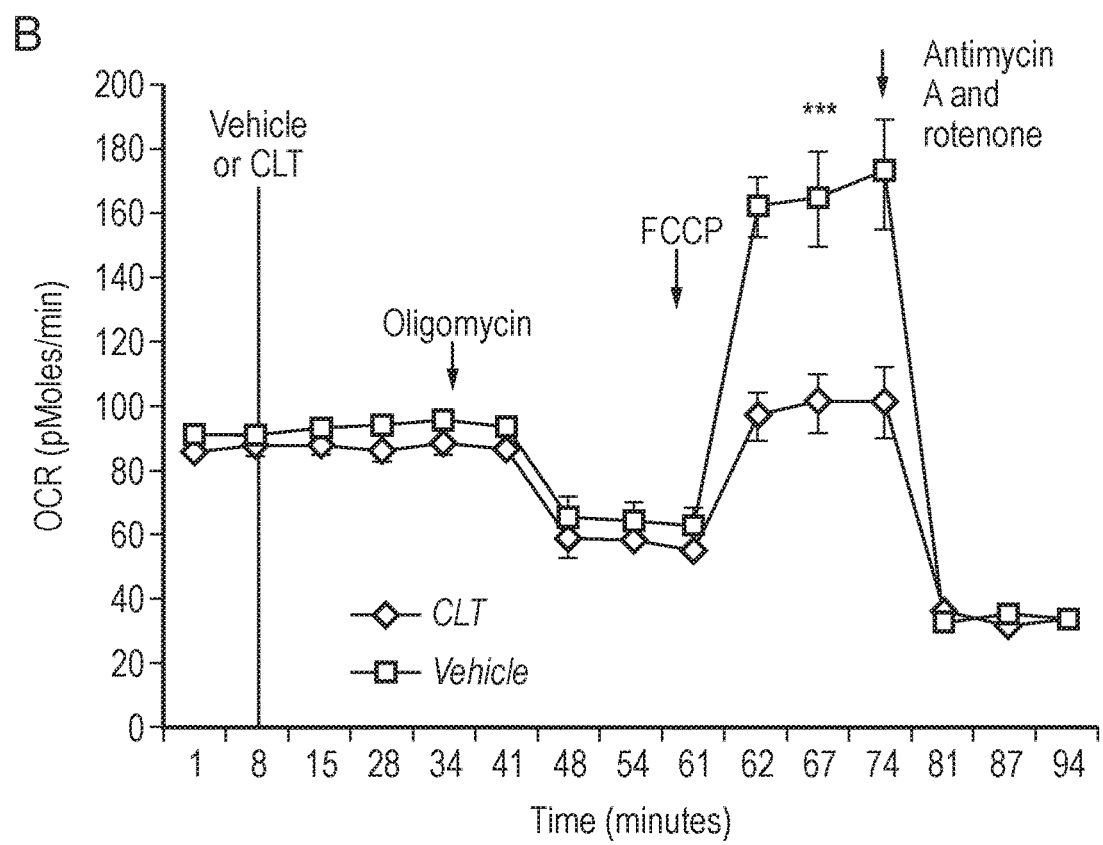

FIG. 19. Real time analysis of the ECAR and OCR of CD4+ T cells stimulated for 24 hours with anti-CD3 plus anti-CD28 antibodies was performed using fluxometry. Wells were injected first with CLT or Vehicle. A second injection followed at the time point indicated (dashed line) introducing D-glucose into the wells. Subsequently, modulators of glycolysis (A) or cellular respiration (B) were sequentially injected at the indicated time points. (N=2), p<0.01, *p<0.005. OCR=Oxygen Consumption Rate: indirect measure of mitochondrial respiration and fatty acid oxidation (FAO).

Figure 20:
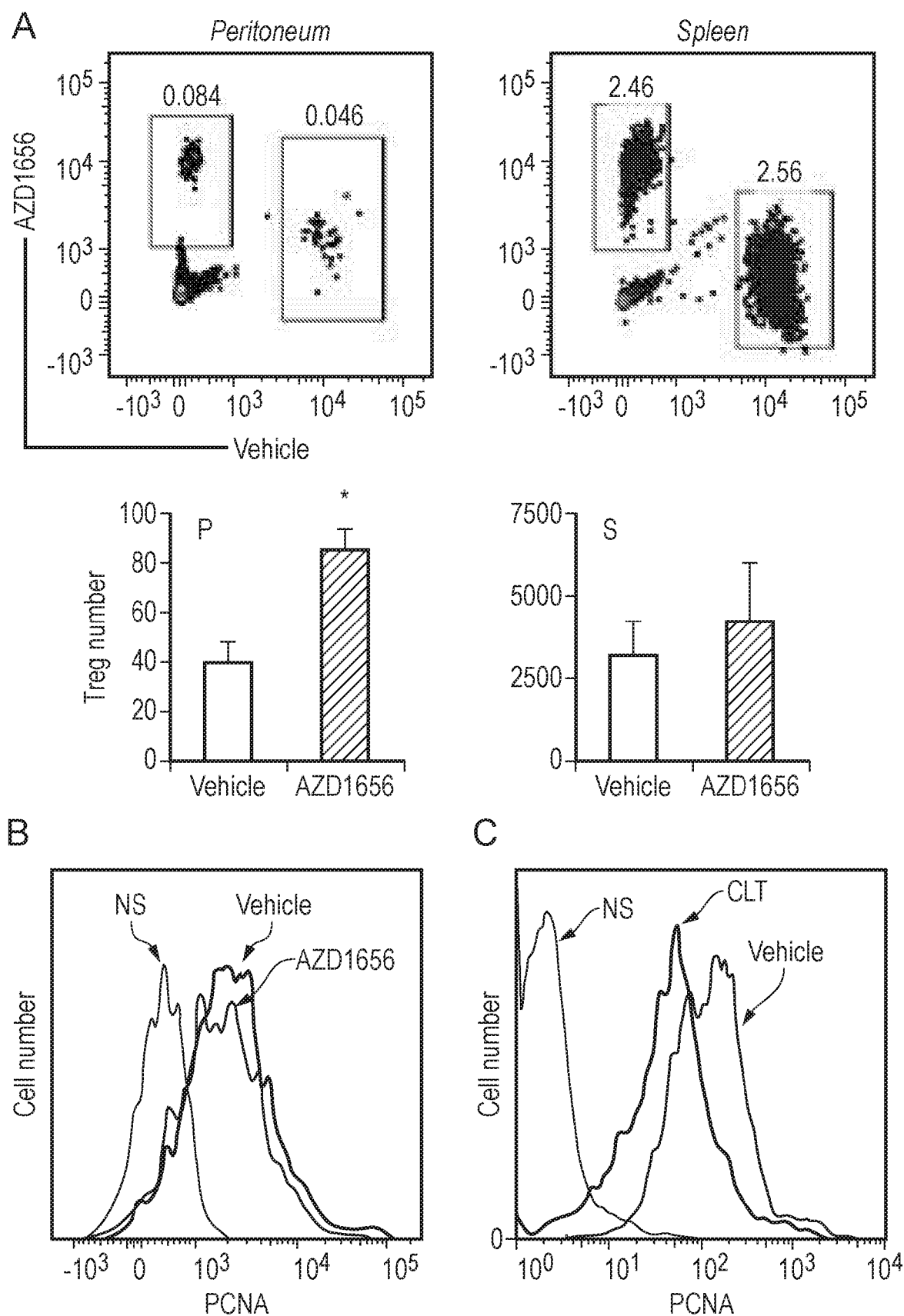

FIG. 20. A: AZD1656 (GCK activator, 1 μM) and vehicle-treated Tregs (2 hours in insulin-free medium) were labeled with different intravital fluorescent dyes, and co-injected into syngeneic recipients that had received IFN-γ i.p. 48 hours earlier. Cells were recovered from the peritoneum or spleen after 24 hours and analyzed by flow cytometry. Representative dot plots are shown. The bar graphs indicate mean absolute number of labeled cells retrieved±SD (n=4 N=2). B-C: expression of PCNA by Tregs stimulated with allogeneic DCs following treatment with either AZD1656 (B) or Clotrimazole (CLT, 1 μM, 2 hours, C) or vehicle alone was measured by flow cytometry. NS, non-stimulated control Tregs. Representative histograms are shown. (n=3, N=3).

Figure 21:
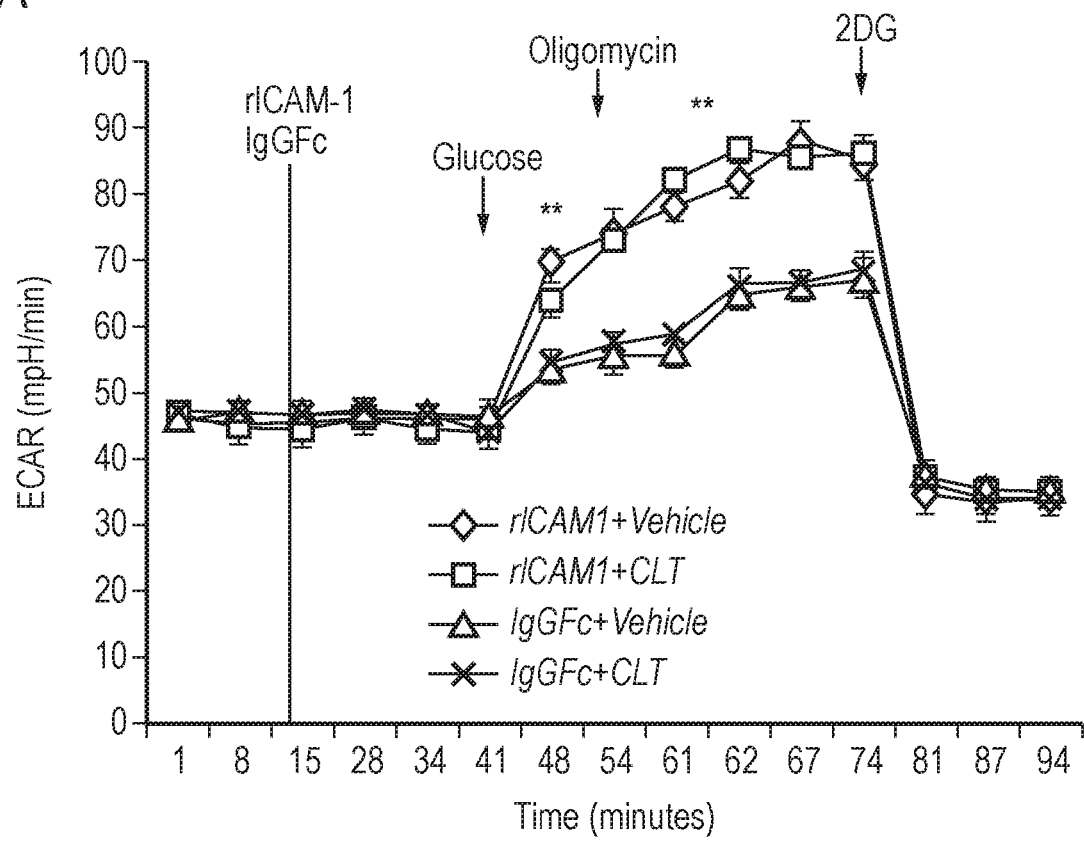
Figure 21:
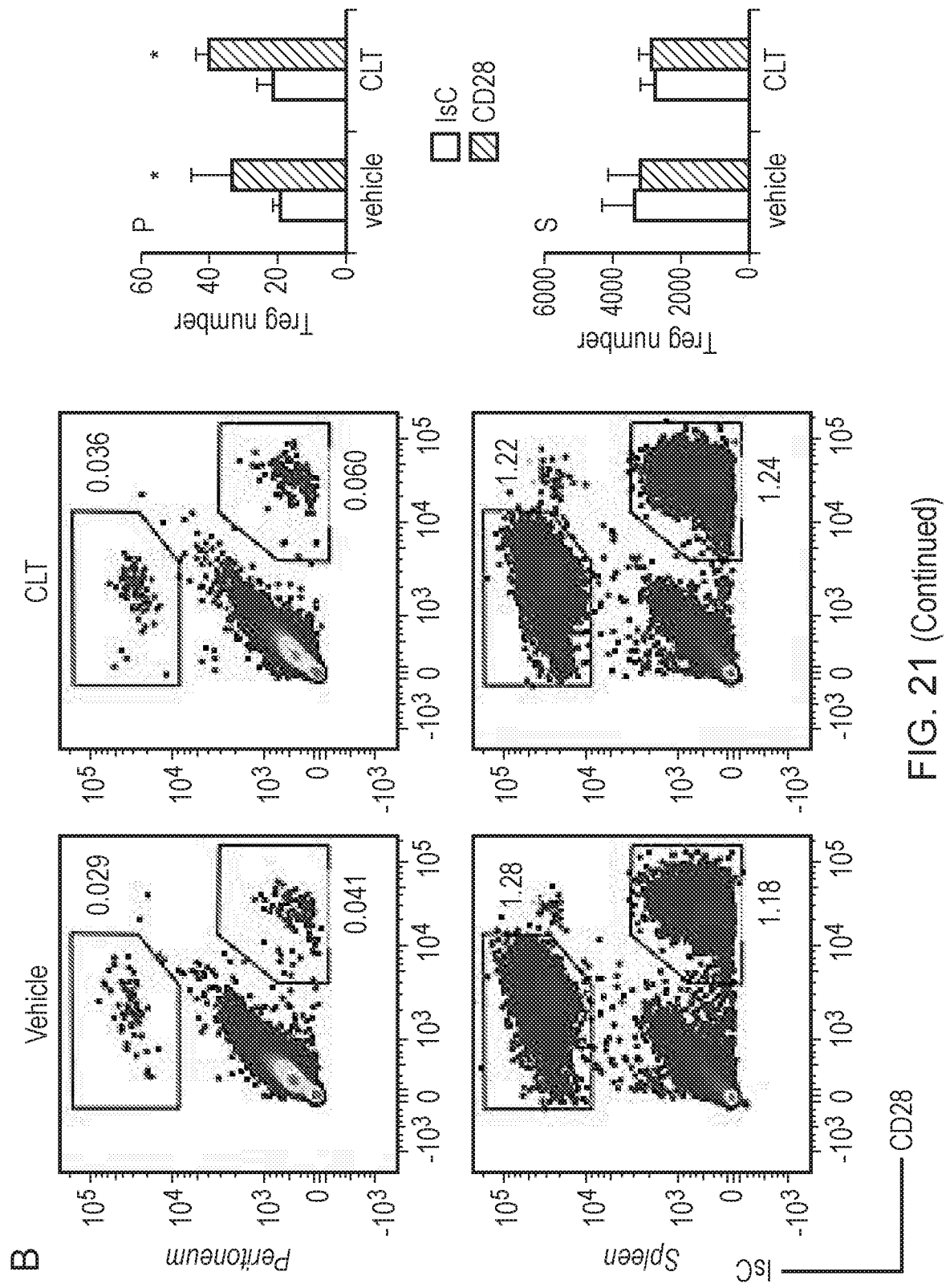

FIG. 21. A: ECAR of Treg cells activated with recombinant ICAM-1 or Fc control. CLT or vehicle, as well as other glycolysis-affecting drugs were added as indicated. B: CLT- or vehicle-treated Tregs underwent CD28 or isotype-matched antibody-stimulation, labelled with different intravital fluorescent dyes and injected i.v. in syngeneic recipients that had received IFN-γ i.p. 48 hours earlier. Cells were recovered from the peritoneum (P) or spleen (S) after 24 hours and analyzed by flow cytometry. Representative dot plots are shown. The column graphs indicate mean absolute number of labeled cells retrieved±SD (n=3 N=2). * p<0.05 *p<0.005; **p<0.001.

Figure 22:
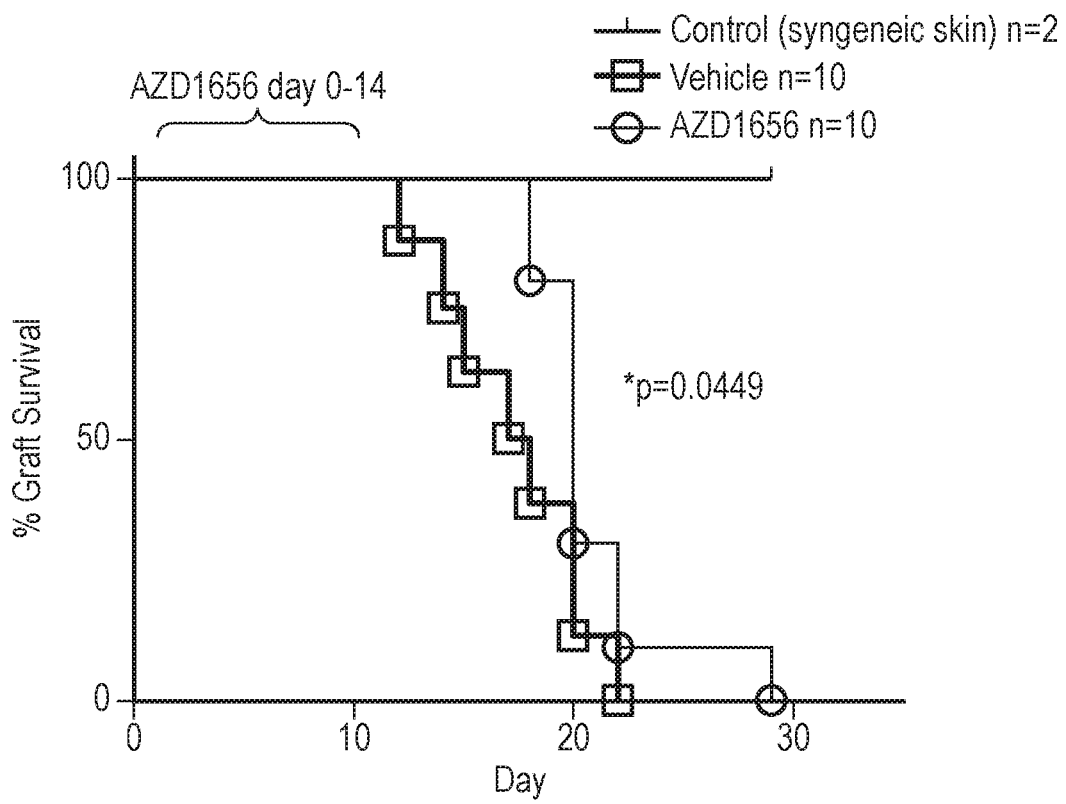

FIG. 22. Pharmacological activation of GCK significantly delays skin allograft rejection. C57B16 mice received a B6Kd skin graft or syngeneic skin as a control. Some recipients were treated with the GCK activator AZD1656 (20 mg/kg daily) for 2 weeks after transplantation. N=9.

Figure 23:
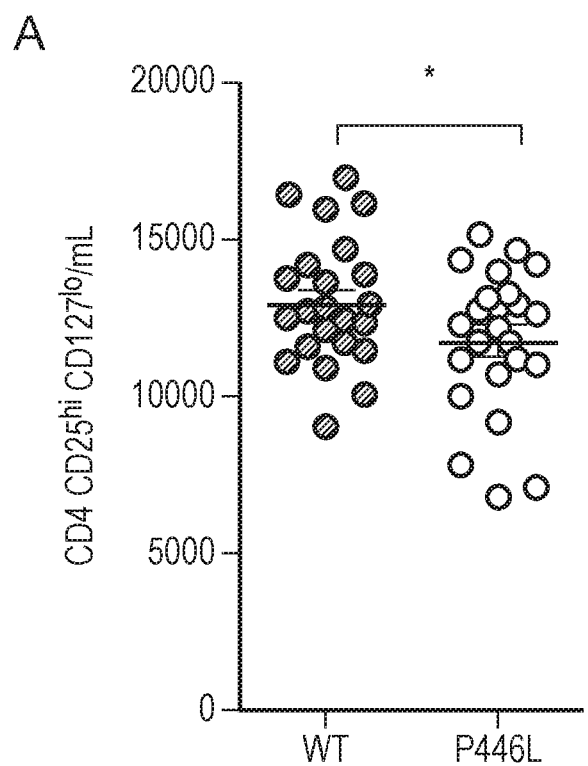
Figure 23:
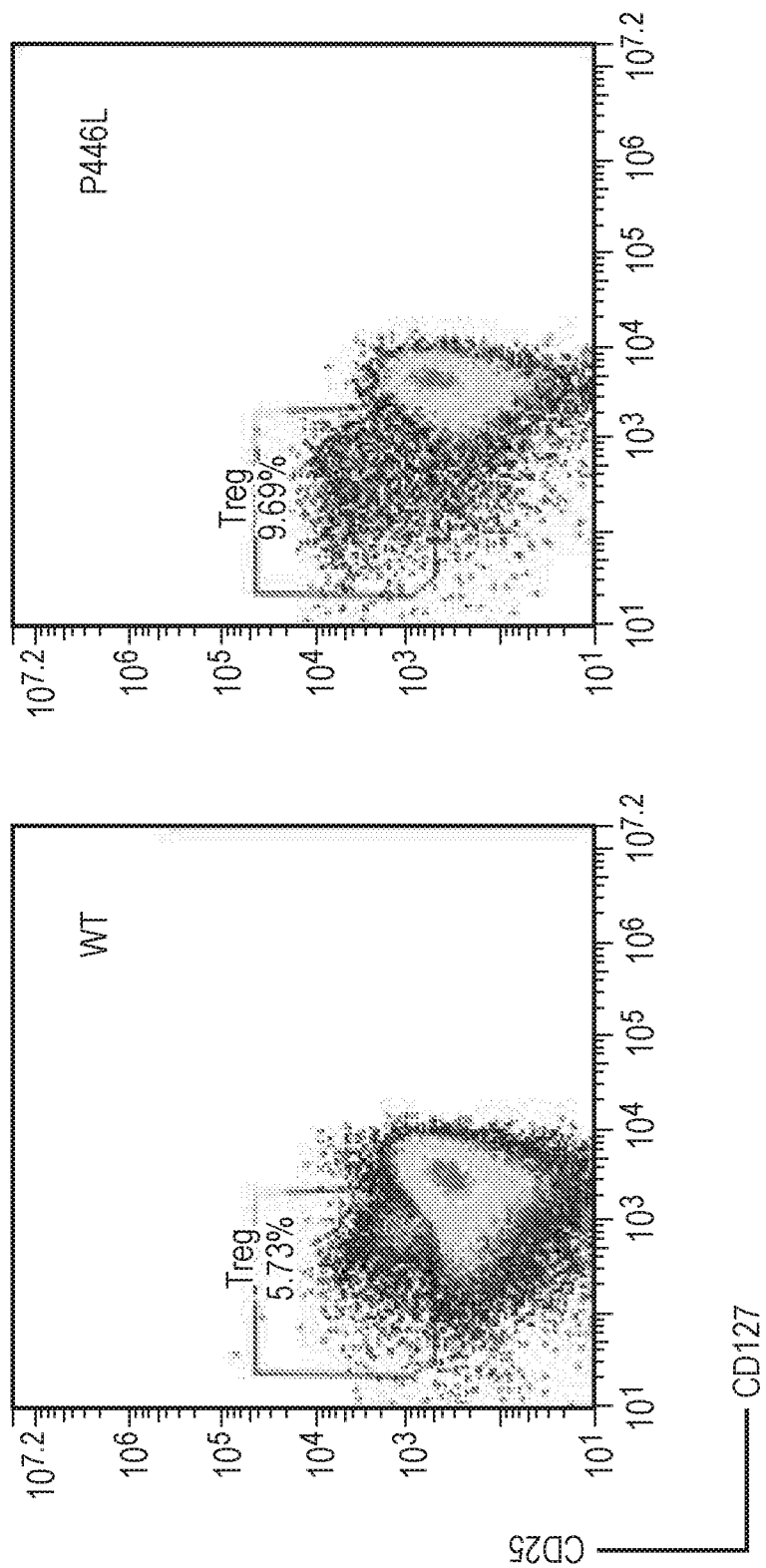

FIG. 23. Treg cells bearing a loss-of function GCKR allele display enhanced motility. A: Cell number/mL of Tregs (CD4+CD25highCD127low) in carriers of the allele P446L compared to individuals carrying the WT allele (P446). Representative dot plots are shown in panel B. n=25. CD4+ lymphocyte subpopulations, defined as Naive (CD45RA+), Central memory (CD45RO+, CD62L+, CCR7+) and Effector memory (CD45RO+, CD62L-, CCR7-) in the two study populations are shown in panels.

Figure 24:
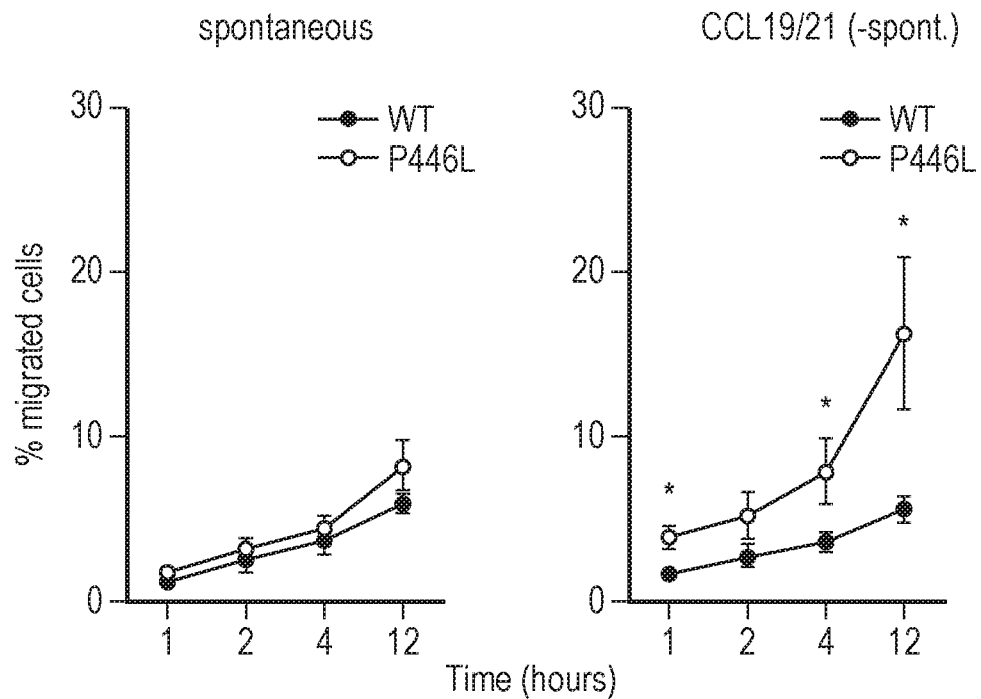
Figure 24:
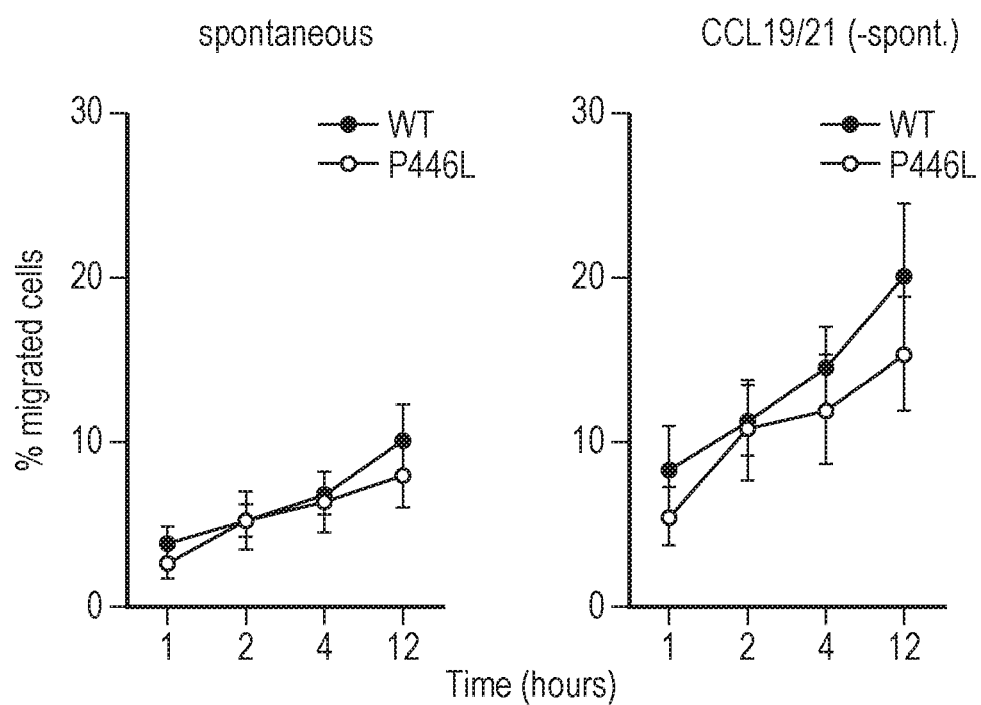

FIG. 24. Migratory responses of Treg (A) and Tconv (B) from 8 P446L-GCKR carriers or WT-GCKR individuals to the chemokines CCL19/21 were measured by transwell.

Figure 25:
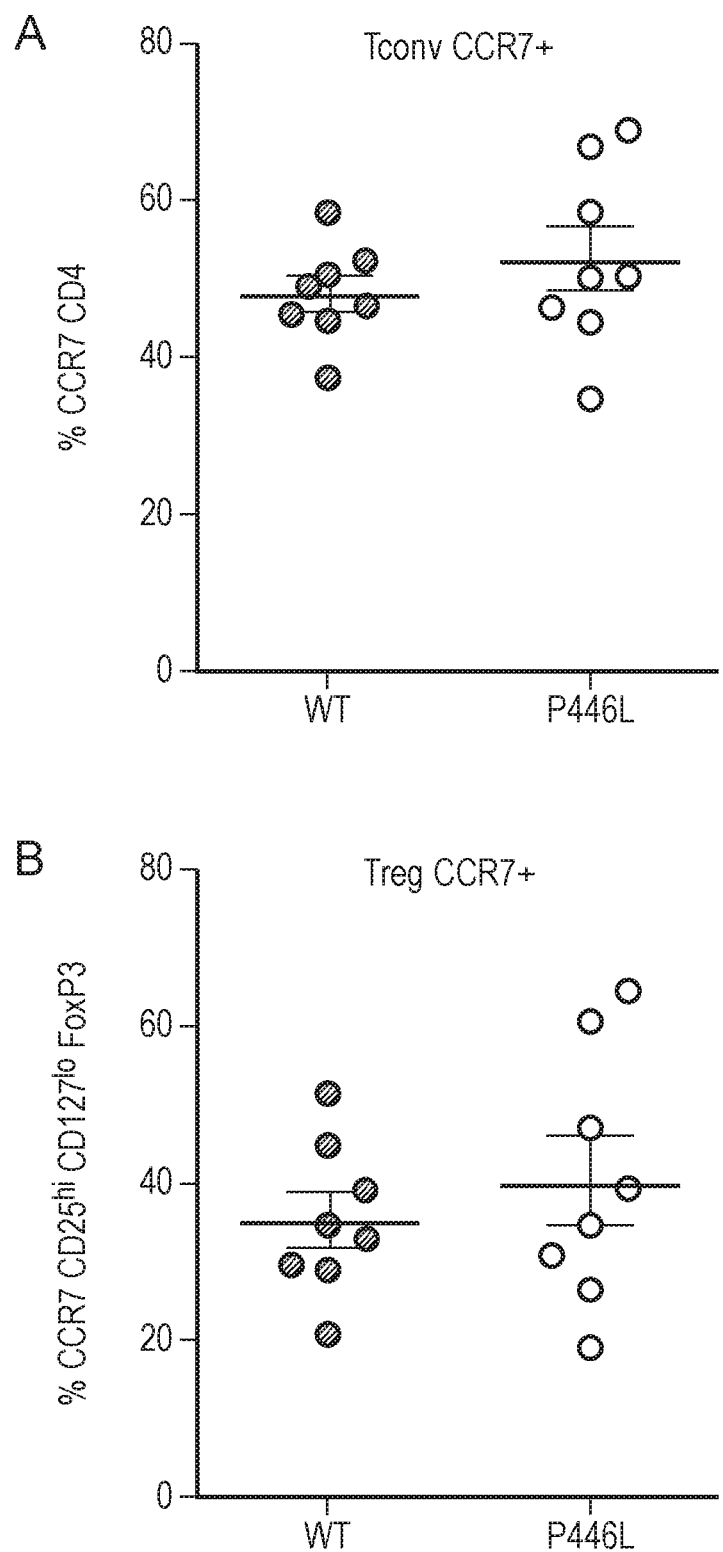

FIG. 25. In panels A-B, the percentage of T cells expressing CCR7, receptor for the chemokines CCL19/21 used in the migration assays in FIG. 24, from P446L-GCKR carriers (n=8) and WT-GCKR (n=8) subjects are shown, * p<0.05.

SUMMARY OF THE INVENTION

Migration of activated regulatory T-cells (Treg) to inflamed tissue is crucial for their immune-modulatory function. While metabolic reprogramming during Treg differentiation has been extensively studied, the bioenergetics of Treg trafficking remains undefined. The present inventors have investigated the metabolic demands of migrating Tregs in vitro and in vivo.

By comparing LFA-1- and CD28-mediated pro-migratory signals as a working model, the present inventors have investigated the bioenergetics of migrating Treg cells in vitro and in vivo. Accordingly, the present inventors define herein a novel, specific pathway of metabolic reprogramming engaged during Treg migration both in mice and humans.

The present inventors have found that glycolysis is instrumental for Treg migration and is initiated by pro-migratory stimuli culminating in induction of the enzyme glucokinase (GCK). Subsequently, GCK promotes cytoskeletal rearrangements by associating with actin. Tregs lacking this pathway are functionally suppressive but fail to migrate to skin allografts and inhibit rejection. Similarly, human carriers of a loss-of-function mutation in the GCK regulatory protein gene—leading to increased GCK activity—have decreased numbers of circulating activated Tregs. These Tregs display enhanced migratory activity but similar suppressive function, while conventional T-cells are unaffected. Thus, GCK-dependent glycolysis regulates Treg migration. As such, the present invention relates to the activation of glycolysis in Tregs in order to treat or prevent diseases and medical conditions, in particular those which are immune mediated.

Accordingly, in one aspect the present invention provides a glycolysis-activating agent for use in the treatment or prevention of a disease or medical condition, which treatment or prevention is mediated via the trafficking of endogenous regulatory T cells (Tregs).

In another aspect, the present invention provides a glycolysis-activating agent for use in the trafficking of endogenous regulatory T cells (Tregs) in a subject suffering from or at risk of suffering from a disease or medical condition.

In another aspect, the present invention provides a glycolysis-activating agent for use in the treatment or prevention of a disease or medical condition that is alleviated by the trafficking of endogenous regulatory T cells (Tregs) to a tissue or organ.

In another aspect, the present invention provides a glycolysis-activating agent for use in modulating the immune response in a subject.

In another aspect, the present invention provides a pharmaceutical composition comprising a glycolysis-activating agent for use as described herein and a pharmaceutically acceptable carrier, vehicle, diluent or excipient.

In another aspect, the present invention provides a method of treating or preventing an immune mediated disease or condition in a subject, said method comprising administering a glycolysis-activating agent to the subject.

In yet another aspect, the present invention provides a method of modulating the immune response in a subject, said method comprising administering a glycolysis-activating agent to the subject.

DETAILED DESCRIPTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

Glycolysis-Activating Agent

In the context of the present invention, a "glycolysis-activating agent" is any agent or compound which is capable of activating, stimulating, inducing, catalysing or increasing the rate of the biochemical process of glycolysis in a cell. The agent or compound may be, for example, biological or chemical in nature, e.g. a small molecule or antibody. The agent or compound may target the process of glycolysis directly or indirectly, for example, or it may act directly on one or more of the enzymes involved in the glycolytic pathway.

One such enzyme involved in the process of glycolysis is glucokinase (GCK, GLK or GK). Accordingly, in one embodiment, the glycolysis-activating agent of the present invention is a GCK-activating agent (also known as a glucokinase activator or GKA). In one embodiment, the GKA prevents or inhibits the interaction between GCK and GCK regulatory protein (GCKR).

Methods and assays for determining the activity of enzymes such as GCK are well-known to the person skilled in the art. For example, a particular assay for measuring GCK activity is described in WO2008050101, in which enzymatic activity of recombinant GCK is measured by incubating GCK with ATP and glucose. The rate of product formation may be determined by coupling the assay to a G6P dehydrogenase, NADP/NADPH system and measuring the linear increase with time of optical density at 340 nm.

A number of GCK activators are known in the art and are described in the references cited herein.

In one embodiment of the present invention, the GCK-activating agent is a compound of the formula (I) or a pharmaceutically acceptable salt thereof:

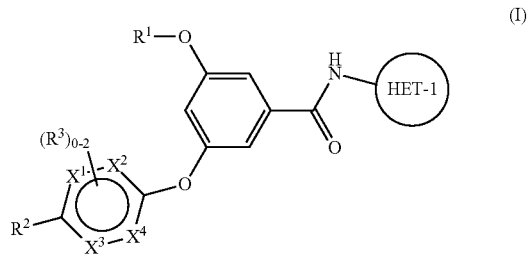

wherein:
$R^1$ is selected from isopropyl, but-2-yl, cyclopentyl, 1,1,1-trifluoroprop-2-yl, 1,3-difluoroprop-2-yl, but-1-yn-3-yl, 1-hydroxyprop-2-yl, 2-hydroxybut-3-yl, 1-hydroxybut-2-yl, tetrahydrofuryl, tetrahydropyranyl, 1-methoxyprop-2-yl, 1-methoxybut-2-yl, 2-hydroxyprop-1-yl, 2-methoxyprop-1-yl, 2-hydroxybut-1-yl, 2-methoxybut-1-yl, 1-fluoromethoxyprop-2-yl, 1,1-difluoromethoxyprop-2-yl and 1-trifluoromethoxyprop-2-yl;

HET-1 is a 5- or 6-membered, C-linked heteroaryl ring containing a nitrogen atom in the 2-position and optionally 1 or 2 further ring heteroatoms independently selected from O, N and S; which ring is optionally substituted on any nitrogen atom (provided it is not thereby quaternised) by a substituent selected from $R^7$ and/or on 1 or 2 available carbon atoms by a substituent independently selected from $R^6$;

$R^2$ is selected from —C(O)NR$^4$R$^5$ and —SO$_2$NR$^4$R$^5$;

$R^3$ is selected from methyl, trifluoromethyl and halo;

$R^4$ and $R^5$ together with the nitrogen atom to which they are attached form a 4 to 7 membered saturated or partially unsaturated heterocyclyl ring, optionally containing 1 or 2 further heteroatoms (in addition to the linking N atom) independently selected from O, N and S, wherein a —CH₂— group can optionally be replaced by a —C(O)— and wherein a sulphur atom in the ring may optionally be oxidised to a S(O) or S(O)₂ group; which ring is optionally substituted on an available carbon atom by 1 or 2 substituents independently selected from $R^8$ and/or on an available nitrogen atom by a substituent selected from $R^9$; or $R^4$ and $R^5$ together with the nitrogen atom to which they are attached form a 6-10 membered bicyclic saturated or partially unsaturated heterocyclyl ring, optionally containing 1 further nitrogen atom (in addition to the linking N atom), wherein a —CH2— group can optionally be replaced by a —C(O)—; which ring is optionally substituted on an available carbon by 1 substituent selected from hydroxy and $R^3$ or on an available nitrogen atom by methyl;

$R^6$ is independently selected from (1-4C)alkyl, halo, hydroxy(l-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl and di(1-4C)alkylamino(1-4C)alkyl;

$R^7$ is independently selected from (1-4C)alkyl, halo(1-4C)alkyl, dihalo(1-4C)alkyl, trihalo(1-4C)alkyl, hydroxy(1-4C)alkyl, (1-4C)alkoxy(1-4C)alkyl, (1-4C)alkylS(0)p(1-4C)alkyl, amino(1-4C)alkyl, (1-4C)alkylamino(1-4C)alkyl and di(1-4C)alkylamino(1-4C)alkyl;

$R^8$ is selected from hydroxy, (1-4C)alkoxy, (1-4C)alkyl, aminocarbonyl, (1-4C)alkylaminocarbonyl, di(1-4C)alkylaminocarbonyl, (1-4C)alkylamino, di(1-4C)alkylamino, (1-4C)alkoxy(1-4C)alkyl, hydroxy(1-4C)alkyl and —S(O)p(1-4C)alkyl;

$R^9$ is selected from (1-4C)alkyl, —C(O)(1-4C)alkyl, aminocarbonyl, (1-4C)alkylaminocarbonyl, di(1-4C)alkylaminocarbonyl, (1-4C)alkoxy(1-4C)alkyl, hydroxy(1-4C)alkyl and —S(O)p(1-4C)alkyl;

wherein each of $X^1$, $X^2$ and $X^3$ is independently selected from CH, N, S and O; $X^4$ is absent (to make a 5-membered ring) or is selected from CH, N, O and S; provided that at least one of $X^1$, $X^2$, $X^3$ and $X^4$ is CH and provided that there are no O—O, O—S or S—S bonds within the ring.

In one embodiment of the present invention, the GCK-activating agent is selected from the group consisting of: AZD1656, piragliatin (a.k.a. R1440 or R04389620), AZD6370, GKA 50, YH-GKA, PSN-010, LY2121260, ganoderan B, eupatilin, glucolipsin A, glucolipsin B, sinogliatin, GKM-001, TTP-399, SY-004, TMG-123, albiglutide, AM-9514, AMG-0696, AMG-1694, AMG-3969, LCZ-960, AZD-1092, AZD-5658, ARRY-403, BMS-820132, GKM-002, LY-2608204, MK-0941, R-1511, RO-281675, ZYGK-1, OP-286 CR, CM-3, DS-7309, LY-2599506, PF-04937319, PF-04991532, TAK-329, and pharmaceutically acceptable salts thereof.

Piragliatin has the following structural formula:

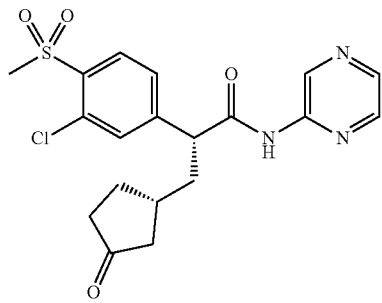 [SMILES: CS(=O)(=O)c1ccc([C@@H](C[C@H]2CCC(=O)C2)C(=O)Nc2cnccn2)cc1Cl]

and is known by the chemical name (2R)-2-(3-chloro-4-methylsulfonylphenyl)-3-[(1R)-3-oxocyclopentyl]-N-pyrazin-2-ylpropanamide.

AZD1656 has the following structural formula:

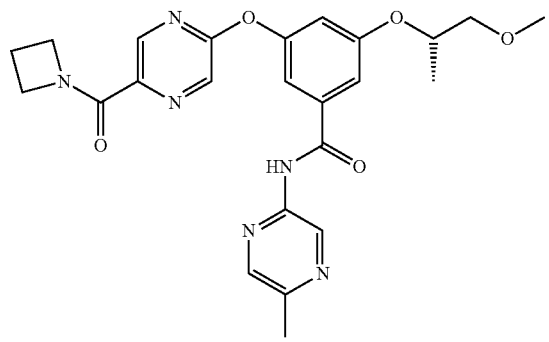

and is known by the chemical name 3-[5-(azetidine-1-carbonyl)pyrazin-2-yl]oxy-5-[(2S)-1-methoxypropan-2-yl]oxy-N-(5-methylpyrazin-2-yl)benzamide.

In one embodiment of the present invention, the GCK-activating agent is 3-{[5-(azetidin-1-ylcarbonyl)pyrazin-2-yl]oxy}-5-{[(1S)-1-methyl-2-(methyloxy)ethyl]oxy}-N-(5 methylpyrazin-2-yl)benzamide.

AZD6370 has the following structural formula:

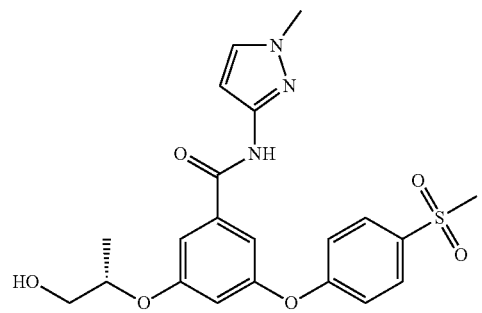 [SMILES: C[C@@H](CO)Oc1cc(Oc2ccc(S(C)(=O)=O)cc2)cc(C(=O)Nc2ccn(C)n2)c1]

and is known by the chemical name 3-(((1S)-2-Hydroxy-1-methylethyl)oxy)-N-(1-methyl-1H-pyrazol-3-yl)-5-(4-(methylsulfonyl)phenoxy)benzamide.

GKA 50 has the following structural formula:

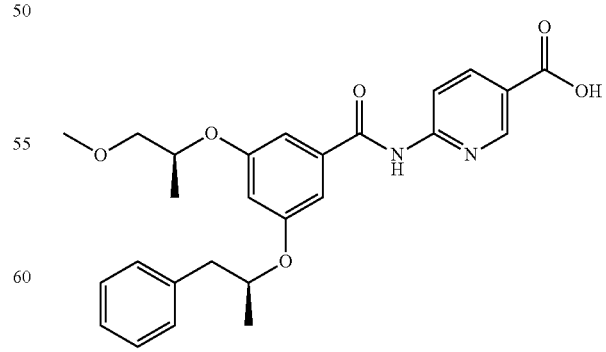

and is known by the chemical name 6[[3-[(1S)-2-Methoxy-1-methylethoxy]-5-[(1S)-1-methyl-2-phenylethoxy]benzoyl]amino-3-pyridinecarboxylic acid.

YH-GKA has the following structural formula:

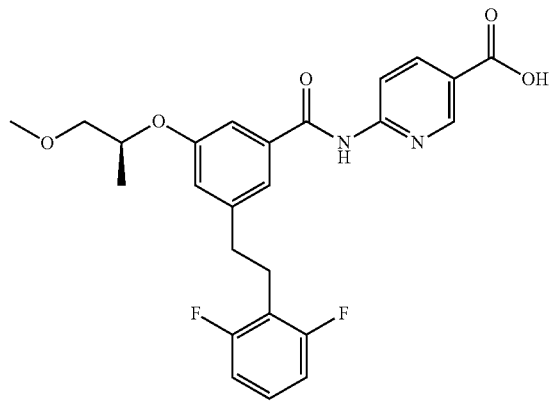 [SMILES: COC[C@H](C)Oc1cc(CCc2c(F)cccc2F)cc(C(=O)Nc2ccc(C(=O)O)cn2)c1]

PSN-010 has the following structural formula:

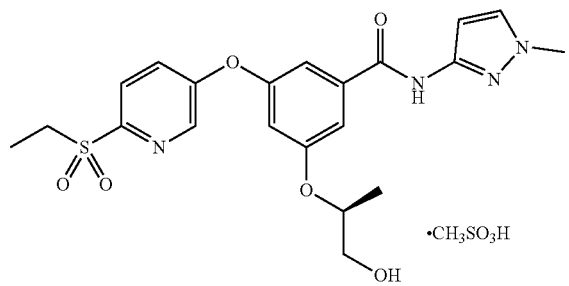

LY2121260 has the following structural formula:

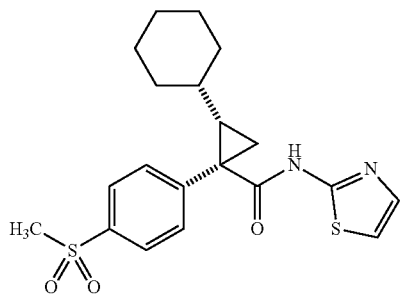

and is known by the chemical name (1R,2S)-2-Cyclohexyl-1-(4-methylsulfonylphenyl)-N-(1,3-thiazol-2-yl)cyclopropane-1-carboxamide.

Eupatilin has the following structural formula:

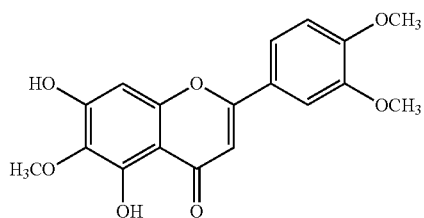 [SMILES: COc1ccc(-c2cc(=O)c3c(O)c(OC)c(O)cc3o2)cc1OC]

and is a flavone derivable from *Artemisia princeps*.

Glucolipsin A has the following structural formula:

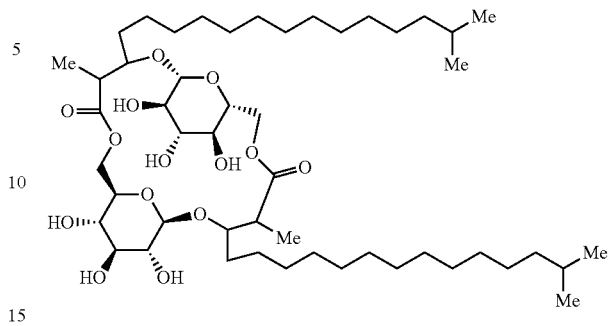

and is a glycolipid derivable from *Steptomyces purpurogenescleroticus*.

Glucolipsin B has the following structural formula:

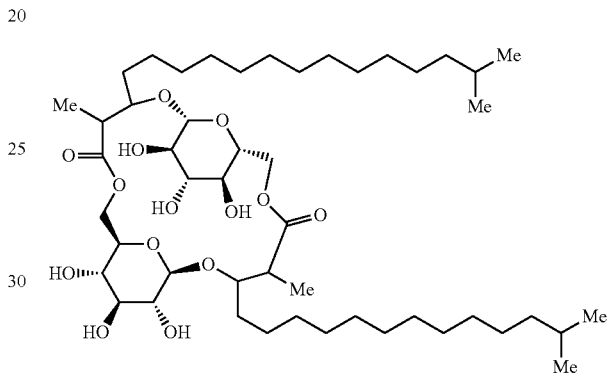

and is a glycolipid derivable from *Nocardia vaccinii*.

In a preferred embodiment, the GCK-activating agent is AZD1656. In a preferred embodiment, the GCK-activating agent is GKA 50.

Also known to the person skilled in the art and of use in the present invention are the glucokinase activators (GKAs) listed in US20130252973A1, US20130165452A1, WO2013086397A1, US20130131113A1, EP2582706A1, US20130029939A1, EP2543667A1, WO2012150202A1, US20120277242A1, EP2513103A1, US20120252814A1, US20120225887A1, US20120214735A1, US20120184544A1, US20120178765A1, US20120165375A1, US20120149704A1, US20120142636A1, EP2444397A1, US20120088760A1, EP2406230A1 and Grewal et al., 2014, each of which is incorporated herein by reference in its entirety.

The cellular target(s) of the glycolysis-activating agent of the present invention may be one or more selected from the group consisting of: Aldolase, AMP-activated protein kinase (AMP Kinase), CD28, CD80, CTLA-4, Enolase, GCK, GCK regulatory protein (GCKR), Hexokinase I (HKI), Hexokinase II (HKII), ICAM-1 and LFA-1.

Disease or Medical Condition

Glycolysis-activating agents and compounds of the present invention find use in the treatment or prevention of diseases and medical conditions.

In one embodiment, the disease or medical condition is an immune-mediated disease or medical condition. Such a disease or condition is marked by the presence of an unwanted or aberrant immune response. Accordingly, in one embodiment, the immune-mediated disease or medical condition is an autoimmune disorder. An "autoimmune disorder" is used herein to mean any disease or condition resulting from an immune response of an organism against its own healthy cells or tissues. In another embodiment, the disease or medical condition is a transplant related disorder. A "transplant related disorder" is used herein to mean any disorder related to or occurring as a result of a patient or subject receiving an organ, tissue or cellular transplant, including the immune rejection of biologic medicines such as monoclonal antibodies. Examples of transplant related disorders include transplant rejection, allograft rejection, vascularized allograft rejection, cell transplant rejection (i.e. stem cells, pancreatic beta cells) and graft versus host disease (GVHD).

In one embodiment, the immune-mediated disease or medical condition, for example the autoimmune disorder, is selected from: transplant rejection, allograft rejection, graft versus host disease (GVHD), systemic lupus erythematosus (SLE), multiple sclerosis (MS), psoriasis, Type I diabetes, Hashimoto's thyroiditis, autoimmune thyroiditis (AITD), myocarditis, myocardial infarction (MI), allergy, infection by virus, bacteria or parasite, cancer, inflammatory bowel disease (IBD), rheumatoid arthritis, autoimmune gastritis, colitis, anti-glomerular basement nephritis, autoimmune hepatitis, primary biliary cirrhosis (PBC), alopecia areata, autoimmune progesterone dermatitis, autoimmune urticaria, pemphigus vulgaris, autoimmune polyendocrine syndrome (APS; with the exception of type 3 APS a.k.a IPEX syndrome), autoimmune pancreatitis, Grave's disease, Sjogrens syndrome, coeliac disease, ulcerative colitis, antiphospholipid syndrome, autoimmune haemolytic anaemia, autoimmune thrombocytopenic purpura, pernicious anaemia, mixed connective tissue disease (MCTD), undifferentiated connective tissue disease (UCTD), psoriatic arthritis, relapsing polychondritis, rheumatic fever, dermatomyositis, myasthenia gravis, polymyositis, acute disseminated encephalomyelitis (ADEM), Guillain-Barré syndrome, Hashimoto's encephalopathy, transverse myelitis, sarcoidosis, autoimmune uveitis, autoimmune inner ear disease (AIED), Behçet's disease, giant cell arteritis, granulomatosis with polyangitis (EGPA), vasculitis, eczema.

In one embodiment, the immune mediated disease or medical condition is myocarditis. In one embodiment, the immune mediated disease or medical condition is graft versus host disease (GVHD). In one embodiment, the immune mediated disease or medical condition is transplant rejection. In one embodiment, the immune-mediated disease or condition is rheumatoid arthritis. In one embodiment, the immune mediated disease or medical condition is Type 1 diabetes. In another embodiment, the immune mediated disease or medical condition, such as the autoimmune disorder, is not Type 1 diabetes.

In another embodiment, the disease or medical condition to be treated is selected from the group consisting of post-transplant diabetes and ischaemia-reperfusion injury.

Autoimmunity

In vivo, Tregs limit autoreactive T-cell activation, thus preventing their differentiation and acquisition of effector functions. By limiting the supply of activated pathogenic cells, Tregs prevent or slow down the progression of autoimmune diseases. This protective mechanism appears, however, insufficient in autoimmune individuals, likely because of a shortage of Tregs cells (at a particular site) and/or the development and accumulation of Treg-resistant pathogenic T cells over the long disease course. Thus, restoration of self-tolerance in these patients may be achieved by homing of Tregs to disease sites or purging of pathogenic T cells along with infusion of Tregs with increased ability to control ongoing tissue injury. Organ-specific autoimmune conditions, such as thyroiditis and insulin-dependent diabetes mellitus have been attributed to a breakdown of this tolerance mechanism.

Diabetes Type 1

Type 1 (juvenile) diabetes is an organ-specific autoimmune disease resulting from destruction of insulin-producing pancreatic beta-cells. In non-diabetics, islet cell antigen-specific T cells are either deleted in thymic development or are converted to T regulatory cells that actively suppress effector responses to islet cell antigens. In juvenile diabetics and in the NOD mouse model of juvenile diabetes, these tolerance mechanisms are missing. In their absence, islet cell antigens are presented by human leukocyte antigen (HLA) class I and II molecules and are recognized by CD8(+) and CD4(+) auto-reactive T cells. Destruction of islet cells by these auto-reactive cells eventually leads to glucose intolerance. By homing Tregs and/or converting existing antigen specific effector T cell to a regulatory phenotype, deleterious autoimmune response is redirected leading to the induction of antigen-specific adaptive tolerance. Modulation of autoimmune responses to autologous epitopes by induction of antigen-specific tolerance can prevent ongoing beta cell destruction.

Accordingly, the present invention is useful in methods for the prevention or treatment of Type 1 diabetes. When treating Type 1 diabetes, the glycolysis-activating agent or GCK-activating agent of the present invention may be administered as part of an insulin administration regimen. In another embodiment, the agent is not administered in conjunction with (such as a simultaneously, sequentially or separately to) insulin. As such, the agent may be an alternative to insulin therapy.

Transplantation

Induction of Ag-specific Treg cells for treating organ-specific autoimmunity is an important therapeutic development, avoiding generalized immune suppression. In murine models of bone marrow transplantation, Tregs promote donor bone marrow engraftment and decrease the incidence and severity of graft versus host disease without abrogating the beneficial graft versus tumor immunologic effect. These findings, in concert with observations that Tregs in mice and humans share phenotypic and functional characteristics, have led to active investigations into the use of these cells to decrease complications associated with human hematopoietic cell transplantation. An imbalance of Tregs and effector T cells contributes to the development of graft versus host disease. However, the mechanisms of immunoregulation, in particular the allorecognition properties of Tregs, their effects on and interaction with other immune cells, and their sites of suppressive activity, are not well understood.

Accumulating evidence from both humans and experimental animal models has implicated the involvement of Tregs in the development of graft versus host disease (GVHD). The demonstration that Tregs can separate GVHD from graft versus tumor (GVT) activity suggests that their immunosuppressive potential could be manipulated to reduce GVHD without detrimental consequence on GVT effect.

In one embodiment, the agent of the invention may be used to increase transplant success rate in a subject or delay transplant rejection in a subject. The transplant may be a skin graft. Thus, the agent may be useful to increase the rate of graft survival or delay skin graft rejection in a subject. In one embodiment, the increase in success rate or delay in rejection is measured relative to a placebo, vehicle, agent-free control or other (conventional) immunosuppressive agent e.g. those aimed at inhibiting the action of effector immune mechanisms (cellular or humoral).

Post-Transplant Diabetes

Type 2 diabetes is the most common cause of end-stage renal failure in the UK. Kidney transplantation is widely held to be the optimal form of renal replacement therapy for patients with end-stage renal disease, leading to a longer survival and improved quality of life in patients receiving a renal transplant compared to those that remain on dialysis (Reese et al, 2015).

However transplantation leads to a higher glucose burden in patients. This has been associated with acute rejection, sepsis and worse outcomes, with patients frequently having to increase their antidiabetic medication in the early post transplant period. One reason for this is that immunosuppressive medications (steroids and calcineurin inhibitors) can lead directly to hyperglycaemia. In addition, as renal function improves, there is greater renal clearance of antidiabetic agents leading to a reduced potency of these medications. These effects are most pronounced with the early post-transplant period, as this is the period when the immunosuppressive burden is the strongest and the changes in renal function most marked.

A short course of a glycolysis-activating agent (such as AZD1656) may be of benefit in controlling diabetes during the time shortly after renal transplantation when the immunosuppressive burden and hence gluconeogenesis is greatest. In addition, glycolysis-activating agents may have additional benefits post renal transplantation in an unrelated action to its anti-diabetic action which involve its effects on immune function.

Without wishing to be bound by theory, it is believed that treatment with a glycolysis-activating agent (such as AZD1656) will lead to more Treg trafficking in the early post-operative course, leading to reduced ischaemia-reperfusion injury through its immunosuppressive effect, followed by increased Treg presence in the transplanted organ (e.g. kidney)—a marker for improved graft survival—and the same time helping to control the early post-transplant diabetic control.

Accordingly, the present invention is useful in methods for the prevention or treatment of post-transplant diabetes, in particular post-renal transplant diabetes. The present invention is useful in methods for the prevention or treatment of diabetes in patients undergoing renal transplantation. In one embodiment, the patient suffering from diabetes has been administered a further antidiabetic medication. The present invention is useful in methods for the prevention or treatment of ischaemia-reperfusion injury. The present invention is useful in methods for improving graft survival post-transplantation. The present invention is useful in methods for increasing the population of Tregs in organ transplant tissue (such as renal transplant tissue) during treatment.

Accordingly, the efficacy of such prevention/treatment described in this section may be assessed by examining altered Treg migration, for example Treg infiltration in renal transplant tissue, for example a change in peripheral Treg population as measured using FACS analysis over a period of e.g. 3 months of treatment, or a change in Treg migration in vitro as measured using any suitable migration assay known to the person skilled in the art.

Thus, secondary endpoints of effective therapy may include: histological staining for Treg cells in renal biopsy tissue between baseline and end of treatment biopsy, diabetic control between baseline and end of treatment using HbA1c as a marker, dose of other antidiabetic medication between baseline and end of treatment, safety endpoints i.e. hypoglycaemic episodes, insulin resistance using HOMA IR quantification, graft function between baseline and end of treatment, episodes of acute rejection, episodes of opportunistic infections (both bacterial and viral) 12-month graft function and diabetic control to assess legacy effect.

Immune Modulation

The glycolysis-activating agent of the present invention may be used to modulate or regulate the immune response in a subject, for example to suppress or repress the immune response in a subject.

The glycolysis-activating agent of the present invention may be used to suppress or regulate an autoimmune response in a subject.

In particular, the treatment or prevention of the disease or medical condition may be mediated via the trafficking of endogenous regulatory T cells (Tregs), for example to a tissue or organ, for example to a diseased tissue or organ or a transplanted tissue or organ.

Accordingly, the glycolysis-activating agents and compounds of the present invention find use in the trafficking of endogenous regulator T cells (Tregs), e.g. to a (diseased) tissue or organ, in a subject suffering from or at risk of suffering from a disease or medical condition.

Further still, the glycolysis-activating agents and compounds of the present invention find use in the treatment or prevention of a disease or medical condition that is alleviated by the trafficking of endogenous regulatory T cells to a tissue or organ, for example a diseased tissue or organ.

By "diseased tissue or organ", it is meant a tissue or organ in any abnormal or pathological state. For example, the tissue or organ may be affected by an immune disease, disorder or medical condition, such as an autoimmune disorder or any of the diseases or conditions described herein.

In one embodiment, the Tregs are naturally arising, intra-thymic-generated Tregs (natural Tregs). In another embodiment, the Tregs are peripherally generated, inducible Tregs (inducible Tregs).

In related embodiments, the glycolysis-activating agent may simultaneously suppress any of effector T cell response, helper T cell response or B cell response. Advantageously, the glycolysis-activating agent may be administered in conjunction with an agent which suppresses any of effector T cell response, helper T cell response or B cell response.

Trafficking of Tregs

The term "trafficking of Tregs" relates generally to the movement of Tregs, for example it may relate to their motility or migration. Such trafficking, homing or migration may be in a specific direction or to a specific location or site.

The effect of the present invention may be achieved primarily by the trafficking, homing or migration of Tregs to a disease site, for example to inflamed tissue or to a diseased tissue or organ. In a preferred embodiment, the Treg cell migrates to a diseased tissue or organ. In one embodiment, the Treg cells migrate to the spleen or peritoneum, advantageously to the peritoneum. The cellular mechanisms which enable Tregs to traffick in this manner are known to the person skilled in the art.

Treg migration assays are known to the person skilled in the art and are described in further detail herein.

Method of Treatment

The present invention also encompasses methods of treating or preventing an immune mediated disorder or condition in a subject, said method comprising administering a glycolysis activating agent to the subject.

The term "treating or preventing" is intended to encompass any form of treatment, prevention or diagnosis, and includes treatments to both cure and prevent disease. Thus, treatment of a healthy subject is to be considered as therapy. Treatment or prevention also covers the alleviation of symptoms, in addition to curative treatments for a disease.

Dosage and Administration

The present invention provides a pharmaceutical composition comprising the glycolysis-activating agent for use according to the invention and a pharmaceutically acceptable carrier, vehicle, diluent or excipient.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). Dosage forms suitable for oral use are preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl Q-hydroxybenzoate, antioxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms of the glycolysis-activating agent of the present invention will generally contain about 1 mg to about 500 mg of an active ingredient, such as 1, 10, 20, 50, 100, 200, 250 or 500 mg of an active ingredient. Preferably, the dosage unit form contains about 100 mg of active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes will naturally vary according to the nature and severity of the conditions, the age and sex of the animal or patient and the route of administration, according to well known principles of medicine. In one embodiment, the patient is aged 18-75 years.

In using a glycolysis-activating agent, for example a GCK-activating agent, for example AZD1656 for therapeutic or prophylactic purposes it will generally be administered so that a daily dose in the range, for example, 0.5 mg to 75 mg per kg, such as 1 mg to 50 mg per kg, such as 5 mg to 30 mg per kg, such as 10 to 25 mg per kg, such as 20 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred. In a preferred embodiment, the glycolysis-activating agent of the invention (such as AZD1656) may be administered at a dosage of 20 mg per kg body weight daily or twice daily for a period of 1-3 weeks, such as 2 weeks.

In a preferred embodiment, the glycolysis-activating agent of the invention (such as AZD1656) may be administered once, twice, three or four times daily. The course of the glycolysis-activating agent may be for any period of time, but in a preferred embodiment, the glycolysis-activating agent of the invention (such as AZD1656) may be administered for a period of 1 week to 6 months, such as for a period of 1 to 6 months, such as for a period of 2 to 4 months, such as for a period of 3 months.

In a preferred embodiment, the glycolysis-activating agent of the invention (such as AZD1656) may be administered via the oral route in a dosage unit form of about 1 mg to about 500 mg, such as about 100 mg, once, twice, three or four times daily for a period of 1 week to 6 months, such as for a period of 1 to 6 months, such as for a period of 2 to 4 months, such as for a period of 3 months. In a particularly preferred embodiment, the glycolysis-activating a gent of the invention (such as AZD1656) is administered in a unit dosage form of 100 mg twice daily via the oral route for a period of three months.

Salts

The compounds can be present as salts, in particular pharmaceutically acceptable salts or esters.

Pharmaceutically acceptable salts of the compounds include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as (C1-C4)-alkyl- or aryl-sulfonic acids which are unsubstituted or substituted (for example, by a halogen) such as methane- or p-toluene sulfonic acid.

Enantiomers/Tautomers

In all aspects of the present invention previously discussed, the invention includes, where appropriate all enantiomers and tautomers of the compounds of the invention. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the compounds of the present invention. The terms used in the claims encompass these forms.

Polymorphs

The invention furthermore relates to compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The compounds for use in the invention may be administered in the form of a prodrug. A prodrug is a bioprecursor or pharmaceutically acceptable compound being degradable in the body to produce a compound of the invention (such as an ester or amide of a compound of the invention, particularly an in vivo hydrolysable ester). Various forms of prodrugs are known in the art.

Examples of prodrugs are as follows. An in vivo hydrolysable ester of a compound of the invention containing a carboxy or a hydroxy group is, for example, a pharmaceutically acceptable ester which is hydrolysed in the human or animal body to produce the parent acid or alcohol. Suitable pharmaceutically acceptable esters for carboxy include C1 to C6 alkoxymethyl esters for example methoxymethyl, C1 to C6 alkanoyloxymethyl esters for example pivaloyloxymethyl, phthalidyl esters, C3 to C8 cycloalkoxycarbonyloxy, C1 to C6 alkyl esters for example 1-cyclohexylcarbonyloxyethyl; 1,3-dioxolen-2-onylmethyl esters, for example 5-methyl-1,3-dioxolen-2-onylmethyl; and c1-6alkoxycarbonyloxyethyl esters. An in vivo hydrolysable ester of a compound of the invention containing a hydroxyl group includes inorganic esters such as phosphate esters (including phosphoramidic cyclic esters) and α-acyloxyalkyl ethers and related compounds which as a result of the in vivo hydrolysis of the ester breakdown to give the parent hydroxy group(s). Examples of α-acyloxyalkyl ethers include acetoxymethoxy and 2,2-dimethylpropionyloxy-methoxy.

A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Combination Therapies

The glycolysis-activating activity described herein may be applied as a sole therapy or in combination with one or more other substances and/or treatments for the indication being treated. Such conjoint treatment may be achieved by way of the simultaneous, sequential or separate administration of the individual components of the treatment. Simultaneous treatment may be in a single tablet or in separate tablets.

In one embodiment, the glycolysis-activating agent of the invention is administered in combination or conjointly with an immunosuppressant, a cell therapy, tolerogenic dendritic cell therapy, an anti-inflammatory agent and/or a hormone replacement therapy such as insulin or thyroid hormone. A hormone replacement therapy is particularly advantageous for the treatment of autoimmune disorders, e.g. insulin for the treatment of Type I diabetes.

As used herein, "simultaneously" is used to mean that the two agents are administered concurrently. Thus, administration "sequentially" may permit one agent to be administered, for example, within 5 minutes, 10 minutes or a matter of hours after the other provided the circulatory half-life of the first administered agent is such that they are both concurrently present in therapeutically effective amounts. The time delay between administration of the components will vary depending on the exact nature of the components, the interaction therebetween, and their respective half-lives.

In contrast to "sequentially", "separately" is used herein to mean that the gap between administering one agent and the other is significant i.e. the first administered agent may no longer be present in the bloodstream in a therapeutically effective amount when the second agent is administered. In one preferred embodiment, the second agent is administered at least 2 hours, more preferably at least 4 hours, even more preferably at least 8 hours, even more preferably still at least 12 or 24 or 48 or 72 hours after the first agent. In one particularly preferred embodiment, the second agent is administered at least 24 hours after the first agent.

Additional Aspects

Whilst the uses and methods described herein are generally applicable to endogenous Treg cells, it is also believed that the induction of Treg trafficking or migration via activation of glycolytic pathways finds use in the priming of autologous and/or allogeneic Treg cells. For example, it is conceivable that a patient's own Treg cells may be isolated, activated using a glycolysis-activating agent, and re-introduced into a patient. The Tregs may be optionally expanded.

As such, also provided herein is an ex vivo method of trafficking or mobilising a Treg cell comprising the step of activating glycolysis in the Treg cell by contacting the Treg cell with a glycolysis-activating agent. The method may comprise the step of inducing proliferation of the Treg, e.g. prior to glycolysis activation.

Accordingly, also provided herein is an ex vivo method of increasing the efficiency of Treg cell (e.g. adoptively transferred Tregs) localization to an inflammatory site comprising the step of pre-treating autologous and/or allogeneic Treg cells with a GCK activating agent. Such a pre-treating step may be defined as an incubation of Treg cells with culture medium containing a GCK activating agent, for example for at least 2 hours at 37° C. The method may comprise the step of inducing proliferation of the Treg cells or expanding the Treg cells, e.g. prior to glycolysis activation. Such methods of expansion and proliferation are established and known to the person skilled in the art.

The above methods may comprise the step of optionally isolating Treg cells e.g. from the subject to be treated (i.e. autologous) or from another subject or source (i.e. allogeneic).

Accordingly, the present invention also provides a method of treating an immune mediated disease or medical condition as described herein comprising the steps of:
a) isolating Treg cells from a subject to be treated and/or isolating Treg cells from another subject or source;
b) expanding the Treg cells from step (a) to obtain sufficient numbers for therapy;
c) contacting or pre-treating the Treg cells from step (b) with a GCK-activating agent;
d) administering the Treg cells from step (c) into the subject to be treated.

The Treg cells from step (c) may be administered or infused into the subject using any suitable dosing regimen. For example, the Tregs maybe administered at a dosage measured in no. Tregs per kg body weight, and in various dosing schedules (e.g. one or more infusions with infusions at various intervals).

Accordingly, also provided herein is an isolated, glycolytically-activated Treg cell. Also provided herein is a glycolytically-activated Treg cell for use in medicine, wherein the Treg is optionally isolated. In one embodiment, the glycolytically-activated Treg is a GCK-activated Treg or a AZD1656-treated Treg. The isolated Treg cell of these aspects may be an autologous Treg cell. The isolated Treg cell may contain a mutation in the GCKR gene, for example a deletion in the GCKR gene, for example the entire GCKR gene may be deleted. Such a mutation leads to disinhibition of GCK and Treg migration.

EXAMPLES

The present invention will now be described by way of the following non-limiting examples.

Materials

Mice. All mice used in the experiments of this study were 7-11 weeks. C57BL/6, BALB/c and CBA/Ca mice were purchased from Charles River (UK). Excised secondary lymphoid organs from 4 week-old CTLA-4KO mice (of H-2u haplotype) were provided by Prof D Wraith (University of Birmingham).

Isolation of microvascular endothelial cells. Murine lung microvascular endothelial cells were isolated as previously described (Marelli-Berg et al., 2000).

Isolation of bone marrow-derived Dendritic Cells (BMDCs). Bone marrow-derived DCs were obtained from WT BALB/c (H2-d) mice. Femurs and tibias from 7-to-10-week-old female mice were removed and BM cells were flushed out with PBS using a 27-gauge needle (Becton Dickinson, Cat #302200). Red blood cells were lysed from the cell suspension with lysis buffer (Sigma-Aldrich, Cat #R7757). BM cells ($5 \times 10^6$) were seeded per well in a 6 well plate (Helena bioscience, Cat #92006) in DC medium as described below.

Culture of Dendritic cells. Bone marrow-derived dendritic cells were cultured in RPMI 1640 medium (Gibco, Cat #21875-034) supplemented with 10% FCS, 2 mM glutamine, 50 IU/mL penicillin, 50 µg/mL streptomycin, 50 µM 2-ME and 2% murine granulocyte-macrophage colony stimulating factor (GM-CSF) obtained from the supernatant of the GMCSF hybridoma (gift from Dr. Jian-Guo Chai, Imperial College, London, UK). Cells were cultured at 37° C. in the presence of 5% $CO_2$. On days 3 and 5, fresh culture medium was added to the plates.

For Treg-DC co-cultures, immature BMDCs were collected and used on day 6 of culture. For functional assays, immature DCs were matured overnight with 100 ng/ml lipopolysaccharide (LPS) (Invivogen, Cat #tlrl-3pelps) and were used between 7-to-10 days post-isolation.

Culture of H2-d allospecific Tregs. CD4+CD25+ Treg cells were isolated from spleen and lymph nodes using Dynabeads® FlowComp™ Mouse CD4+CD25+ Treg Cells Kit (Invitrogen Dynal, Cat #11463D). For extremely high purity of Treg cells (>99%), CD4+CD25+Foxp3+ cells were obtained from Foxp3-GFP reporter mice through Fluorescence-activated Cell Sorting. For expansion, Treg cells isolated from C57BL/6 (H2-b) mice were stimulated weekly with either irradiated or mytomycin C (Sigma-Aldrich, Cat #M4287)-inactivated immature BALB/c-derived (H2-d) DCs at a ratio of 5:1 (Treg:DC) (Fu et al., 2014). The co-cultures were maintained in complete T cell medium supplemented with 10U/ml IL-2. Cells were harvested and seeded at an optimal density of $1.5 \times 10^6$ Tregs per well of a 24-well tissue culture (Helena bioscience, Cat #92024) plate each week. The percentage of CD4+Foxp3+ cells after two weeks of culture was greater than 95%. For use in functional assays, Tregs were used 6-8 days after stimulation.

Antibody-mediated T cell activation. Activated T cells were obtained by polyclonal stimulation of LN cells with plate-bound anti-CD3 (1 µg/ml, eBiosciences, Cat #16-0032-85) and plate-bound anti-CD28 (5 µg/ml, eBiosciences, Cat #16-0281-86) in complete T cell medium supplemented with 20 U/ml recombinant IL-2 (Roche, West Sussex, UK) for 7 days at 37° C. Antibody coating of tissue culture plates was performed by incubating antibodies in 200 µl of Tris buffer (pH 8.5) at 37° C. for a period of 1 hour.

Methods

Lymphocyte trans-endothelial migration and chemotaxis assays. Primary microvascular ECs treated with IFN-γ for 48-72 h were seeded ($3 \times 10^4$) and cultured on 2% gelatin-coated Transwell inserts (diameter, 6.5 mm) containing 3-µm pore size (Costar, Cat #CLS3472-48EA) polycarbonate membranes in EC medium for 16 h to from a monolayer. T cells ($5 \times 10^5$) resuspended in migration medium (RPMI 1640 supplemented with 2% fetal bovine serum) were added to each insert and left to migrate through the monolayer; the well volume was also replaced with fresh migration media. The number of migrated T cells was determined by a hemocytometer counting of the cells present in the well media at different time points over a 24-h period. To measure chemotaxis, T cells were seeded onto Transwell™ bare-filter tissue culture well inserts (diameter, 6.5 mm) with 5- or 3-µm pore size (Costar, Cat #CLS3421-48EA) polycarbonate membranes and chemokine-containing migration medium was placed in the bottom of the well. The number of migrated cells was determined by a hemocytometer.

Induction of CD28, CTLA-4 and LFA-1 signaling. Induction of CD28 and CTLA-4 signaling by antibody stimulation was performed as previously described (Schneider et al., 2005; Wells et al., 2001). To induce co-stimulatory signals via CD28 and CTLA-4 co-receptors for functional assay, cells were incubated with antibodies targeting the functional domains of the co-receptors. To induce CD28 signaling, T cells were treated with a mixture of hamster anti-mouse CD28 (5 µg/$5 \times 10^6$ cells) (clone: 37.52, Bio-Rad, Cat #MCA1363) and goat anti-hamster immunoglobulin (Ig) (2.5 µg/$5 \times 10^6$ cells) (Bio-Rad, Cat #STAR104) for different time points as described in each Figure separately. Similarly, CTLA-4 signaling was achieved by incubating T cells with a mixture of hamster anti-mouse CTLA-4 (5 µg/5×10$^6$ cells) (clone: UC10-4F10-11, Becton Dickinson, Cat #553718), and goat anti-hamster immunoglobulin (Ig) (2.5 µg/5×10$^6$ cells) (Bio-Rad, Cat #STAR104). A hamster IgG isotype control was used to observe any non-specific effects of the antibody stimulation (Bio-Rad, Cat #MCA2356). To induce LFA-1 signaling, cells were incubated with 2 µg/5×10$^6$ cells recombinant mouse ICAM-1-human IgG Fc chimeras (2 µg/ml, R&D Systems, Cat #796-IC-050) or human IgG-Fc fragments (R&D Systems, Cat #110-HG) as a control—either plastic-bound or ligated with a mouse anti-human IgG (1 µg/ml, MK1A6, Bio-Rad Cat #MCA647G)—for different time points as described in each Figure separately. T cells were washed in PBS prior to use in the experiments.

Fluorescent labelling of viable T cells. For labelling T cells with fluorescent probes, T cells were washed with PBS, counted and resuspended in PBS at a final concentration of 10$^7$/ml. If necessary, dead cells were removed using density gradient centrifugation with Ficoll-Paque prior to re-suspension. Labelling of T cells with PKH26 (Sigma-Aldrich, Cat #PKH26GL-1KT), a cell linker dye for cell membranes was performed using manufacturer instructions. PKH26 was added at a final concentration of 5 µM, and the cells were incubated at room temperature for 5 minutes. The reaction was inactivated by adding an equal volume of FBS to the cell suspension and the cells were washed in PBS containing 10% FBS for 10 minutes. Labeling of T cells with succinimidyl ester dyes CFSE (Invitrogen, Cat #C1157) or DDAO-SE (Invitrogen, Cat #C34553) was performed by incubating the T cells in PBS containing final concentration of 3.3 µm CFSE or 1.3 µm DDAO-SE for 10-15 minutes at room temperature. The reaction was terminated by adding equal volume FBS and the cells were then washed with PBS containing 10% FBS for 10 minutes.

T cell recruitment in the peritoneum. To observe in vivo recruitment of T cells we used the previously described model of T cell recruitment (Mirenda et al., 2007). Either PKH26 or CFSE or DDAO-SE-labelled T cells (10$^7$) were injected intravenously (i.v.) into mice that hd received IFN-γ (600U) via intraperitoneal injection (i.p.) 48 to 72 hours earlier. Labeled T cells recovered via peritoneal lavage were analyzed 16 hours later using flow cytometry. In addition, localization of Tregs to the spleen, where entry occurs in a passive manner (Fu et al., 2016), was analyzed to ensure that similar numbers/proportion of labeled cells were injected or co-injected in all recipients (internal control).

Zymosan-induced peritonitis. On day 0, mice were given intraperitoneal injections of Zymosan (1 mg/mouse, Cat #4250 SIGMA) in sterile saline solution to induce peritonitis. Mice were sacrificed 72 hours post-injection and tissue samples obtained for flow cytometry analysis.

Widefield deconvolution fluorescence microscopy. Tissues samples were excised, embedded in Optimal Cutting Temperature compound (OCT; Thermo Fisher Scientific, Cat #12678646), snap-frozen and stored until analysis. Frozen tissue sections were laid onto Polysine coated microscope slides (VWR International, Cat #47100), air dried and then fixed with ice cold acetone (Sigma, Cat #534064) for 10 min. Tissue sections were washed in PBS, blocked with serum for 3 hours and stained using mentioned primary antibodies at 4° C. for 24 h. Excess antibody was washed away with PBS and tissues were stained with indicated secondary antibodies along with DAPI (4',6-diamidino-2-phenylindole) (Invitrogen/LifeTechnologies, Cat #D1306) for 30 min at room temperature. Slides were washed, mounted in ProLong Gold Antifade Reagent (Invitrogen/Life Technologies, Cat #P36930) and visualized using a Zeiss Z1 fluorescence microscope (Carl Zeiss, UK) equipped with an AxioCam MRm Cooled monochrome digital camera and an Apotome 2 Imaging unit. Images were acquired using a Plan Apochromat 20×/0.8 NA objective and Axiovision software version 4.8 (Carl Zeiss, UK). For staining, Tregs were cultured in R10 medium and fixed with 3.7% formaldehyde. After fixing, they were stained with anti-GCK, anti-Na,K-ATPase and 1 ng/ml tetramethyl rhodamine B isothiocyanate-conjugated phalloidin (Sigma-Aldrich Cat #P1951) for 30 min at 37° C. and respectively. This was followed by secondary antibodies Alexa Fluor® 555 goat anti-mouse Ig (Biolegend Cat #405324) and FITC Donkey anti-rabbit IgG (minimal x-reactivity) Antibody (Biolegend 406403). Coverslips were extensively washed, air dried, and mounted in Vectorshield mounting medium for fluorescence with DAPI (Vector Laboratories Cat #z0603) on glass slides.

In vitro 6-NBDG uptake assay. Freshly isolated T cells or cultured T cells were washed in PBS and resuspended in glucose free T cell medium (Gibco, Cat #11879-020) containing various mentioned signaling antibodies and incubated for 45 minutes at 37° C. with 5% CO2. A final concentration of 400 µM 6-NBDG (Life Technologies, Cat #N23106) in glucose free T cell medium was then added to the cells and the cells were further incubated for an additional 10-15 minutes. Finally, the cells were washed twice with warm PBS and resuspended in flow cytometry buffer and placed on ice. Immediate analysis was performed using flow cytometry to observe fluorescence uptake by the T cells.

In vitro 6-NBDG uptake assay (human studies). Freshly isolated CD3$^+$ T cells were washed in PBS and cultured 10$^6$/mL in R2 (RPMI 1640 supplemented with 2% fetal bovine serum) with recombinant CCL19 and CCL21 (200 ng/mL—Peprotech Cat #300-29B and 300-35) at 37° C. with 5% CO$_2$. A final concentration of 400 µM 6-NBDG (Life Technologies, Cat #N23106) was added to the cells and incubated for 0, 15, 30 and 60 minutes. Finally, the cells were washed twice with warm PBS, stained for CD4$^+$ T cells and Treg and placed on ice. Immediate analysis was performed using flow cytometry to observe fluorescence uptake by Tregs.

In vivo 6-NBDG uptake assay. To measure glucose uptake activity of T cells in vivo, PKH26 labelled T cells (3×10$^6$) were injected i.p. into mice. A second i.p. injection of 6NBDG (400 µM in Sterile water) was given to the mice immediately afterwards. After a 1-hour period, the mice were sacrificed and the mesenteric (draining) lymph nodes and spleen collected for analysis by flow cytometry. Widefield microscopy of the peritoneal membranes was performed to observe influx of labelled T cells into the peritoneal membrane. PKH26+ T cells infiltrating the membranes were further analyzed for 6NBDG uptake (green fluorescence) using image analysis software ImageJ. The number of labelled cells in 10× magnification field views images was counted manually to determine differences in T cell infiltration.

Measurement of ECAR and OCR. Real time bioenergetics analysis of extracellular acidification rates (ECAR) and oxygen consumption rates (OCR) of T cells subjected to antibody stimulation was performed using the XF analyzer (Seahorse biosciences). T cells were cultured in serum free, unbuffered XF assay medium (Seahorse biosciences, Cat #102365-100) for 1 hour. The cells were then seeded (6×10$^5$/well) into the seahorse XF24 cell plates for analysis. Perturbation profiling of the use of metabolic pathways by T cells was achieved by the addition of oligomycin (1 µM), FCCP (1 µM), Antimycin A (1 µM), rotenone (1 µM), D-glucose (10 mM), 2-Deoxy-D-glucose (2DG, 50 mM; all from Seahorse biosciences, Cat #103020-100 and 103015-100). Experiments with the Seahorse system were done with the following assay conditions: 2 min mixture; 2 minutes wait; and 4-5 min measurement. Metabolic parameters were calculated. Experiments were done in at least triplicate wells.

Surface staining. For surface staining, cells were resuspended ($10^7$/ml) and stained with flurochrome-conjugated antibodies in 100 µl of Flow cytometry buffer made of PBS containing 0.1% sodium azide (Sigma-Aldrich, Cat #52002-25G) and 1% FBS at 4° C. for 30 minutes. CCR7 antibody staining was performed at 37° C. for 30 mins. Optimal antibody concentrations for staining were calculated based on manufacturer instructions. Following staining, cells were washed and resuspended with flow cytometry buffer and analyzed immediately. Alternatively, for delayed analysis, cells were fixed in fixation buffer (flow cytometry buffer containing 1% Formaldehyde (Sigma-Aldrich, Cat #15,812-7)) for 30 minutes at 4° C., washed and stored in flow cytometry buffer at 4° C.

Intracellular staining. For intracellular Foxp3 staining, eBioscience Anti-Mouse/Rat Foxp3 Staining Set APC (clone FJK-165, Thermo Fisher Scientific Cat #17-5773-82) kit was used. Cells were resuspended ($10^7$/ml) and stained with surface antigens as mentioned above and then fixed/permeabilized for 30 minutes at 4° C. using Fixation/Permeabilization working solution made from mixing 1 part of the fixation/permebilization concentrate (eBioscience, Cat #00-5123) to 3 parts of the fixation/permebilization diluent (eBioscience, Cat #00-5223). The cells were then washed twice in 1× permeabilization buffer (eBioscience, Cat #00-8333) and stained with fluorochrome conjugated-Foxp3 antibody in 1× permeabilization buffer for 30 minutes at 4° C. A final wash with 1× permeabilization buffer was performed and the cells were then centrifuged and resuspended in 200 ul of flow cytometry buffer. For T cell proliferation studies, Tregs were stimulated with immature Balb/c DCs. 3 hours later, Tregs were fixed and permeabilized with ice cold 70% ethanol before staining for proliferating cell nuclear antigen (PCNA, clone PC10, BioLegend Cat #307908).

In vitro AKT phosphorylation (human studies). Freshly isolated concentional $CD4^+CD25^-$ T cells (Tconv) and $CD4^+CD25^+$(Treg) T cells were washed in PBS and cultured $5\times10^6$/mL in R2 (RPMI 1640 supplemented with 2% fetal bovine serum). $0.5\times10^6$ $CD4^+CD25^-$ (Tconv) and $CD4^+$ $CD25^+$ (Treg) were plated in 96-well plate and stimulated for 15 minutes or not with chemokines CCL19 and CCL21 (1 µg/mL—Peprotech Cat #300-29B and 300-35) at 37° C. with 5% $CO_2$. Cells were immediately fixed to stop stimulation with 2% formaldehyde for 10 minutes at RT in the dark. Cells were washed and resuspended in 100% ice-cold methanol and incubated for 30 minutes on ice. Subsequently, cells were washed twice with PBS 2% FBS and stained for pAKT-s473 (eBioscience, Cat #17-9715-41) for 30 minutes at 4° C. in the dark. Cells were washed, resuspended in PBS+2% FBS and immediately analyzed by flow cytometry.

Western Blotting and coimmunoprecipitation. Whole-cell lysates were lysed in Nonidet P-40 lysis buffer [50 mM Hepes (pH 8.0), 350 mM NaCl, 1% Nonidet P-40, 1 mM EDTA, 1 mM $Na_3VO_4$, 1 mM NaF, 20 mM glycerol-2-phosphate, 1 mM PMSF, 1 mM DTT, 10 µg/mL aprotinin, 10 µg/mL leupeptin, and protease inhibitor cocktail (Roche Cat #11836145001). Equivalent amounts of protein as determined by standard Bradford assay (Bio-Rad Cat #5000001) were separated by SDS/PAGE and transferred to nitrocellulose membrane (GE Healthcare Life Sciences Cat #10600002). Membranes were blocked for 2 h at room temperature in 5% milk/TBS-Tween 20 (Sigma Cat #P1379) and were incubated overnight at 4° C. with the primary antibodies listed below. HRP-conjugated secondary antibody (1:5000; Amersham Bioscience Cat #NA934) was subsequently added. Films were then developed. The intensity of the bands was quantified using ImageJ (NIH). For coimmunoprecipitation experiments, cell extracts were prepared in RIPA buffer. 250 µg of total protein extract was first precleared with Protein G-Agarose beads (Sigma Cat #P3296) for 1 hour at 4° C., incubated with 5 µg of anti-GCK Ab (Santa Cruz Biotechnology Cat #SC7908) overnight at 4° C. and then with Protein G beads for another 16 hrs at 4° C. The final pellet was resuspended in 10 mM Tris HCl, pH 7.4, supplemented with 1 mM PMSF and analysed by western blot for B actin (Santa Cruz Cat #SC161).

Quantitative real time PCR (qRT-PCR). Tissues were harvested and stored in RNA-later (Qiagen Cat #76104) at −80° C. until processing. RNA was purified using Trizol reagent (Life Technologies Cat #15596) according to the manufacturer's instructions and assessed for quality and quantity using absorption measurements. Reverse transcription was performed according to the manufacturer's instruction (Applied Biosystems Cat #4374966). Gene expression analysis was done using SYBR Green Supermix (Biorad Cat #1725120) in CFX connect light cycler (Biorad Cat #1855200). Expression was calculated using the AACt method (Livak and Schmittgen, 2001) and normalized to a housekeeping gene (GAPDH). Primers for qPCR were designed with the help of online tools (Primer 3Plus) using at least one exon junction-binding site per primer pair. The thermal cycling profile for amplification was 95° C. for 10 min, followed by 40 cycles of 95° C. for 15 s and 54° C. for 1 min. Amplification was at 95° C. for 10 min, followed by 40 cycles of 95° C. for 15 s and 60° C. for 1 min. To ensure the amplification specificity, the melting curve program was set as follows: 95° C. for 15 s, 60° C. for 1 min, and 95° C. for 15 s, right after the PCR cycles. Experiments were done in triplicates.

Lentivirus Preparation for Gene Silencing. HEK293T cells were grown in 10 cm cell-culture dishes to 70% confluence and were transfected with the above plasmids using the calcium phosphate method. The supernatant was harvested 48 and 72 h after transfection and was concentrated 100-fold in an ultracentrifuge. Aliquots were stored at −80° C. For transduction of Tregs, cells were seeded in six-well plates and cultured in DMEM to 60-70% confluence. Lentivirus was added to the cells in the presence of 5 µg/mL Polybrene (Sigma-Aldrich Cat #107689), and the six-well plate was centrifuged at 2,300 rpm for 90 min at room temperature, followed by 8 h incubation at 37° C. with 5% $CO_2$. Virus was removed 24 h later; T cells were washed twice with PBS and incubated for 24 h in complete DMEM (Life technologies, Cat #1852730).

Study population. The Progressione della Lesione Intimale Carotidea (PLIC) Study (a sub-study of the CHECK study) is a large survey of the general population of the northern area of Milan (n=2.606) (Baragetti et al., 2015; Lorenz et al., 2012; Norata et al., 2009; Norata et al., 2006), followed at the Center for the Study of Atherosclerosis, Bassini Hospital (Cinisello Balsamo, Milan, Italy). The Study was approved by the Scientific Committee of the Università degli Studi di Milano ("Cholesterol and Health: Education, Control and Knowledge—Studio CHECK ((SEFAP/Pr.0003)—reference number Fa-04-Feb-01) in Feb. 4, 2001. An informed consent was obtained by subjects in accordance with the Declaration of Helsinki.

Genomic DNA was extracted using Flexigene DNA kit (Qiagen, Milan, Italy) as previously described (Norata et al., 2007). Genotyping for the p.Leu446Pro GCKR missense mutation was available on the entire population, using TaqMan allelic discrimination test. The experimental analysis was conducted on a subgroup of 16 subjects, eight Leu 446-GCKR and eight Pro 446-GCKR matched for age and gender. Information on medical histories and ongoing therapies were obtained; Body Mass Index (BMI, Kg/m2) was calculated and, after an over-night fast, blood samples were collected from the antecubital vein for the determination of lipid profile, glucose levels, liver enzymes, leukocyte count and subfractions as previously described (Ammirati et al., 2012; Baragetti et al., 2015; Norata et al., 2006).

Blood surface and intracellular staining (human studies). For surface staining, 100 $\mu$L of whole blood were stained with flurochrome-conjugated antibodies in 50 $\mu$L of MACS buffer made of PBS containing, 2% FBS and 2 $\mu$M EDTA at RT (room temperature) for 30 minutes in the dark. Optimal antibody concentrations for staining were calculated based on manufacturer instructions. Following staining, red blood cells were lysed with 2 mL of 1-step fix/lyse solution (eBioscience, Cat #00-5333-54) for 20 minutes at RT, washed and resuspended with MACS buffer and analyzed immediately.

Alternatively, for intracellular staining, peripheral blood mononuclear cell (PBMCs) were isolated (as described below) and used for the staining (1-step fix/lyse solution is incompatible with some intracellular stainings). Cells were resuspended ($10^7$/mL) and stained in in 50 $\mu$L of MACS buffer with surface antigens. For intracellular Foxp3 and Ki67 staining, eBioscience Anti-Mouse/Rat Foxp3 Staining Kit was used (Cat #77-5775-40). Cells were fixed/permeabilized ON at 4° C. using Fixation/Permeabilization working solution made from mixing 1 part of the fixation/permebilization concentrate to 3 parts of the fixation/permebilization diluent. Cells were then washed twice in 1× permeabilization buffer and stained with fluorochrome conjugated-Foxp3 and -Ki67 antibodies in 2× permeabilization buffer for 30 minutes at 4° C. A final wash with 1× permeabilization buffer was performed and the cells were then centrifuged and resuspended in 200 $\mu$L of MACS buffer.

PBMC isolation and CD4$^+$CD25$^+$ Treg purification (human studies). For each subject, 30 mL of blood (supplemented with EDTA) were split in two falcon of 15 mL and spin for 12 minutes at 1000×g. Plasma was discarded and the interface between plasma and red blood cells, enriched in leukocytes and platelets (buffy coat), was carefully collected, diluted with cold PBS and stratified on 3 mL of Ficoll-Plaque™ PREMIUM (GE-Healthcare, Cat #17-5442-03). After centrifugation of 35 minutes at 250×g, PBMC layer was carefully collected and was 3 times with 10 mL of cold PBS at 180×g for 12 minutes to get rid of platelets. PBMC were counted and use for CD4$^+$CD25$^+$ Treg purification with CD4+CD25+ Regulatory T cell isolation kit, human (Miltenyi Biotec., Cat #130-09-301) according to manufacturer instructions. Purified CD4$^+$CD25$^+$ Treg or CD4$^+$CD25$^-$ Tconv were counted with a hemocytometer and used for migration and suppression assay.

Treg and Tconv migration assay (human studies). 300 $\mu$L of Treg and Tconv (1×$10^5$) of each subject were resuspended in migration medium (RPMI 1640 supplemented with 2% fetal bovine serum) and cultured on Transwell™ inserts (diameter, 6.5 mm) with 5-$\mu$m pore size (Costar, Cat #CLS3421-48EA) polycarbonate membranes. Cells were left to migrate versus migration medium or chemokines CCL19 and CCL21 (200 ng/mL—Peprotech Cat #300-29B and 300-35), placed in the bottom of the well, for 1, 2, 4 and 12 hours. The number of migrated cells was determined by a hemocytometer and data expressed as percentage of migration compared to cultured cells.

Treg suppression assay (human studies). CD4$^+$CD25$^-$ Tconv were resuspended in MACS buffer ($10^7$/mL) and labeled with succinimidyl ester dyes CFSE (2 $\mu$M—Invitrogen, Cat #C1157) for 10 minutes at RT in the dark. Cells were washed 3 times with MACS buffer and centrifuged at 360×g for 5 minutes. 96 well-plate U-bottom were coated with anti-human CD3 purified antibody (5 $\mu$g/mL—eBioscience, Cat #14-0039-82) for 1 hour at 37° C. Tconv were resuspended ($10^6$/mL) in complete medium (RPMI 1640 supplemented with 10% FBS, 1 mM Na-Pyruvate, 10 mM Hepes, 50 $\mu$M $\beta$-MeOH and pen/strep/glutamine) plus 50 U/mL of IL-2 (Peprotech; Cat #200-02) and 2 $\mu$g/mL of anti-human CD28 purified antibody (eBioscience, Cat #14-0289-82) and (1×$10^5$/100 $\mu$L) were plated. CD4$^+$CD25$^+$ Treg were washed and resuspended in complete medium and added to Tconv according to the following proportions (Tconv:Treg): 1:1, 1:0,5, 1:0,25 and 1:0 by performing serial dilution of Treg with complete medium. 96 well-plate was spin 1 minute at 120×g to collect cells at the bottom and left to proliferate for 4 days. Cells were then collected and for each subject the percentage of proliferated cells in the presence of Treg was compared to the condition of Tconv: Treg 1:0 (100% proliferation).

Quantification and statistical analysis. The qPCR data were analyzed using the delta delta CT method by taking the CT values of the genes of interest from the house keeping gene following by normalization to the wildtype control sample. Results were done transported to prism before graphic presentation and statistical analysis. Results are given as the mean per group±SD. The data were analyzed using a two-tailed unpaired Student's t test and Mann-Whitney test. A p value of less than 0.05 was considered significant. Experimental data sets from the seahorse were analyzed using one-way ANOVA with Bonferroni correction or Kruskal-Wallis with Dunn's post-test to take into account of multiple comparisons. Where indicated 'n' represent the number of biological replicates. Human data were analyzed by ANCOVA (Analysis of Co-Variances) models between TT and CC genotypes of the rs1260326 GCKR polymorphisms (adjusting by age and gender). Variables are presented as mean (standard deviations, S.D.) if normally distributed or as median (Inter-Quartile Range, IQR) if non-normally distributed (Shapiro-Wilk test). T-test to compare normally distributed variables and U-Mann Whitney for non-normally distributed variables were performed (P values for each variables are reported; p less than 0.05 are significant). Grubb's test for outliers detection was performed for each variables. For human results, data are reported as the mean per group±SEM. The data were analyzed using a two-tailed unpaired Student's t test and Mann-Whitney test. A p value of less than 0.05 was considered significant.

Example 1

Engagement of the Glycolytic Pathway is Required for Treg Migration

Figure 1:
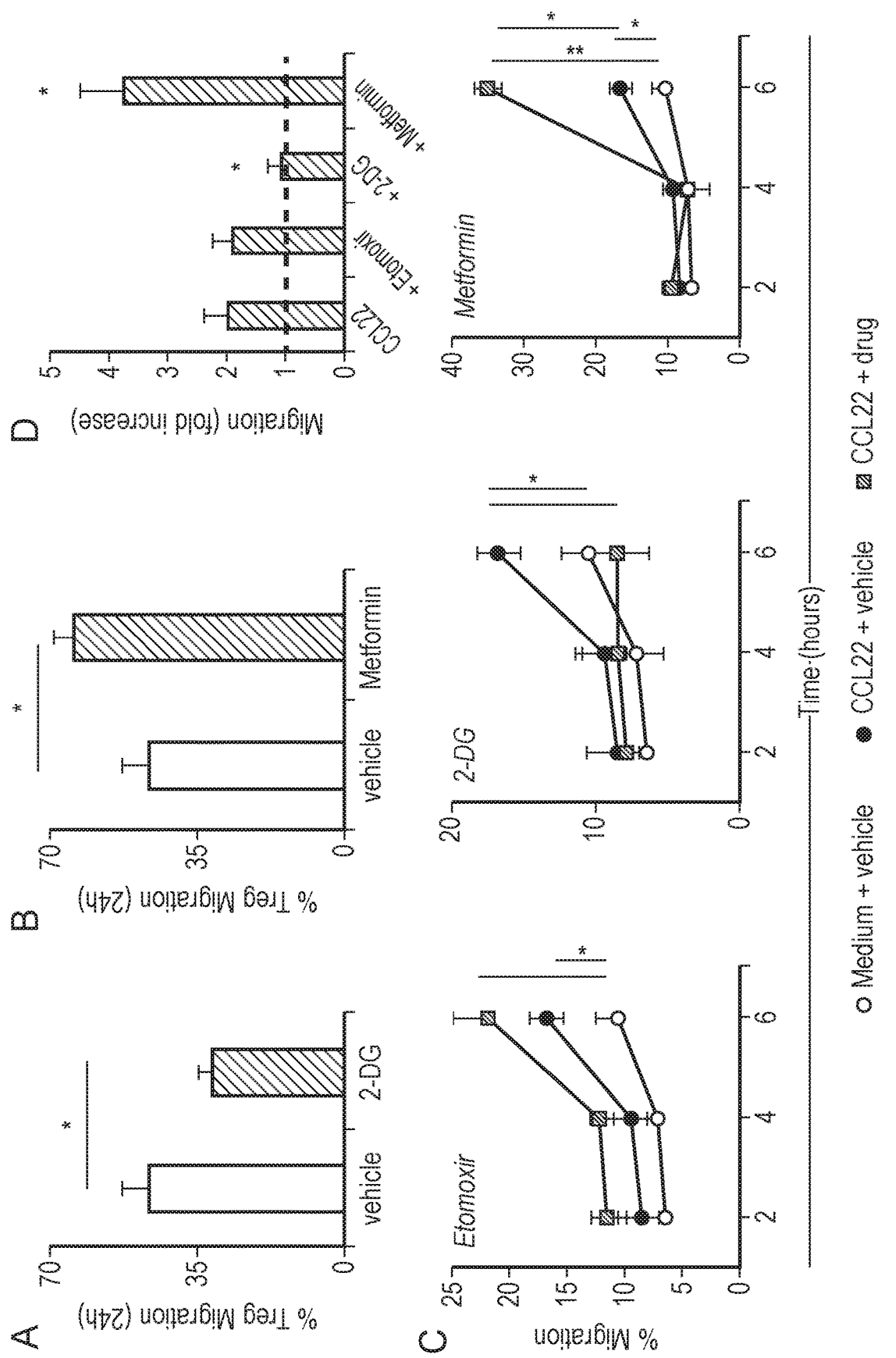
FIG. 1. Glycolysis fuels Treg migration. Ex vivo expanded Tregs pre-treated with the indicated drugs or vehicle for 4 hours were left to migrate through 3 μm-pore transwells layered with IFN-γ-treated syngeneic EC monolayers (A-B) or in response chemokine CCL22 through bare filter 5 μm-pore transwells (C-D). Results are expressed as percentage of migrated cells after 24 hours (A-B, n=4, N=2) or at the indicated time-points (C, n=3)±SD. The fold increase in migration was calculated by dividing experimental migration by spontaneous migration measured at 6 hours in two experiments of identical design performed in triplicates±SD.
Figure 2:
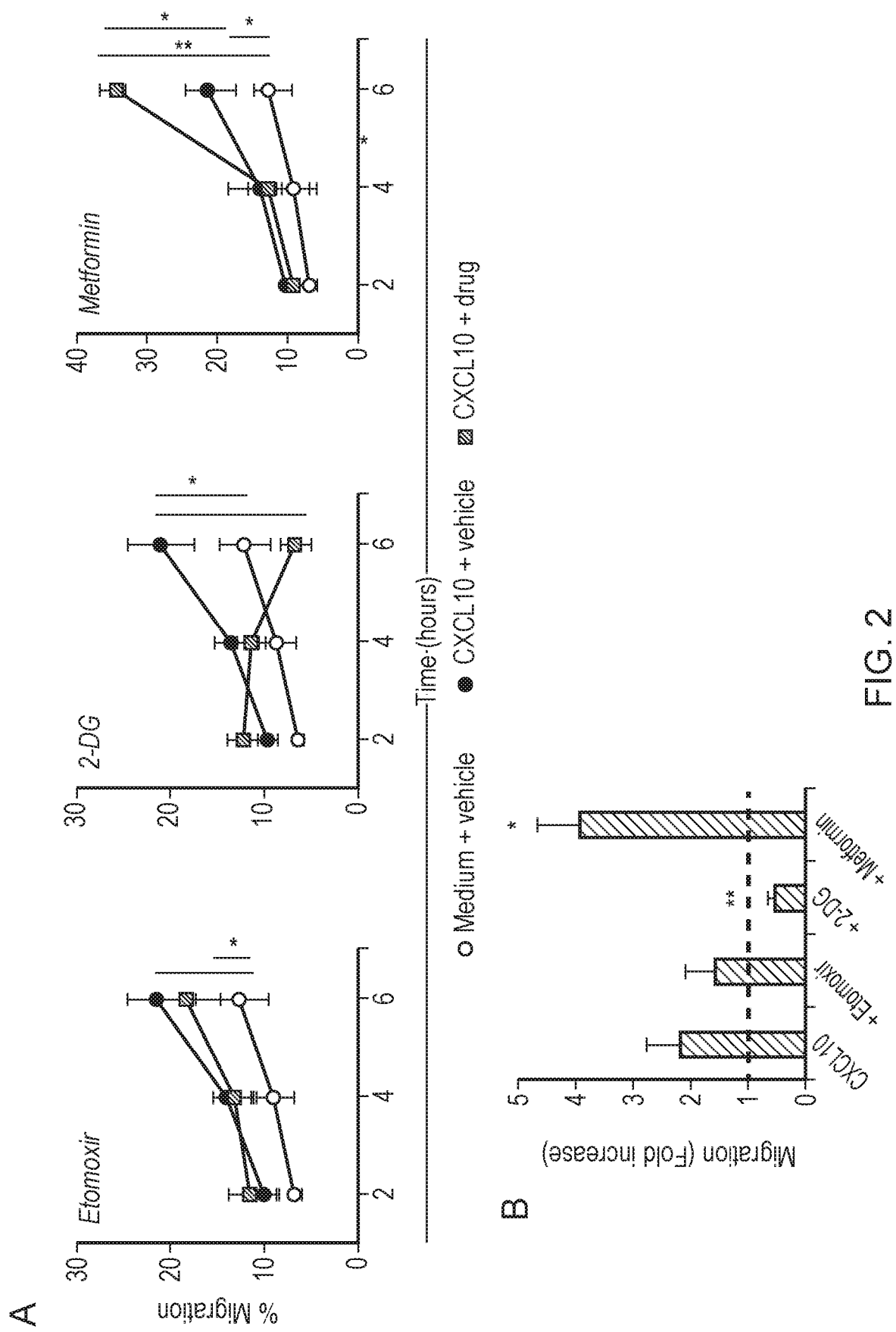
FIG. 2. Activated Treg phenotype and function and effect of exposure to metabolism-modifying drugs. Tregs were expanded as previously described (Fu et al., 2014). A-B Tregs were treated with the indicated metabolism-targeting drugs for 4-6 hours and extensively washed. Migration of drug-exposed Tregs in response to CXCL10 (300 ng/ml) was assessed by a transwell-based assay. Results are expressed as the mean percentage of migrated cells at the indicated time points±SD. Data obtained at 6 hours from three independent experiments of identical design and normalized by spontaneous migration±SD are shown in panel B. $*P<0.05$.
Figure 3:
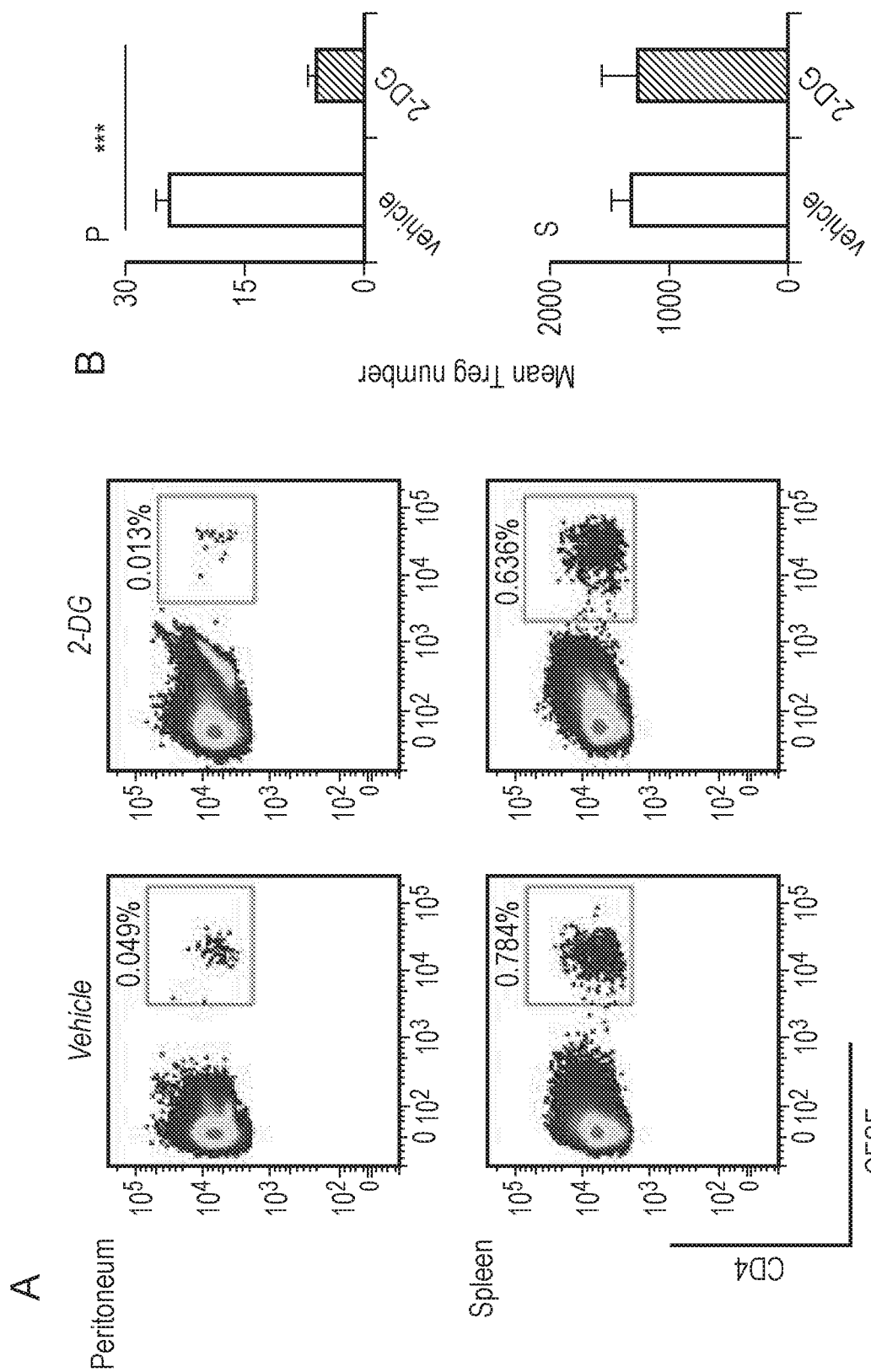
FIG. 3. Drug- or vehicle-treated Tregs labeled with the fluorescent intravital dye PKH26 were injected i.v. into syngeneic recipients treated with IFN-γ i.p. 48 hours earlier. Cells were harvested from the indicated tissues after 24 hours and analyzed by flow cytometry. Representative dot plots from 3 animals are shown in panels A and C. The mean absolute number of labeled cells recovered in 4 animals±SD is shown in panels B and D. (N=1)
Figure 3:
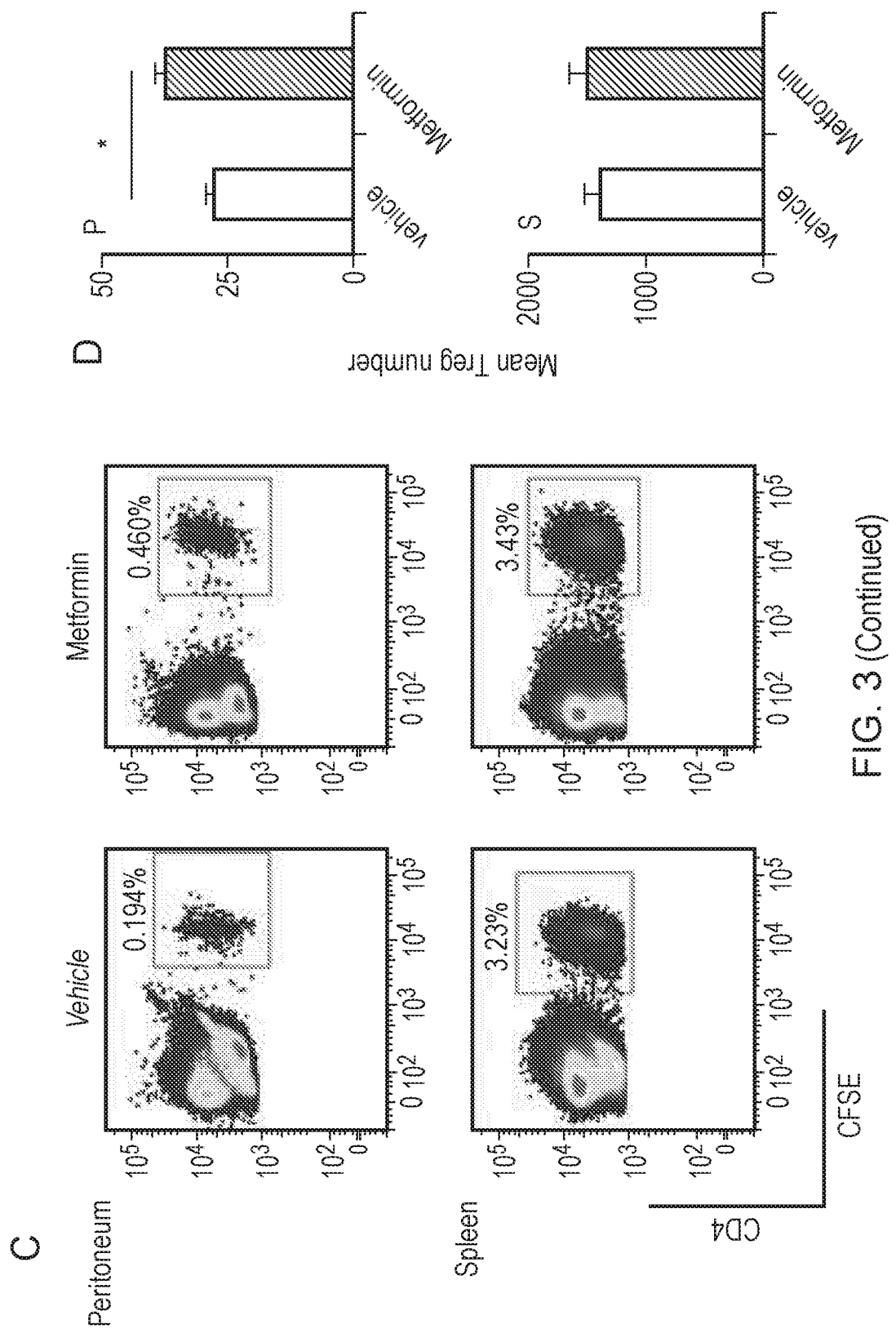
Figure 4:
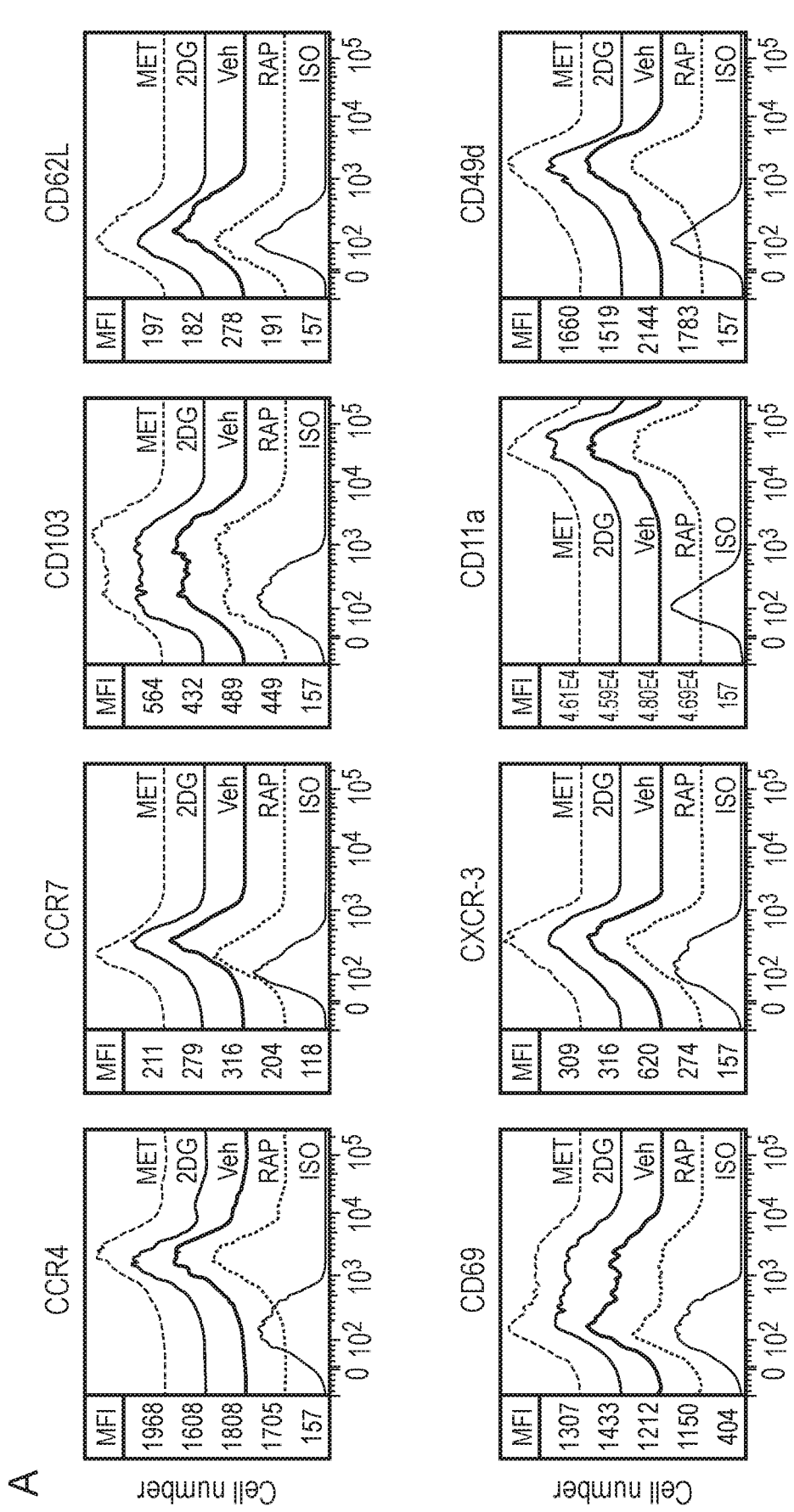
FIG. 4. A: Tregs were treated with the indicated metabolism-targeting drugs for 4-6 hours before the expression of the indicated surface molecules was analyzed by flow cytometry. Representative histograms of the indicated surface molecules and mean fluorescence intensity are shown. N=2. B-C: Apoptosis/necrosis of Tregs treated with the metabolism-targeting drugs indicated for 6 hours was measured by analysis annexin V and propium iodide (PI) staining. Untreated Tregs and Tregs subjected to heat-induced apoptosis were used as negative and positive controls respectively. The bar graphs (C) show the mean percentages of apoptotic and necrotic Treg cells±SD. (n=4, N=3).
Figure 4:
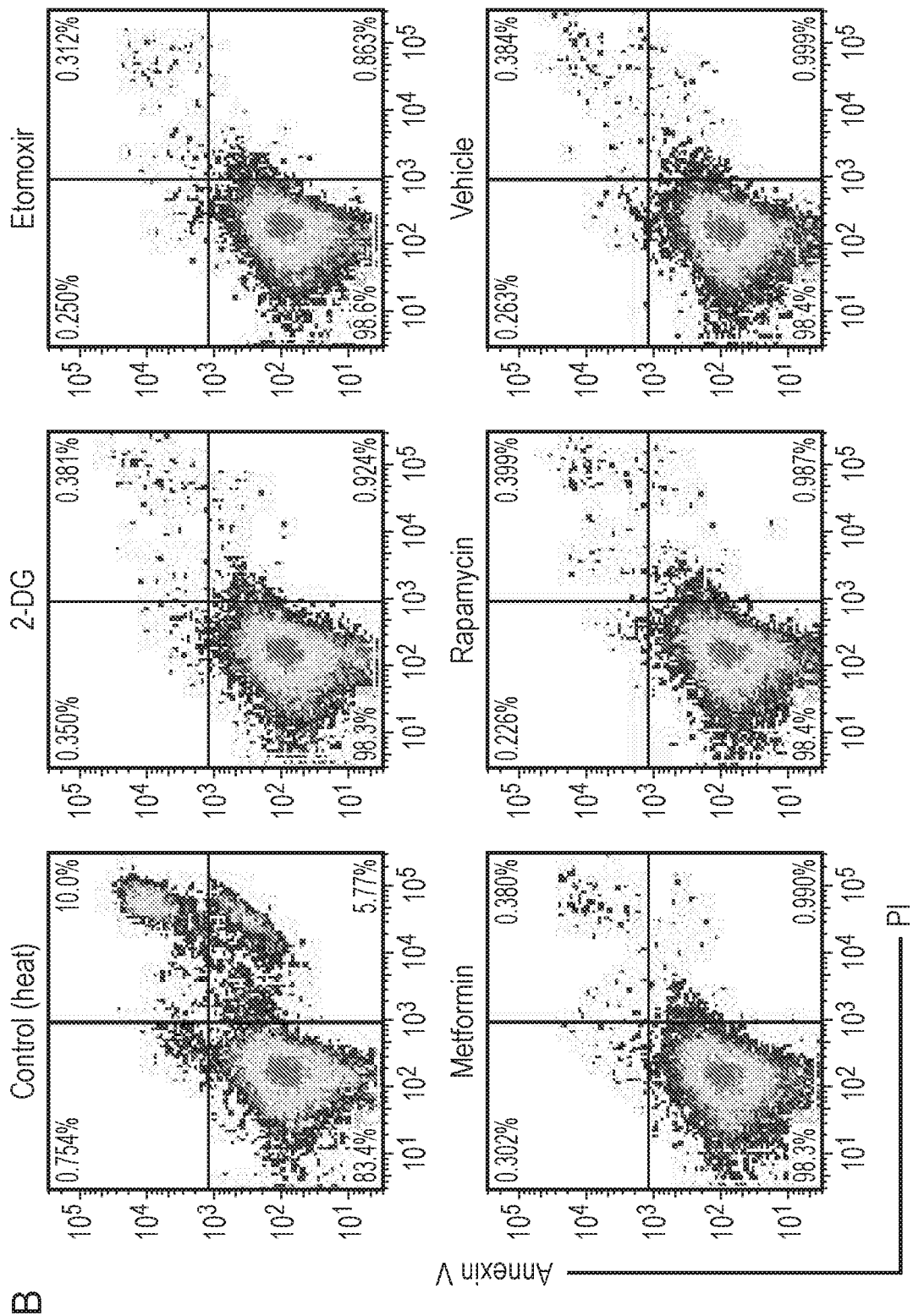
Figure 4:
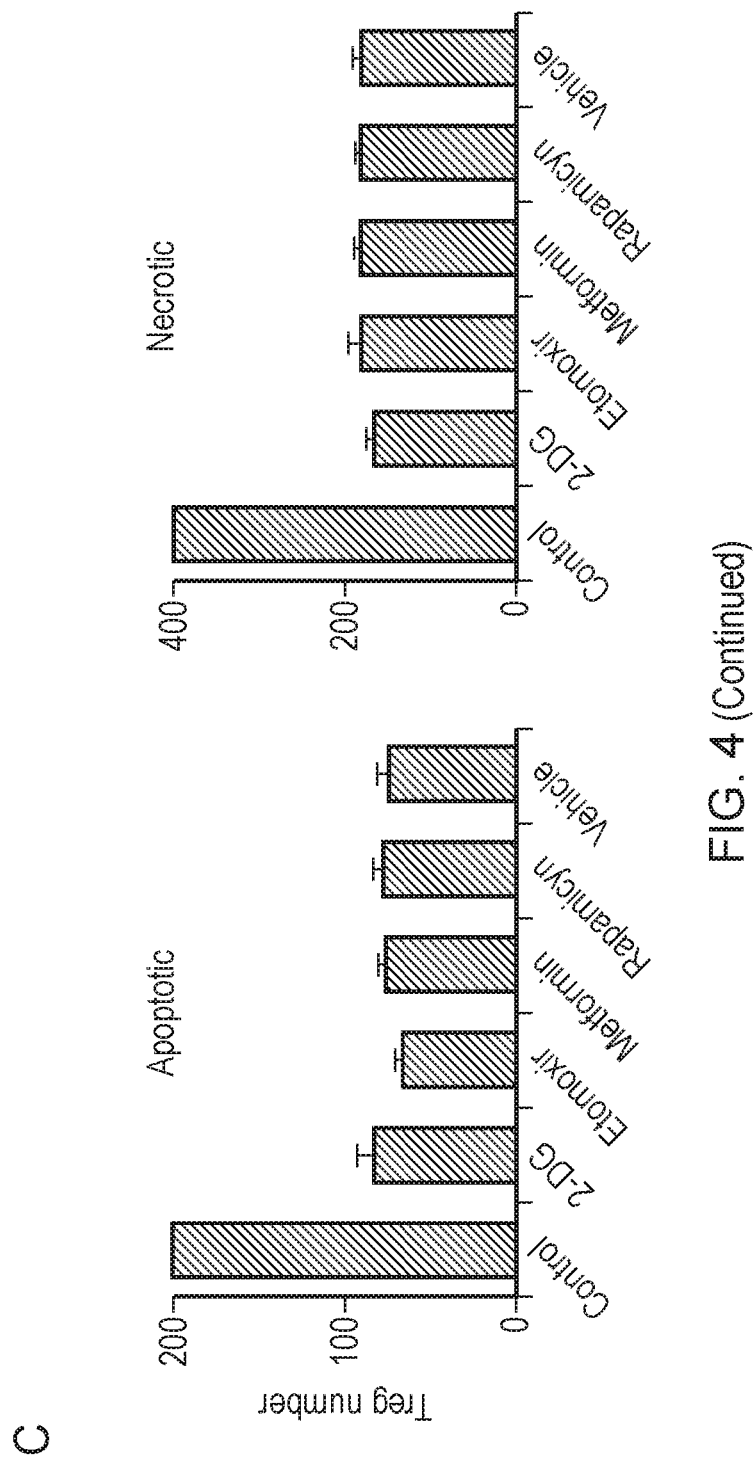
Figure 5:
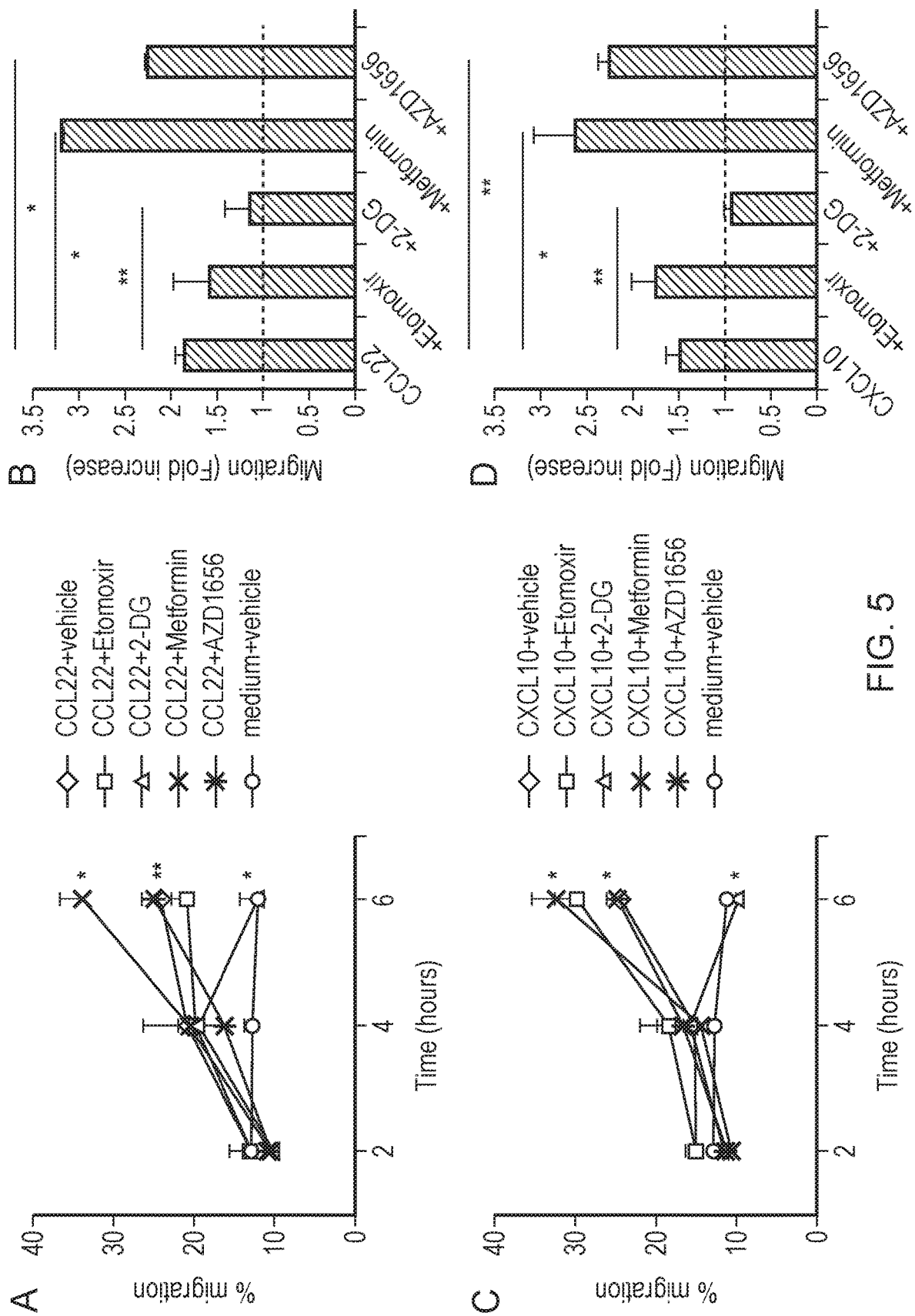
FIG. 5. Tregs were treated with the indicated metabolism-targeting drugs for 4-6 hours, extensively washed and cultured overnight in medium alone. Migration of drug-exposed Tregs in response to CCL22 (300 ng/ml, A-B) CXCL10 (300 ng/ml, C-D) was assessed by a 6 hr chemokinesis transwell assay (106/well). Results are expressed as the mean percentage of migrated cells in a typical experiment performed in triplicate±SD (A, C). Data obtained at 6 hours from three independent experiments of identical design and normalized by spontaneous migration±SD are shown in panel B and D. $*P<0.05$.
Figure 6:
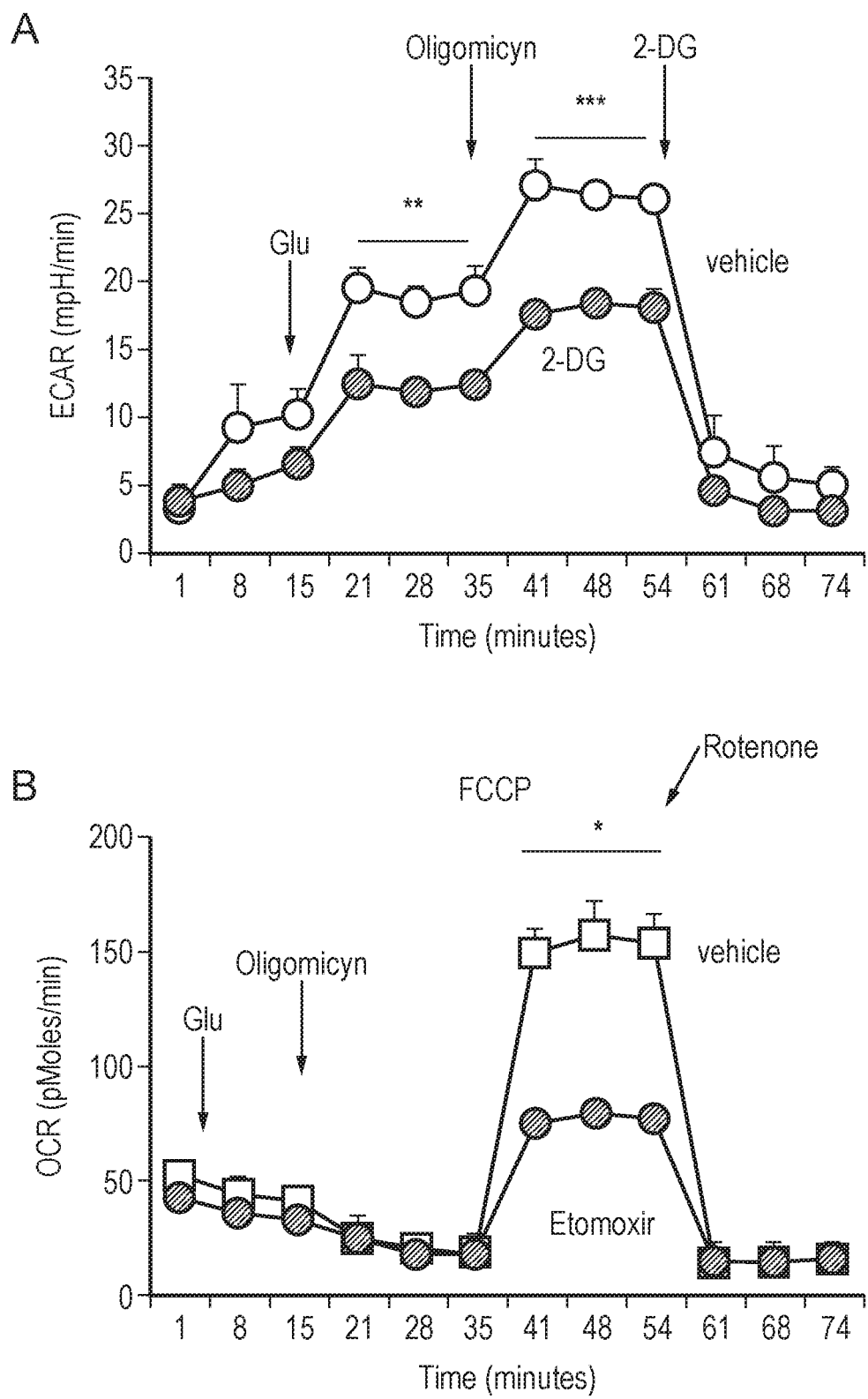
FIG. 6. Tregs were treated with the 2-DG (A) or Etomoxir (B) for 4-6 hours, extensively washed and cultured overnight in medium alone. Tregs were then rested in serum free, unbuffered XF assay medium (Seahorse biosciences) for 1 hour prior to seeding ($6\times10^5$/well) into Seahorse XF24 cell plates for fluxometric analysis. Wells were injected first with glucose. Further injections with the indicated substances followed at the indicated time points (arrows). ECAR=extracellular acidification rate, which is indicative of glycolysis.

We explored the possibility that, like conventional T cells (Tconv), Tregs utilize glycolysis for migration, by inhibiting this pathway with the glucose analogue 2-deoxyglucose (2-DG). Tregs exposed to 2-DG migrated inefficiently both in vitro (FIG. 1A, C-D and FIG. 2A-B) and in vivo (FIG. 3A-B). In addition to extensive washing after exposure to the drugs, the inhibition of Treg chemotaxis through bare transwells excludes indirect effects of the drugs on the endothelium in these conditions. In contrast, activation of glycolysis using metformin, which stimulates glycolysis via AMP kinase, increased Treg motility (FIG. 1B, C-D and FIG. 2A-B) and trafficking (FIG. 3C-D). None of the drugs affected Treg expression of migration-relevant receptors or viability at the doses used (FIG. 4A-C). To confirm that the effect of each of these compounds is retained once in vitro treated T cells are injected into recipient mice, Treg cells were exposed to the various drugs for 4 hours, extensively washed and incubated in culture medium alone for a further 16 hours. The effects on-drug-treated Treg motility were still apparent after the prolonged incubation without the compounds (FIG. 5A-D, FIG. 6A-B). Etomoxir is an inhibitor Acetyl-CoA carboxylase (ACC) phosphorylation and serves to show that Treg migration does not require fatty acid oxidation (FAO).

To confirm the induction of the glycolytic pathway by pro-migratory stimuli we subsequently tested the effect of engagement of the adhesion molecule integrin LFA-1, a key mediator of T cell migration, on aerobic glycolysis in Tregs. Immobilized or antibody-ligated recombinant mouse ICAM-1 (rICAM-1), a ligand of LFA-1, was used for this purpose.

Figure 7:
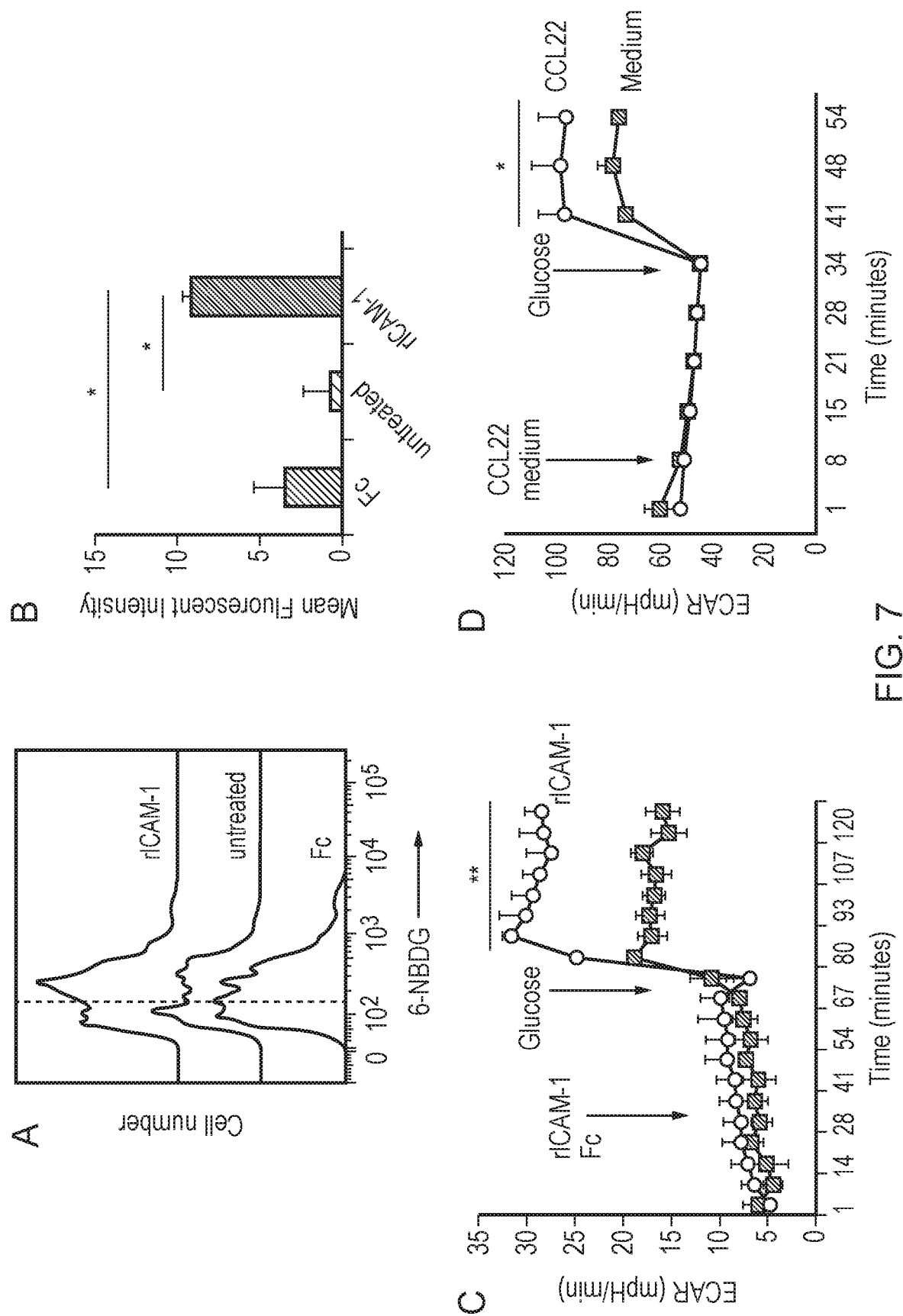
FIG. 7. A: Representative histograms of Tregs stimulated with plastic-bound recombinant (r)ICAM-1 or human IgG Fc fragments (Fc) for 45 minutes and then re-suspended in medium containing the glucose uptake indicator 6-NBDG (a fluorescently labeled glucose analogue which is not metabolized so renders the cell fluorescent if taken up) for 10 minutes. The mean MFI from 3 independent experiments±SD is shown in panel B. (n=3). ECAR of ICAM-1-(C) or CCL22-stimulated (D) Tregs was measured by an extracellular flux analyzer (Seahorse). IgFc or medium was used as a control, Recombinant molecules and glucose were added at the time points indicated (±SD n=5, N=2), $*p<0.05$, $**p<0.005$.

First we estimated LFA-1-induced glucose uptake using the glucose analogue 6-[N-(7-nitrobemz-2-oxa-1,3-diazol-4-yl)amino]-2-deoxyglucose (6-NBDG), which cannot be phosphorylated by hexokinases and accumulates in the cytoplasm in its fluorescent form. Tregs were stimulated with plastic-bound rICAM-1 or human IgGFc fragments (control) and 6-NBDG uptake was measured 30 minutes later by flow cytometry. As shown in FIG. 7A-B, LFA-1 stimulation significantly increased 6-NBDG uptake.

Figure 8:
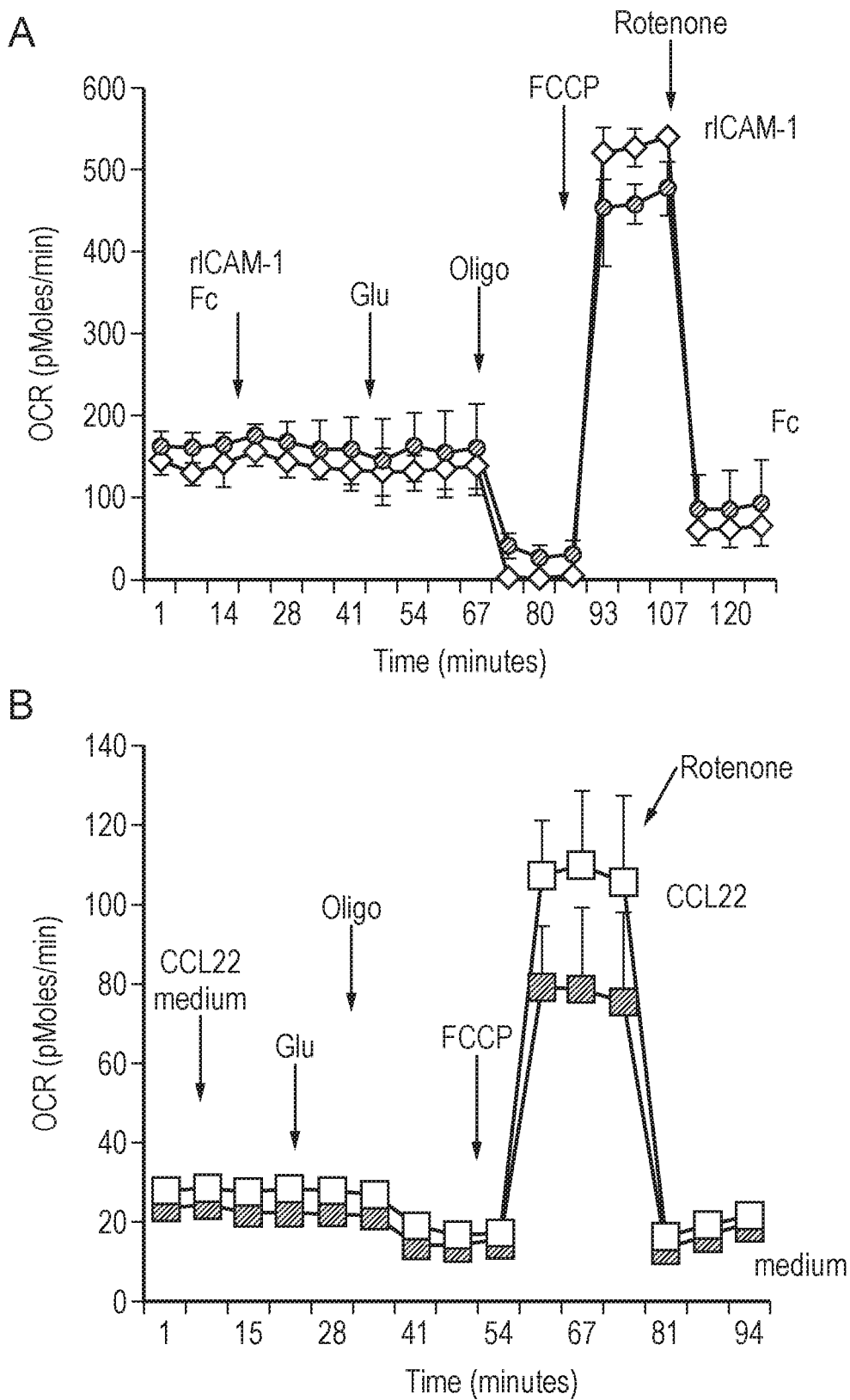
FIG. 8. In vitro expanded Tregs were first rested in serum free, unbuffered XF assay medium (Seahorse biosciences) for 1 hour prior to seeding ($6\times10^5$/well) into Seahorse XF24 cell plates for fluxometric analysis. Wells were injected first with recombinant ICAM-1 (or human Fc as a control, panel A) or CCL22 (or glucose-free medium as a control, panel B). Further injections with the indicated substances followed at the indicated time points (arrows), $*P<0.05$; $p<0.01$; $*p<0.005$.

Second, we measured the effects of LFA-1 engagement or exposure to the chemokine CCL22 (CCR4 ligand) on the extracellular acidification rate (ECAR), which quantifies proton production as a surrogate for lactate production, and thus reflects overall glycolytic flux. ECAR increase upon glucose supply was significantly enhanced following LFA-1 or CCR4 (FIG. 7C-D) stimulation. The oxygen consumption rate (OCR), a measure of mitochondrial respiration, was not affected (FIG. 8A-B).

Example 2

Figure 9:
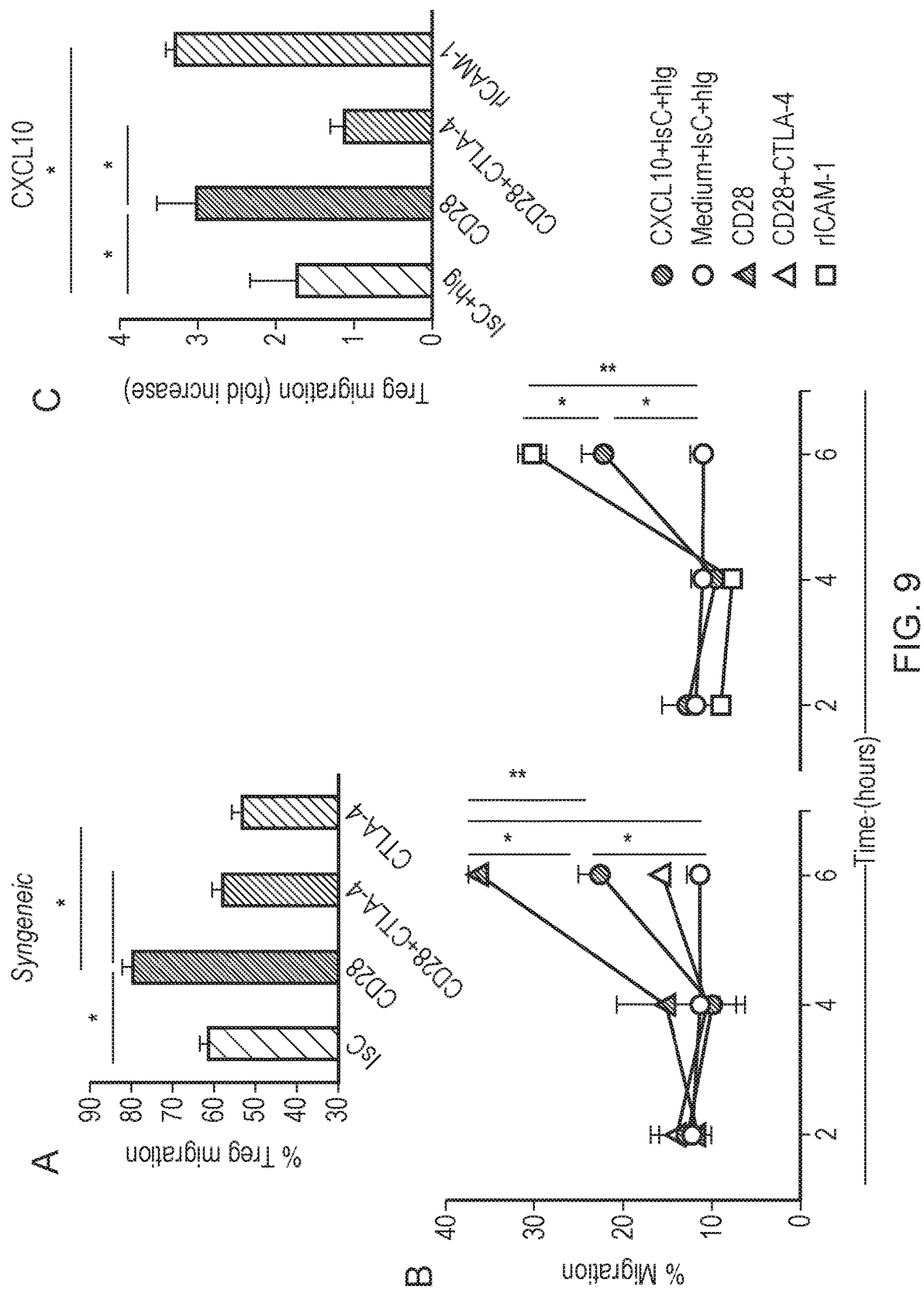
FIG. 9. CD28 and CTLA4 differentially regulate Treg cell migration. Tregs were stimulated by ligation of agonist antibodies (Schneider et al., 2005; Wells et al., 2001) recognizing CD28 or CTLA-4 at 37° C. for 45 minutes. A-C: migration of antibody-stimulated Treg through IFN-γ-treated syngeneic endothelial cell (EC) monolayers (A) or in response to CXCL10 chemokine (B-C) was monitored in transwell-based assays. In panel A results are expressed as the mean percentage of migrated cells in three independent experiments of identical design±SD. In panel B results are expressed as the mean percentage of migrated cells in a typical experiment performed in triplicate±SD. Data obtained at 6 hours from three independent experiments of identical design and normalized by spontaneous migration±SD are shown in panel C.
Figure 10:
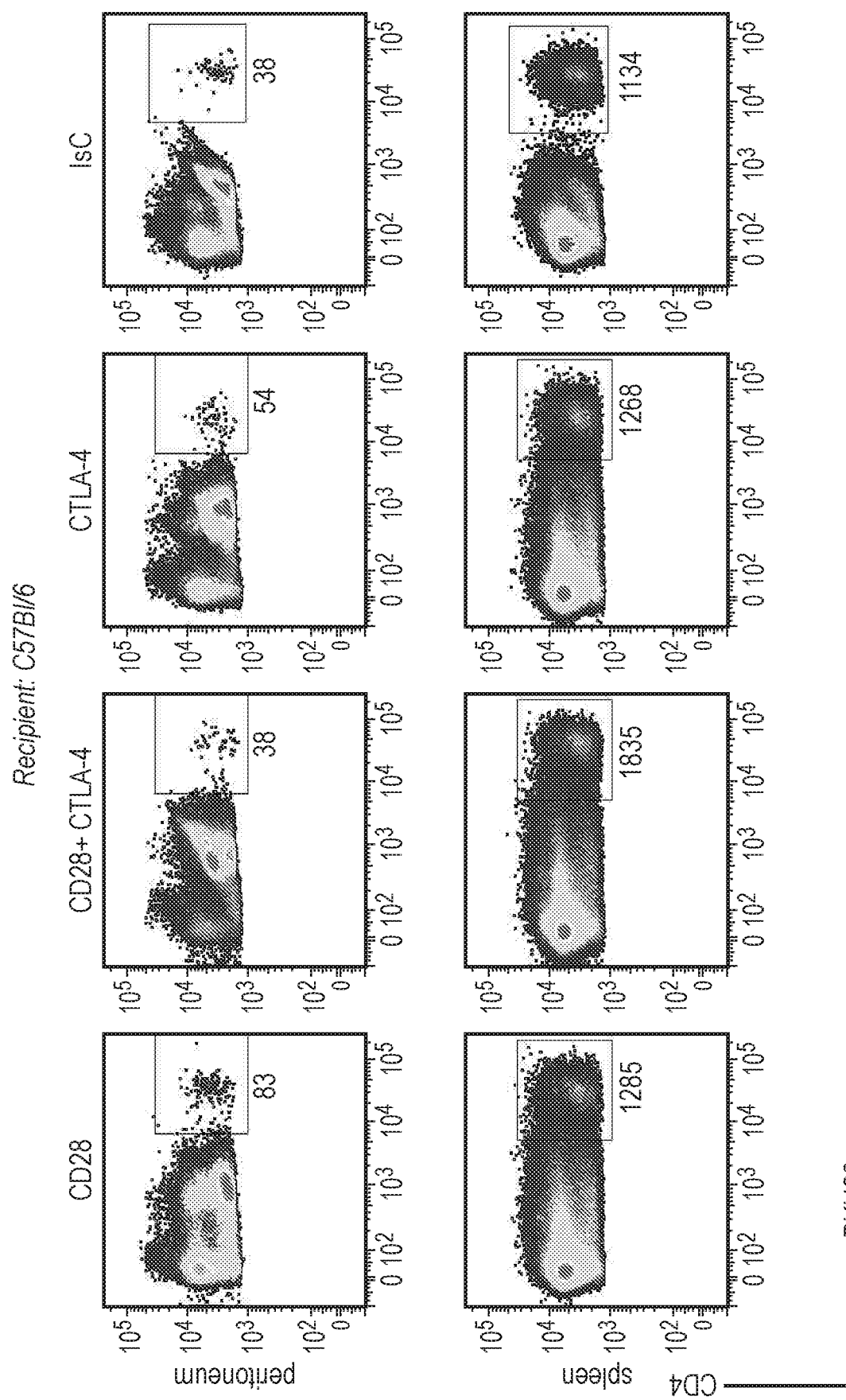
FIG. 10. Tregs were stimulated with CD28, and/or CTLA-4 antibodies prior to adoptive transfer into syngeneic recipients, which had been treated with IFN-γ i.p. 48 hours earlier to promote localized recruitment (Fu et al., 2014). Treg migration into the peritoneal cavity was assessed 16 hours later. Localization to the spleen, where entry occurs in a passive manner (Fu et al., 2016), was measured as a control. Given that the Treg population was adoptively transferred, absolute numbers of labeled cells were used in the data analysis. Significantly higher numbers of Tregs accumulated in the peritoneal cavity following CD28 stimulation. Concomitant CTLA-4 stimulation inhibited CD28- induced migration, while CTLA-4 triggering on its own did not have any effect. Representative dot plots from 3 animals are shown in the top panels. The bottom graphs indicate the mean absolute number of labeled cells recovered in 4 animals±SD. (N=3).

CD28 and CTLA-4 Regulate Treg Migration Through Modulation of the Glycolytic Pathway First, we confirmed that antibody-activation of CD28 enhances ex vivo expanded Treg TEM (FIG. 9A) and chemotaxis (FIG. 9B-C) in vitro and migration in vivo (FIG. 10), without affecting expression of relevant receptors (data not shown). Also, we observed that while CTLA-4 triggering alone did not affect Treg migration, co-ligation with CD28 abrogated CD28-induced migration (FIG. 9A-B).

Second, we measured the impact of CD28 and CTLA-4 signals on the glycolytic pathway in Tregs. CD28 triggering significantly increased 6-NBDG uptake (FIG. 11A-B) and glycolytic flux (FIG. 12A) compared to treatment with an isotype control and secondary antibodies. In contrast, CTLA-4 stimulation did not affect either glucose uptake or ECAR on its own but when co-ligated CTLA-4 signals prevented CD28-induced glucose uptake and ECAR increase. The oxygen consumption rate (OCR) was not affected by triggering of either costimulatory receptor (data not shown).

We further explored the link between costimulatory signals and metabolic regulation of motility by analyzing the metabolic activity and migration of CTLA-4-deficient Tregs. In these experiments we used as stimulator recombinant (r)CD80, a ligand shared by CD28 and CTLA-4. Compared to WT Tregs, CTLA-4-deficient Tregs spontaneously displayed a prolonged increase of ECAR in response to glucose (FIG. 12B)—even taking into account a higher acidification baseline. As expected, the ECAR of WT Treg cells activated with recombinant CD80 remained unchanged, due to simultaneous CD28 and CTLA-4 engagement (FIG. 13A), while CTLA-4-deficient Tregs further increased their glycolytic response to glucose addition (FIG. 13B). Despite CTLA-4 KO Treg OCR being spontaneously higher than that of their WT counterpart, it was not affected by either CD28 or CTLA-4 signals (data not shown).

In parallel, we tested TEM by rCD80-stimulated CTLA-4 KO Tregs through IFN-γ-activated syngeneic EC. As shown in FIG. 14A, CTLA-4KO Tregs stimulated with recombinant CD80 displayed enhanced migration through EC while CTLA-4-expressing Tregs did not respond to such stimulation, supporting the conclusion that CTLA-4 signals inhibit CD28-induced glycolysis and migration.

To investigate whether control of Treg migration by CD28 and CTLA-4 occurs via modulation of glycolysis, we analyzed the effect of CD28 and/or CTLA-4 stimulation during TEM in glucose-depleted medium. As shown in FIG. 14B, glucose depletion prevented the increase in motility induced by CD28 signals. The results were not influenced by cell distress associated with glucose deprivation as baseline low levels of migration remained similar in both glucose-sufficient and -deficient conditions.

In vivo, the CD28-glycolysis-migration axis was analyzed by monitoring 6-NBDG uptake by CD28-stimulated migrating Tregs. To this aim, we used a tissue infiltration model in which the ability of Tregs injected in the peritoneal cavity to infiltrate the peritoneal membrane is quantified (Mirenda et al., 2007). This model was chosen as 6-NBDG fluorescence is rapidly lost with time, making it technically impossible to track T cells transferred intravenously long-term. Tregs were labeled with PKH26 (red fluorescence; FIG. 15A, second column) and then underwent CD28 ligation with or without CTLA-4 triggering, or received isotype-matched and secondary antibodies as a control prior to i.p. injection in syngeneic mice treated with IFN-γ 48 hours earlier. 6-NBDG (green fluorescence; FIG. 15A, third column) was injected i.p. immediately after the cells, thus allowing parallel evaluation of tissue infiltration and glucose uptake by labeled Tregs in vivo. As shown in FIG. 15A-C, CD28 activation substantially increased the number of Tregs infiltrating the peritoneum and displaying 6-NBDG uptake (yellow fluorescence, merge; FIG. 15A, fourth column), indicating that Treg migration directly correlates with glucose uptake in vivo. Both these effects were prevented by CTLA-4 co-ligation.

Example 3

Pro-Migratory Stimuli Induce Metabolic Reprogramming

We have previously shown that in Tconv cells, activation of glycolysis during migration occurs via transcriptional and post-transcriptional regulation of the enzyme Hexokinase (HK)I (Haas et al., 2015). We therefore analyzed the expression of a number of glycolytic enzymes by expanded Tregs 4 hours after CD28 and CTLA-4 stimulation. CD28 stimulation led to a modest increase in HKI, Enolase and Aldolase expression by Tregs (FIG. 16A-B). Unexpectedly, the most substantial increase was observed in the expression of the HK isoenzyme glucokinase (HKIV or GCK), a rate-limiting enzyme key to hepatocyte and pancreatic beta cell function, whose expression by T cells has not been previously reported. Concomitant CTLA-4 triggering inhibited CD28-induced enzyme expression.

We extended our analysis also to HKII and observed that, like that of GCK, a substantially enhanced expression of this enzyme occurred as early as 5 minutes after stimulation not only by CD28 signals, but also following LFA-1 triggering by recombinant ICAM-1 (FIG. 17A), suggesting that both stimuli enhance enzyme expression also by post-transcriptional mechanisms.

We then measured transcription of the GCK, HKI and HKII genes, which was indeed increased by LFA-1 or CD28 stimulation (FIG. 17B, data for HKI and HKII not shown). As expected, enzyme induction by CD28 was prevented by CTLA-4 triggering. In this set of experiments, transcription of the GCK regulatory protein (GCKR) gene (FIG. 17C), a post-transcriptional regulator which blocks free cytoplasmic GCK (Farrelly et al., 1999). Confocal analysis of expression and co-localization of GCK and GCKR following CD28 and LFA-1 activation confirmed that both CD28 and LFA1 stimuli decrease GCKR expression, concomitant to a substantial increase of GCK availability (FIG. 18A-B).

To address the relative contribution of HKII and GCK activity to Treg motility, Tregs were treated with either the GCK activator AZD1656 (Bonn et al., 2012) or with the HKII-selective inhibitor Clotrimazole (CLT), which inhibits the glycolytic flux and respiration in CD3/CD28-stimulated Tconv cells (FIG. 19A-B)(van der Windt et al., 2013). GCK activation significantly enhanced Treg migration to the inflamed tissue (FIG. 20A), but did not affect Treg division (FIG. 20B). Vice versa, CLT was effective at inhibiting PCNA upregulation by Tregs (FIG. 20C) in response to allogeneic DCs but did not affect rICAM-1-mediated induction of glycolysis (FIG. 21A), or Treg migration to inflamed peritoneum in vivo (FIG. 21B).

Example 4

Effect of GCK Activation on Skin Grant Rejection

To establish the selectivity of GCK usage by Tregs to sustain their motility, we compared the effect of pharmacological activation of GCK on the survival of B6Kd-derived skin grafts transplanted in C57BL/6 recipients. Some recipients were treated daily with the selective GCK activator AZD1656 (10 mg/kg twice daily) for 2 weeks after transplantation. This schedule was designed in order to promote migration of endogenous Tregs during the early stages of the alloresponse. Control groups received saline solution with vehicle alone. As shown in FIG. 22, a short treatment with AZD1656 alone was sufficient to significantly delay skin graft rejection.

Example 5

Human Tregs from Homozygous Carriers of a Loss-of-Function GCKR Gene Display Enhanced Motility To test the physiological relevance of the above-identified pathway in the human system, we analyzed the number and functional behaviour of circulating Tregs (defined as CD25high CD127low) from homozygous carriers of a loss-of-function polymorphism in the GCKR gene (C to T, P446L). P446L-GCKR gene has reduced inhibitory activity toward GCK, and has been associated with decreased fasting plasma glucose and enhanced triglyceride synthesis via increased GCK activity in the liver (Beer et al., 2009).

The number of circulating Treg was significantly decreased in carriers of the rare allele P446L of GCKR gene compared to carriers of the WT allele (FIG. 23A-B) while other $CD4^+$ T cell populations were unaffected (data not shown). Importantly, P446L-GCKR Tregs displayed significantly increased chemokine-induced motility compared to WT-GCKR Tregs, while Tconv cell migration was unaffected (FIG. 24A-B). The suppressive ability and phenotype of P446L-GCKR Tregs did not significantly differ from that of WT-GCKR Tregs (data not shown), including expression of CCR7 (FIG. 25A-B), the receptor for the chemokines used in the migration assays. In addition, chemokine-induced molecular events upstream of GCK activation, including glucose uptake and Rictor-dependent AKT phosphorylation at serine 473 were comparable in P446L- and WT-GCKR Tregs and Tconv (data not shown), in further support of a key role of increased GCK availability in enhanced P446L Treg motility.

Discussion

The present inventors have investigated the metabolic pathways that sustain migration of thymic Tregs and how these pathways become engaged by pro-migratory signals.

The data indicate that migratory stimuli induce metabolic reprogramming of Tregs towards aerobic glycolysis. The dichotomy between regulation of glycolysis during Treg proliferation and migration is reflected in the enzymatic machinery engaged for these cellular responses. Metabolic reprogramming following antigen activation of conventional T cells involves a substantial increase of hexokinase activity, which is dependent on a transcriptional switch in HK isozyme expression from HKI to HKII, which has higher affinity for glucose (Bosca et al., 1988; Marjanovic et al., 1990; Wang et al., 2011). In addition—and as a likely consequence of mTORC2 activation—pro-migratory signals substantially enhance GCK expression. GCK has been shown to be one of the main targets downstream of mTORC2-mediated signaling in the liver (Hagiwara et al., 2012).

The present inventors provide evidence that this pathway is operational in the human immune system. The number of circulating Tregs was significantly decreased in carriers of a GCKR loss-of-function variant and mutant Tregs display significantly enhanced motility, suggesting increased localization in tissues. Importantly, migration of Tconv is not affected by loss of GCKR inhibition and increased GCK activity.

Preferential utilization of GCK by migrating Tregs is an interesting feature. Unlike other hexokinases, GCK has a much lower affinity for glucose, which is within the physiological plasma glucose range (S0.5≈7 mM) and is less susceptible to inhibition by the glycolysis metabolite glucose 6-phosphate (Lenzen, 2014). The use of GCK by Tregs might explain the previous report of a delayed polarization rate of Treg cells, compared to Tconv cells, in response to CD28 stimulation (Muller et al., 2008). CD28-stimulated Tregs were shown to undergo early and late waves of migration, which might reflect the posttranscriptional and transcriptional increase in GCK expression, which we observed.

During immune responses, the ability of CD28 and CTLA-4 to function as a metabolic switch at least in part explains their opposing effects on T cell division and function. For example, transient CTLA-4 expression following activation serves to shut down glycolysis thus supporting reprogramming of long-lived memory CD8+ T cells to FAO (O'Sullivan et al., 2014), thus promoting the contraction phase of T cell responses and maintaining homeostasis by favouring the induction of anergy (Zheng et al., 2009).

While the functional effects of CTLA-4 in the regulation of effector immunity are well established, the contribution of CTLA-4 to Treg function is not completely understood. CTLA-4-deficient mice display normal numbers of Tregs, which however appear to be defective in their suppressive function in vivo (Wing et al., 2008), but not in vitro (Tang et al., 2004). The observations herein show that, by antagonizing CD28-induced migratory signals, CTLA-4 is required for tissue retention of Treg localization in vivo (for example), rather than for their suppressive activity.

Impaired migration of $CD28^{Y170F}$ Tregs in response to activation of innate immunity also indicates that CD28 signals instruct Treg mobilization and redistribution from lymphoid tissue—where CD28 engagement is likely to take place during interaction with activated DCs—to the blood stream.

In summary, this study describes a novel pathway for the metabolic regulation of motility and migration induced in Tregs by pro-migratory stimuli. As the signaling mediators involved in the metabolic reprogramming of proliferating Treg cells are distinct from those regulating motility, selective targeting of these enzymes allows for the modulation of distinct Treg functions in therapeutic settings.

SELECTED REFERENCES

Ammirati, E., Cianflone, D., Vecchio, V., Banfi, M., Vermi, A. C., De Metrio, M., Grigore, L., Pellegatta, F., Pirillo, A., Garlaschelli, K., et al. (2012). Effector Memory T cells Are Associated With Atherosclerosis in Humans and Animal Models. Journal of the American Heart Association 1, 27-41.

Bain, S. C., Barnett, A. H. and Todd J. A. (1992). Lack of association between type 1 diabetes and the glucokinase gene. Lancet 340: 54-55.

Baragetti, A., Palmen, J., Garlaschelli, K., Grigore, L., Pellegatta, F., Tragni, E., Catapano, A. L., Humphries, S. E., Norata, G. D., and Talmud, P. J. (2015). Telomere shortening over 6 years is associated with increased subclinical carotid vascular damage and worse cardiovascular prognosis in the general population. Journal of internal medicine 277, 478-487.

Beer, N. L., Tribble, N. D., McCulloch, L. J., Roos, C., Johnson, P. R., Orho-Melander, M., and Gloyn, A. L. (2009). The P446L variant in GCKR associated with fasting plasma glucose and triglyceride levels exerts its effect through increased glucokinase activity in liver. Hum Mol Genet 18, 4081-4088.

Bernstein, B. W., and Bamburg, J. R. (2003). Actin-ATP hydrolysis is a major energy drain for neurons. The Journal of neuroscience: the official journal of the Society for Neuroscience 23, 1-6.

Bonn, P., Brink, D. M., Fagerhag, J., Jurva, U., Robb, G. R., Schnecke, V., Svensson Henriksson, A., Waring, M. J., and Westerlund, C. (2012). The discovery of a novel series of glucokinase activators based on a pyrazolopyrimidine scaffold. Bioorganic & medicinal chemistry letters 22, 7302-7305.

Bosca, L., Mojena, M., Diaz-Guerra, J. M., and Marquez, C. (1988). Phorbol 12,13-dibutyrate and mitogens increase fructose 2,6-bisphosphate in lymphocytes. Comparison of lymphocyte and rat-liver 6-phosphofructo-2-kinase. Eur J Biochem 175, 317-323.

Boulbes, D., Chen, C. H., Shaikenov, T., Agarwal, N. K., Peterson, T. R., Addona, T. A., Keshishian, H., Carr, S. A., Magnuson, M. A., Sabatini, D. M., et al. (2010). Rictor phosphorylation on the Thr-1135 site does not require mammalian target of rapamycin complex 2. Mol Cancer Res 8, 896-906.

Chang, T. T., Jabs, C., Sobel, R. A., Kuchroo, V. K., and Sharpe, A. H. (1999). Studies in B7-deficient mice reveal a critical role for B7 costimulation in both induction and effector phases of experimental autoimmune encephalomyelitis. J Exp Med 190, 733-740.

Chen, Z., Herman, A. E., Matos, M., Mathis, D. and Benoist, C. (2005). Where CD4+CD25+ T reg cells impinge on autoimmune diabetes. J Exp Med 202, 1387-97.

Chi, H. (2012). Regulation and function of mTOR signalling in T cell fate decisions. Nature reviews Immunology 12, 325-338.

Clarke, F. M., and Masters, C. J. (1975). On the association of glycolytic enzymes with structural proteins of skeletal muscle. Biochim Biophys Acta 381, 37-46.

Cooles, F. A. H., Isaacs, J. D. and Anderson, A. E. (2013). Treg Cells in Rheumatoid Arthritis: An Update. Curr Rheumatol Reports 15: 352.

Cybulski, N., and Hall, M. N. (2009). TOR complex 2: a signaling pathway of its own. Trends Biochem Sci 34, 620-627.

Dang, E. V., Barbi, J., Yang, H. Y., Jinasena, D., Yu, H., Zheng, Y., Bordman, Z., Fu, J., Kim, Y., Yen, H. R., et al. (2011). Control of T(H)17/T(reg) balance by hypoxia-inducible factor 1. Cell 146, 772-784.

Deng, Y., Chang, C. and Lu, Q. (2016). The Inflammatory Response in Psoriasis: a Comprehensive Review. Clin Rev Allergy Immunol 50, 377-389.

Denning, T. L., Kim, G. and Kronenberg, M. (2005). Cutting edge: CD4+CD25+regulatory T cells impaired for intestinal homing can prevent colitis. J Immunol 174, 7487-91.

Ding, Y., Xu, J. and Bromberg, J. S. (2012). T regulatory cell migration during an immune response. Trends Immunol 33, 174-180.

Farrelly, D., Brown, K. S., Tieman, A., Ren, J., Lira, S. A., Hagan, D., Gregg, R., Mookhtiar, K. A., and Hariharan, N. (1999). Mice mutant for glucokinase regulatory protein exhibit decreased liver glucokinase: a sequestration mechanism in metabolic regulation. Proc Natl Acad Sci USA 96, 14511-14516.

Frauwirth, K. A., Riley, J. L., Harris, M. H., Parry, R. V., Rathmell, J. C., Plas, D. R., Elstrom, R. L., June, C. H., and Thompson, C. B. (2002). The CD28 signaling pathway regulates glucose metabolism. Immunity 16, 769-777.

Gan, X., Wang, J., Su, B., and Wu, D. (2011). Evidence for direct activation of mTORC2 kinase activity by phosphatidylinositol 3,4,5-trisphosphate. J Biol Chem 286, 10998-11002.

Fu, H., Kishore, M., Gittens, B., Wang, G., Coe, D., Komarowska, I., Infante, E., Ridley, A. J., Cooper, D., Perretti, M., et al. (2014). Self-recognition of the endothelium enables regulatory T-cell trafficking and defines the kinetics of immune regulation. Nat Commun 5, 3436.

Fu, H., Ward, E. J., and Marelli-Berg, F. M. (2016). Mechanisms of T cell organotropism. Cell Mol Life Sci 73, 3009-3033.

Gerriets, V. A., Kishton, R. J., Johnson, M. O., Cohen, S., Siska, P. J., Nichols, A. G., Warmoes, M. O., de Cubas, A. A., MacIver, N. J., Locasale, J. W., et al. (2016). Foxp3 and Toll-like receptor signaling balance Treg cell anabolic metabolism for suppression. Nat Immunol 17, 1459-1466.

Grewal, A. S., Sekhon, B. S., and Lather, V. (2014). Recent Updates on Glucokinase Activators for the Treatment of Type 2 Diabetes Mellitus. Mini Rev Med Chem 14, 585-602.

Haas, R., Smith, J., Rocher-Ros, V., Nadkarni, S., Montero-Melendez, T., D'Acquisto, F., Bland, E. J., Bombardieri, M., Pitzalis, C., Perretti, M., et al. (2015). Lactate Regulates Metabolic and Pro-inflammatory Circuits in Control of T Cell Migration and Effector Functions. PLoS biology 13, e1002202.

Hagiwara, A., Cornu, M., Cybulski, N., Polak, P., Betz, C., Trapani, F., Terracciano, L., Heim, M. H., Ruegg, M. A., and Hall, M. N. (2012). Hepatic mTORC2 activates glycolysis and lipogenesis through Akt, glucokinase, and SREBP1c. Cell Metab 15, 725-738.

Humrich, J. Y and Riemekasten, G. (2016). Restoring regulation—IL-2 therapy in systemic lupus erythematosus. Exp Rev Clin Immunol 12, 1153-1160.

Jacobs, S. R., Herman, C. E., Maciver, N. J., Wofford, J. A., Wieman, H. L., Hammen, J. J., and Rathmell, J. C. (2008). Glucose uptake is limiting in T cell activation and requires CD28-mediated Akt-dependent and independent pathways. J Immunol 180, 4476-4486.

Jain, N., Miu, B., Jiang, J. K., McKinstry, K. K., Prince, A., Swain, S. L., Greiner, D. L., Thomas, C. J., Sanderson, M. J., Berg, L. J., et al. (2013). CD28 and ITK signals regulate autoreactive T cell trafficking. Nat Med 19, 1632-1637.

Jarmin, S. J., David, R., Ma, L., Chai, J.-G., Dewchand, H., Takesono, A., Ridley, A. J., Okkenhaug, K., and Marelli-Berg, F. M. (2008). Targeting T cell receptor-induced phosphoinositide-3-kinase p110delta activity prevents T cell localization to antigenic tissue. J Clin Invest 118, 1154-1164.

Jung, J., Yoon, T., Choi, E. C., and Lee, K. (2002). Interaction of cofilin with triose-phosphate isomerase contributes glycolytic fuel for Na,K-ATPase via Rho-mediated signaling pathway. J Biol Chem 277, 48931-48937.

Lenzen, S. (2014). A fresh view of glycolysis and glucokinase regulation: history and current status. The Journal of biological chemistry 289, 12189-12194.

Livak, K. J., and Schmittgen, T. D. (2001). Analysis of relative gene expression data using real-time quantitative PCR and the 2(-Delta Delta C(T)) Method. Methods 25, 402-408.

Lorenz, M. W., Polak, J. F., Kavousi, M., Mathiesen, E. B., Volzke, H., Tuomainen, T. P., Sander, D., Plichart, M., Catapano, A. L., Robertson, C. M., et al. (2012). Carotid intima-media thickness progression to predict cardiovascular events in the general population (the PROG-IMT collaborative project): a meta-analysis of individual participant data. Lancet 379, 2053-2062.

Marelli-Berg, F. M., Peek, E., Lidington, E. A., Stauss, H. J., and Lechler, R. I. (2000). Isolation of endothelial cells from murine tissue. J Immunol Methods 244, 205-215.

Marjanovic, S., Eriksson, I., and Nelson, B. D. (1990). Expression of a new set of glycolytic isozymes in activated human peripheral lymphocytes. Biochim Biophys Acta 1087, 1-6.

Masui, K., Cavenee, W. K., and Mischel, P. S. (2014). mTORC2 in the center of cancer metabolic reprogramming. Trends Endocrinol Metab 25, 364-373.

Michalek, R. D., Gerriets, V. A., Jacobs, S. R., Macintyre, A. N., MacIver, N. J., Mason, E. F., Sullivan, S. A., Nichols, A. G., and Rathmell, J. C. (2011). Cutting edge: distinct glycolytic and lipid oxidative metabolic programs are essential for effector and regulatory CD4+ T cell subsets. J Immunol 186, 3299-3303.

Mirenda, V., Jarmin, S. J., David, R., Dyson, J., Scott, D., Gu, I., Lechler, R. I., Okkenhaug, K., and Marelli-Berg, F. M. (2007). Physiological and aberrant regulation of memory T cell trafficking by the costimulatory molecule CD28. Blood 109, 2968-2977.

Muller, N., van den Brandt, J., Odoardi, F., Tischner, D., Herath, J., Flugel, A., and Reichardt, H. M. (2008). A CD28 superagonistic antibody elicits 2 functionally distinct waves of T cell activation in rats. J Clin Invest 118, 1405-1416.

Murata, T., Katagiri, H., Ishihara, H., Shibasaki, Y., Asano, T., Toyoda, Y., Pekiner, B., Pekiner, C., Miwa, I., and Oka, Y. (1997). Co-localization of glucokinase with actin filaments. FEBS Lett 406, 109-113.

Newson, J., Stables, M., Karra, E., Arce-Vargas, F., Quezada, S., Motwani, M., Mack, M., Yona, S., Audzevich, T., and Gilroy, D. W. (2014). Resolution of acute inflammation bridges the gap between innate and adaptive immunity. Blood 124, 1748-1764.

Norata, G. D., Garlaschelli, K., Grigore, L., Tibolla, G., Raselli, S., Redaelli, L., Buccianti, G., and Catapano, A. L. (2009). Circulating soluble receptor for advanced glycation end products is inversely associated with body mass index and waist/hip ratio in the general population. Nutrition, metabolism, and cardiovascular diseases: NMCD 19, 129-134.

Norata, G. D., Garlaschelli, K., Ongari, M., Raselli, S., Grigore, L., and Catapano, A. L. (2006). Effects of fractalkine receptor variants on common carotid artery intima-media thickness. Stroke 37, 1558-1561.

Norata, G. D., Ongari, M., Garlaschelli, K., Tibolla, G., Grigore, L., Raselli, S., Vettoretti, S., Baragetti, I., Noto, D., Cefalu, A. B., et al. (2007). Effect of the −420C/G variant of the resistin gene promoter on metabolic syndrome, obesity, myocardial infarction and kidney dysfunction. Journal of internal medicine 262, 104-112.

O'Sullivan, D., van der Windt, G. J., Huang, S. C., Curtis, J. D., Chang, C. H., Buck, M. D., Qiu, J., Smith, A. M., Lam, W. Y., DiPlato, L. M., et al. (2014). Memory CD8(+) T cells use cell-intrinsic lipolysis to support the metabolic programming necessary for development. Immunity 41, 75-88.

Okkenhaug, K., Wu, L., Garza, K. M., La Rose, J., Khoo, W., Odermatt, B., Mak, T. W., Ohashi, P. S., and Rottapel, R. (2001). A point mutation in CD28 distinguishes proliferative signals from survival signals. Nat Immunol 2, 325-332.

Parry, R. V., Chemnitz, J. M., Frauwirth, K. A., Lanfranco, A. R., Braunstein, I., Kobayashi, S. V., Linsley, P. S., Thompson, C. B., and Riley, J. L. (2005). CTLA-4 and PD-1 receptors inhibit T-cell activation by distinct mechanisms. Molecular and cellular biology 25, 9543-9553.

Powell, J. D., and Delgoffe, G. M. (2010). The mammalian target of rapamycin: linking T cell differentiation, function, and metabolism. Immunity 33, 301-311.

Procaccini, C., De Rosa, V., Galgani, M., Abanni, L., Cali, G., Porcellini, A., Carbone, F., Fontana, S., Horvath, T. L., La Cava, A., et al. (2010). An oscillatory switch in mTOR kinase activity sets regulatory T cell responsiveness. Immunity 33, 929-941.

Reese, P. P., Shults, J., Bloom, R. D., Mussell, A., Harhay, M. N., Abt, P., Levine, M., Johansen, K. L., Karlawish, J. T., and Feldman, H. I. Functional Status, Time to Transplantation, and Survival Benefit of Kidney Transplantation Among Wait-Listed Candidates. *American journal of kidney diseases: the official journal of the National Kidney Foundation.* 7 Jul. 2015.

Schneider, H., Valk, E., da Rocha Dias, S., Wei, B., and Rudd, C. E. (2005). CTLA-4 up-regulation of lymphocyte function-associated antigen 1 adhesion and clustering as an alternate basis for coreceptor function. Proc Natl Acad Sci USA 102, 12861-12866.

Shi, L.Z., Wang, R., Huang, G., Vogel, P., Neale, G., Green, D. R., and Chi, H. (2011). HIF1alpha-dependent glycolytic pathway orchestrates a metabolic checkpoint for the differentiation of TH17 and Treg cells. The Journal of experimental medicine 208, 1367-1376.

Stephenson, E., Savvatis, K., Mohiddin, S. A. and Marelli-Berg, F. M. (2016). T-cell immunity in myocardial inflammation: pathogenic role and therapeutic manipulation. Br J Pharmacol DOI: 10.1111/bph.13613

Tai, X., Cowan, M., Feigenbaum, L., and Singer, A. (2005). CD28 costimulation of developing thymocytes induces Foxp3 expression and regulatory T cell differentiation independently of interleukin 2. Nature immunology 6, 152-162.

Tang, Q., Bluestone, J. A., and Kang, S. M. (2012). CD4(+)Foxp3(+) regulatory T cell therapy in transplantation. J Mol Cell Biol 4, 11-21.

Tang, Q., Boden, E. K., Henriksen, K. J., Bour-Jordan, H., Bi, M., and Bluestone, J. A. (2004). Distinct roles of CTLA-4 and TGF-beta in CD4+CD25+ regulatory T cell function. European journal of immunology 34, 2996-3005.

van der Windt, G. J., O'Sullivan, D., Everts, B., Huang, S. C., Buck, M. D., Curtis, J. D., Chang, C. H., Smith, A. M., Ai, T., Faubert, B., et al. (2013). CD8 memory T cells have a bioenergetic advantage that underlies their rapid recall ability. Proc Natl Acad Sci USA 110, 14336-14341.

Wang, R., Dillon, C. P., Shi, L. Z., Milasta, S., Carter, R., Finkelstein, D., McCormick, L. L., Fitzgerald, P., Chi, H., Munger, J., et al. (2011). The transcription factor Myc controls metabolic reprogramming upon T lymphocyte activation. Immunity 35, 871-882.

Weirather, J., Hofmann, U. D. W., Beyersdorf, N., Ramos, G. C., Vogel, B. Frey, A. Ertl., G., Kerkau, T and Frantz., S (2014) Foxp3+ CD4+ T Cells Improve Healing After Myocardial Infarction by Modulating Monocyte/Macrophage Differentiation. Circ Res 115: 55-67.

Wells, A. D., Walsh, M. C., Bluestone, J. A., and Turka, L. A. (2001). Signaling through CD28 and CTLA-4 controls two distinct forms of T cell anergy. J Clin Invest 108, 895-903.

Wieman, H. L., Wofford, J. A., and Rathmell, J. C. (2007). Cytokine stimulation promotes glucose uptake via phosphatidylinositol-3 kinase/Akt regulation of Glut1 activity and trafficking. Molecular biology of the cell 18, 1437-1446.

Wing, K., Onishi, Y., Prieto-Martin, P., Yamaguchi, T., Miyara, M., Fehervari, Z., Nomura, T., and Sakaguchi, S. (2008). CTLA-4 control over Foxp3+ regulatory T cell function. Science 322, 271-275.

Zheng, Y., Delgoffe, G. M., Meyer, C. F., Chan, W., and Powell, J. D. (2009). Anergic T cells are metabolically anergic. J Immunol 183, 6095-6101.

Zorn, E., Kim, H. T., Lee, S. J., Floyd, B. H., Litsa, D., Arumugarajah, S., Bellucci, R., Alyea, E. P., Antin, J. H., Soiffer, R. J. et al. (2005). Reduced frequency of FOXP3+ CD4+CD25+ regulatory T cells in patients with chronic graft-versus-host disease. Blood 106, 2903-2911.

The invention claimed is:

1. A method of treating or preventing a disease or condition in a subject, said method comprising administering a glycolysis-activating agent to the subject, wherein:
 (a) said treatment or prevention is mediated via the trafficking of endogenous regulatory T cells (Tregs); or
 (b) said disease or medical condition is alleviated by the trafficking of endogenous regulatory T cells (Tregs) to a tissue or organ.

2. The method according to claim 1, wherein the disease or medical condition is an immune-mediated disease or medical condition, optionally wherein:
 (a) the immune mediated disease or medical condition is an autoimmune disorder or a transplant related disorder; and/or
 (b) the immune mediated disease or medical condition is selected from: transplant rejection, allograft rejection, graft versus host disease (GVHD), systemic lupus erythematosus (SLE), multiple sclerosis (MS), psoriasis, Type I diabetes, Hashimoto's thyroiditis, autoimmune thyroiditis (AITD), myocarditis, myocardial infarction (MI), allergy, infection by virus, bacteria or parasite, cancer, inflammatory bowel disease (IBD), rheumatoid arthritis, autoimmune gastritis, colitis, antiglomerular basement nephritis, autoimmune hepatitis, primary biliary cirrhosis (PBC), alopecia areata, autoimmune progesterone dermatitis, autoimmune urticaria, pemphigus vulgaris, autoimmune polyendocrine syndrome (APS; with the exception of type 3 APS a.k.a. IPEX syndrome), autoimmune pancreatitis, Grave's disease, Sjogrens syndrome, coeliac disease, ulcerative colitis, antiphospholipid syndrome, autoimmune haemolytic anaemia, autoimmune thrombocytopenic purpura, pernicious anaemia, mixed connective tissue disease (MCTD), undifferentiated connective tissue disease (UCTD), psoriatic arthritis, relapsing polychondritis, rheumatic fever, dermatomyositis, myasthenia gravis, polymyositis, acute disseminated encephalomyelitis (ADEM), Guillain-Barré syndrome, Hashimoto's encephalopathy, transverse myelitis, sarcoidosis, autoimmune uveitis, autoimmune inner ear disease (AIED), Behcet's disease, giant cell arteritis, granulomatosis with polyangitis (EGPA), vasculitis, eczema, optionally wherein:
 (i) the immune mediated disease or medical condition is myocarditis;
 (ii) the immune mediated disease or medical condition is graft versus host disease (GVHD);
 (iii) the immune mediated disease or medical condition is transplant rejection; or
 (iv) the immune mediated disease or medical condition is rheumatoid arthritis.

3. The method of claim 1, wherein administering the glycolysis-activating agent to the subject comprises administering a pharmaceutical composition comprising the glycolysis-activating agent and a pharmaceutically acceptable carrier, vehicle, diluent or excipient to the subject.

4. A method of modulating the immune response in a subject, said method comprising administering a glycolysis-activating agent to the subject, the method optionally comprising:
 (a) suppressing the immune response of the subject; or
 (b) suppressing or regulating an autoimmune response in the subject.

5. The method according to claim 1, wherein the glycolysis-activating agent is a glucokinase (GCK)-activating agent, optionally wherein the GCK-activating agent is selected from: AZD1656, piragliatin, AZD6370, GKA 50, YH-GKA, PSN-010, LY2121260, ganoderan B, eupatilin, glucolipsin A, glucolipsin B, sinogliatin, GKM-001, TTP-399, SY-004, TMG-123, albiglutide, AM-9514, AMG-0696, AMG-1694, AMG-3969, LCZ-960, AZD-1092, AZD-5658, ARRY-403, BMS-820132, GKM-002, LY-2608204, MK-0941, R-1511, RO-281675, ZYGK-1, OP-286 CR, CM-3, DS-7309, LY-2599506, PF-04937319, PF-04991532, and TAK-329.

6. The method according to claim 1, wherein the Treg cell migrates to a diseased tissue or organ or a transplanted tissue or organ.

7. The method according to claim 1, wherein:

(a) said glycolysis-activating agent is administered conjointly with one or more further therapeutic agents, optionally wherein said further therapeutic agent is selected from the group consisting of: an immunosuppressant, a cell therapy, a tolerogenic dendritic cell therapy, an anti-inflammatory agent and a hormone replacement therapy;

(b) said glycolysis-activating agent is administered in a dosage unit form of 1 mg to 500 mg, optionally in a selected dosage unit form of 1, 10, 20, 50, 100, 200, 250 or 500 mg, optionally in a dosage unit form of about 100 mg;

(c) said glycolysis-activating agent is administered via the oral route;

(d) said glycolysis-activating agent is administered once, twice, three or four times daily;

(e) said glycolysis-activating agent is administered for a period of 1 week to 6 months, optionally for a period of 1 to 6 months, optionally for a period of 2 to 4 months, optionally for a period of about 3 months;

(f) said glycolysis-activating agent is administered via the oral route in a dosage unit form of about 100 mg twice daily for a period of about 3 months.

8. An ex vivo method of trafficking or mobilising a Treg cell comprising the step of activating glycolysis in the Treg cell by contacting the Treg cell with a glycolysis-activating agent.

9. A method of treating an immune mediated disease or medical condition comprising the steps of:

a) isolating Treg cells from a subject to be treated and/or isolating Treg cells from another subject or source;

b) expanding the Treg cells from step (a) to obtain sufficient numbers for therapy;

c) contacting or pre-treating the Treg cells from step (b) with a GCK-activating agent;

d) administering the Treg cells from step (c) into the subject to be treated.

10. An isolated, glycolytically-activated Treg cell.

11. A method of treating or preventing a disease or condition in a subject, comprising administering the glycolytically-activated Treg cell of claim 10 to said subject, wherein the disease or condition is alleviated by trafficking of endogenous Tregs to a tissue or organ.

12. The method according to claim 1, wherein:

(a) said glycolysis-activating agent is administered conjointly with one or more further therapeutic agents, optionally wherein said further therapeutic agent is selected from the group consisting of: an immunosuppressant, a cell therapy, a tolerogenic dendritic cell therapy, an anti-inflammatory agent and a hormone replacement therapy;

(b) said glycolysis-activating agent is administered in a dosage unit form of 1 mg to 500 mg, optionally in a selected dosage unit form of 1, 10, 20, 50, 100, 200, 250 or 500 mg, optionally in a dosage unit form of about 100 mg;

(c) said glycolysis-activating agent is administered via the oral route;

(d) said glycolysis-activating agent is administered once, twice, three or four times daily;

(e) said glycolysis-activating agent is administered for a period of 1 week to 6 months, optionally for a period of 1 to 6 months, optionally for a period of 2 to 4 months, optionally for a period of about 3 months;

(f) said glycolysis-activating agent is administered via the oral route in a dosage unit form of about 100 mg twice daily for a period of about 3 months; and/or (g) the disease or medical condition is selected from the group consisting of post-transplant diabetes and ischaemia-reperfusion injury.

13. The method according to claim 12, wherein the glycolysis-activating agent is a glucokinase (GCK)-activating agent, optionally wherein the GCK-activating agent is selected from: AZD1656, piragliatin, AZD6370, GKA 50, YH-GKA, PSN-010, LY2121260, ganoderan B, eupatilin, glucolipsin A, glucolipsin B, sinogliatin, GKM-001, TTP-399, SY-004, TMG-123, albiglutide, AM-9514, AMG-0696, AMG-1694, AMG-3969, LCZ-960, AZD-1092, AZD-5658, ARRY-403, BMS-820132, GKM-002, LY-2608204, MK-0941, R-1511, RO-281675, ZYGK-1, OP-286 CR, CM-3, DS-7309, LY-2599506, PF-04937319, PF-04991532, and TAK-329.

14. The method according to claim 5, wherein the GCK-activating agent is (a) AZD1656:

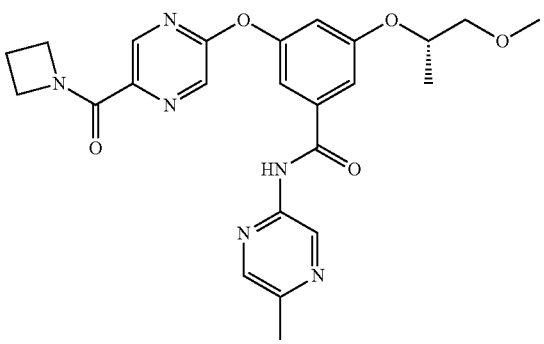 [SMILES: COC[C@H](C)Oc1cc(Oc2cnc(C(=O)N3CCC3)cn2)cc(C(=O)Nc2cnc(C)cn2)c1]

or a pharmaceutically acceptable salt thereof; or (b) GKA 50.

15. The method according to claim 13, wherein the GCK-activating agent is
  (a) AZD1656:
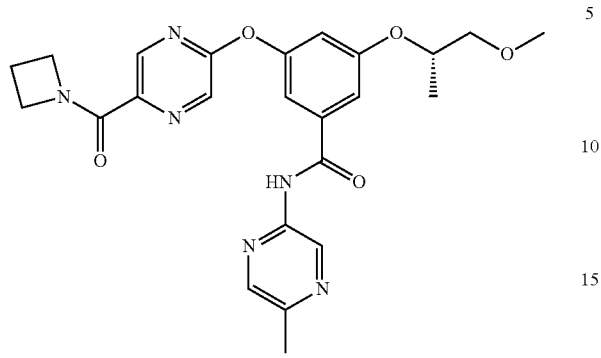
or a pharmaceutically acceptable salt thereof; or
  (b) GKA 50.
* * * * *